(12) United States Patent
Seehra

(10) Patent No.: US 8,338,377 B2
(45) Date of Patent: Dec. 25, 2012

(54) BMP-ALK3 ANTAGONISTS AND USES FOR PROMOTING BONE GROWTH

(75) Inventor: Jasbir Seehra, Lexington, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 170 days.

(21) Appl. No.: 12/750,604

(22) Filed: Mar. 30, 2010

(65) Prior Publication Data

US 2010/0266612 A1 Oct. 21, 2010

Related U.S. Application Data

(60) Provisional application No. 61/211,557, filed on Mar. 30, 2009, provisional application No. 61/306,331, filed on Feb. 19, 2010, provisional application No. 61/314,556, filed on Mar. 16, 2010.

(51) Int. Cl.
A61K 38/16 (2006.01)
C07K 14/00 (2006.01)
C07K 14/705 (2006.01)
C07K 14/71 (2006.01)

(52) U.S. Cl. ............ 514/16.7; 514/16.8; 514/16.9; 514/21.2; 530/350; 435/69.1; 435/69.7

(58) Field of Classification Search ............ None
See application file for complete search history.

(56) References Cited

U.S. PATENT DOCUMENTS

| | | | |
|---|---|---|---|
| 5,194,596 A * | 3/1993 | Tischer et al. | 530/399 |
| 5,350,836 A * | 9/1994 | Kopchick et al. | 530/399 |
| 5,863,738 A | 1/1999 | Dijke et al. | |
| 6,207,814 B1 | 3/2001 | Miyazono et al. | |
| 6,248,554 B1 | 6/2001 | Cook et al. | |
| 6,610,513 B2 | 8/2003 | Wozney et al. | |
| 6,630,304 B1 | 10/2003 | Styrkarsdottir et al. | |
| 6,632,618 B1 | 10/2003 | Dijke et al. | |
| 6,770,626 B2 | 8/2004 | Ben-Sasson | |
| 7,067,260 B2 | 6/2006 | Dijke et al. | |
| 7,091,007 B2 | 8/2006 | Wozney et al. | |

FOREIGN PATENT DOCUMENTS

| | | |
|---|---|---|
| WO | WO 94/11502 A2 | 5/1994 |
| WO | WO 95/07982 A1 | 3/1995 |
| WO | WO 95/14778 A2 | 6/1995 |
| WO | WO 95/30003 A2 | 11/1995 |
| WO | WO 95/33058 A1 | 12/1995 |
| WO | WO-9723613 A2 | 7/1997 |
| WO | WO 00/18895 A1 | 4/2000 |
| WO | WO 01/53455 A2 | 7/2001 |
| WO | WO 02/22871 A2 | 3/2002 |
| WO | WO-02094852 A2 | 11/2002 |

(Continued)

OTHER PUBLICATIONS

Benjamin et al., 1998, Development 125:1591-1598; see Abstract and pp. 1594-1596.*

(Continued)

Primary Examiner — Elizabeth C Kemmerer
(74) Attorney, Agent, or Firm — Ropes & Gray LLP

(57) ABSTRACT

In certain aspects, the present invention provides compositions and methods for promoting bone growth and increasing bone density and strength. In certain embodiments, the present invention provides ALK3 polypeptides, including ALK3-Fc fusion proteins.

21 Claims, 38 Drawing Sheets

Whole-Body Bone Mineral Density

FOREIGN PATENT DOCUMENTS

| | | |
|---|---|---|
| WO | WO-2005003158 A2 | 1/2005 |
| WO | WO-2005014650 A2 | 2/2005 |
| WO | WO-2007038703 A2 | 4/2007 |
| WO | WO-2007062188 A2 | 5/2007 |
| WO | WO-2008072723 A1 | 6/2008 |
| WO | WO-2009025651 A1 | 2/2009 |

OTHER PUBLICATIONS

Vukicevic et al. (1996, PNAS USA 93:9021-9026).*
Shen et al. (2004, Eur. J. Neurosci. 20:2031-2037).*
Massague, 1987, Cell 49:437-8.*
Pilbeam et al., 1993, Bone 14:717-720.*
Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Winkler et al. (2005, J. Biol. Chem. 280:2498-2502).*
R&D product description page for BMPR1A-Fc (http://www.rndsystems.com/pdf/315-br.pdf; accessed Mar. 19, 2012).*
International Search Report for PCT/US2010/029282, dated Jun. 11, 2010.
Gilchrist, A., et al., "Antagonists of the receptor-G protein interface block Gi- coupled signal transduction", Journal of Biological Chemistry, 273(24):14912-14919, Jun. 12, 1998.
Natsume, T., et al., Interaction between Soluble Type I Receptor for Bone Morphogenetic Protein and Bone Morphogenetic Protein-4, The Journal of Biological Chemistry, 272(17):11535-11540 (1997).

* cited by examiner

FIGURE 1. Amino acid sequence for native human ALK3 precursor

```
  1  mpqlyiyirl lgaylfiisr vqgqnldsml hgtgmksdsd qkksengvtl apedtlpflk
 61  cycsghcpdd ainntcitng hcfaiieedd qgettlasgc mkyegsdfqc kdspkaqlrr
121  tieccrtnlc nqylqptlpp vvigpffdgs irwlvllism avciiamiif sscfcykhyc
181  ksissrrryn rdleqdeafi pvgeslkdli dqsqssgsgs glpllvqrti akqiqmvrqv
241  gkgrygevwm gkwrgekvav kvffteeas wfreteiyqt vlmrhenilg fiaadikgtg
301  swtqlylitd yhengslydf lkcatldtra llklaysaac glchlhteiy gtqgkpaiah
361  rdlksknili kkngscciad lglavkfnsd tnevdvplnt rvgtkrymap evldeslnkn
421  hfqpyimadi ysfgliiwem arrcitggiv eeyqlpyynm vpsdpsyedm revvcvkrlr
481  pivsnrwnsd eclravlklm secwahnpas rltalrikkt lakmvesqdv ki
     (SEQ ID NO: 1)
```

FIGURE 2. Native nucleotide sequence for human ALK3 precursor protein

```
   1 atgcctcagc tatacattta catcagatta ttgggagcct atttgttcat catttctcgt
  61 gttcaaggac agaatctgga tagtatgctt catggcactg ggatgaaatc agactccgac
 121 cagaaaaagt cagaaaatgg agtaacctta gcaccagagg ataccttgcc ttttttaaag
 181 tgctattgct cagggcactg tccagatgat gctattaata acacatgcat aactaatgga
 241 cattgctttg ccatcataga agaagatgac cagggagaaa ccacattagc ttcagggtgt
 301 atgaaatatg aaggatctga ttttcagtgc aaagattctc aaaagccca gctacgccgg
 361 acaatagaat gttgtcggac caatttatgt aaccagtatt gcaacccac actgccccct
 421 gttgtcatag gtccgttttt tgatggcagc attcgatggc tggttttgct catttctatg
 481 gctgtctgca taattgctat gatcatcttc tccagctgct tttgttacaa acattattgc
 541 aagagcatct caagcagacg tcgttacaat cgtgatttgg aacaggatga agcatttatt
 601 ccagttggag aatcactaaa agaccttatt gaccagtcac aaagttctgg tagtgggtct
 661 ggactacctt tattggttca gcgaactatt gccaacaga ttcagatggt ccggcaagtt
 721 ggtaaaggcc gatatggaga agtatggatg ggcaaatggc gtggcgaaaa agtggcggtg
 781 aaagtattct ttaccactga agaagccagc tggtttcgag aaacagaaat ctaccaaact
 841 gtgctaatgc gccatgaaaa catacttggt tcatagcgg cagacattaa aggtacaggt
 901 tcctggactc agctctattt gattactgat taccatgaaa atggatctct ctatgacttc
 961 ctgaaatgtg ctacactgga caccagagcc ctgcttaaat tggcttattc agctgcctgt
1021 ggtctgtgcc acctgcacac agaaatttat ggcacccaag gaaagcccgc aattgctcat
1081 cgagacctaa agagcaaaaa catcctcatc aagaaaatg ggagttgctg cattgctgac
1141 ctgggccttg ctgttaaatt caacagtgac acaaatgaag ttgatgtgcc cttgaatacc
1201 agggtgggca ccaaacgcta catggctccc gaagtgctgg acgaaagcct gaacaaaaac
1261 cacttccagc cctacatcat ggctgacatc tacagcttcg gcctaatcat tgggagatg
1321 gctcgtcgtt gtatcacagg agggatcgtg gaagaatacc aattgccata ttacaacatg
1381 gtaccgagtg atccgtcata cgaagatatg cgtgaggttg tgtgtgtcaa acgtttgcgg
1441 ccaattgtgt ctaatcggtg aacagtgat gaatgtctac gagcagtttt gaagctaatg
1501 tcagaatgct gggcccacaa tccagcctcc agactcacag cattgagaat taagaagacg
1561 cttgccaaga tggttgaatc ccaagatgta aaaatc       (SEQ ID NO: 2)
```

FIGURE 3. Amino acid sequence for native human ALK3 ECD

```
  1  qnldsmlhgt gmksdsdgkk sengvtlape dtlpflkcyc sghcpddain ntcitnghcf
 61  aiieeddqge ttlasgcmky egsdfqckds pkaqlrrtie ccrtnlcnqy lqptlppvvi
121  gpffdgsir  (SEQ ID NO: 3)
```

FIGURE 4. Native nucleotide sequence for human ALK3 ECD

```
  1  cagaatctgg atagtatgct tcatggcact gggatgaaat cagactccga ccagaaaaag
 61  tcagaaaatg gagtaacctt agcaccagag gatacctcgc ctttttaaa gtgctattgc
121  tcagggcact gtccagatga tgctattaat aacacatgca taactaatgg acattgcttt
181  gccatcatag aagaagatga ccagggagaa accacattag cttcagggtg tatgaaatat
241  gaaggatctg attttcagtg caaagattct ccaaaagccc agctacgccg acaatagaa
301  tgttgtcgga ccaatttatg taaccagtat ttgcaaccca cactgccccc tgttgtcata
361  ggtccgtttt ttgatggcag cattcga    (SEQ ID NO: 4)
```

FIGURE 5. Amino acid sequence for native human Fc domain

```
  1  THTCPPCPAP  ELLGGPSVFL  FPPKPKDTLM  ISRTPEVTCV  VVDVSHEDPE
 51  VKFNWYVDGV  EVHNAKTKPR  EEQYNSTYRV  VSVLTVLHQD  WLNGKEYKCK
101  VSNKALPAPI  EKTISKAKGQ  PREPQVYTLP  PSREEMTKNQ  VSLTCLVKGF
151  YPSDIAVEWE  SNGQPENNYK  TTPPVLDSDG  SFFLYSKLTV  DKSRWQQGNV
201  FSCSVMHEAL  HNHYTQKSLS  LSPGK  (SEQ ID NO: 5)
```

FIGURE 6. Native nucleotide sequence for human Fc domain

```
  1  ACTCACACAT GCCCACCGTG CCCAGCACCT GAACTCCTGG GGGGACCGTC AGTCTTCCTC
 61  TTCCCCCCAA AACCCAAGGA CACCCTCATG ATCTCCCGGA CCCCTGAGGT CACATGCGTG
121  GTGGTGGACG TGAGCCACGA AGACCCTGAG GTCAAGTTCA ACTGGTACGT GGACGGCGTG
181  GAGGTGCATA ATGCCAAGAC AAAGCCGCGG GAGGAGCAGT ACAACAGCAC GTACCGTGTG
241  GTCAGCGTCC TCACCGTCCT GCACCAGGAC TGGCTGAATG GCAAGGAGTA CAAGTGCAAG
301  GTCTCCAACA AAGCCCTCCC AGCCCCCATC GAGAAAACCA TCTCCAAAGC CAAAGGGCAG
361  CCCCGAGAAC CACAGGTGTA CACCCTGCCC CCATCCCGGG AGGAGATGAC CAAGAACCAG
421  GTCAGCCTGA CCTGCCTGGT CAAAGGCTTC TATCCCAGCG ACATCGCCGT GGAGTGGGAG
481  AGCAATGGGC AGCCGGAGAA CAACTACAAG ACCACGCCTC CCGTGCTGGA CTCCGACGGC
541  TCCTTCTTCC TCTATAGCAA GCTCACCGTG GACAAGAGCA GGTGGCAGCA GGGGAACGTC
601  TTCTCATGCT CCGTGATGCA TGAGGCTCTG CACAACCACT ACACGCAGAA GAGCCTCTCC
661  CTGTCCCCGG GTAAATGA   (SEQ ID NO: 6)
```

FIGURE 7. Amino acid sequence for leaderless hALK(24-152)-hFc

```
  1  QNLDSMLHGT GMKSDSDQKK SENGVTLAPE DTLPFLKCYC SGHCPDDAIN
 51  NTCITNGHCF AIIEEDDQGE TTLASGCMKY EGSDFQCKDS PKAQLRRTIE
101  CCRTNLCNQY LQPTLPPVVI GPFFDGSIRT GGGTHTCPPC PAPELLGGPS
151  VFLFPPKPKD TLMISRTPEV TCVVVDVSHE DPEVKFNWYV DGVEVHNAKT
201  KPREEQYNST YRVVSVLTVL HQDWLNGKEY KCKVSNKALP APIEKTISKA
251  KGQPREPQVY TLPPSREEMT KNQVSLTCLV KGFYPSDIAV EWESNGQPEN
301  NYKTTPPVLD SDGSFFLYSK LTVDKSRWQQ GNVFSCSVMH EALHNHYTQK
351  SLSLSPGK (SEQ ID NO: 7)
```

FIGURE 8. Amino acid sequence for TPA-hALK3(24-152)-hFc

```
  1  MDAMKRGLCC VLLLCGAVFV SPGAQNLDSM LHGTGMKSDS DQKKSENGVT
 51  LAPEDTLPFL KCYCSGHCPD DAINNTCITN GHCFAIIEED DQGETTLASG
101  CMKYEGSDFQ CKDSPKAQLR RTIECCRTNL CNQYLQPTLP PVVIGPFFDG
151  SIRTGGGTHT CPPCPAPELL GGPSVFLFPP KPKDTLMISR TPEVTCVVVD
201  VSHEDPEVKF NWYVDGVEVH NAKTKPREEQ YNSTYRVVSV LTVLHQDWLN
251  GKEYKCKVSN KALPAPIEKT ISKAKGQPRE PQVYTLPPSR EEMTKNQVSL
301  TCLVKGFYPS DIAVEWESNG QPENNYKTTP PVLDSDGSFF LYSKLTVDKS
351  RWQQGNVFSC SVMHEALHNH YTQKSLSLSP GK (SEQ ID NO: 11)
```

FIGURE 9. A nucleotide sequence for TPA-hALK3(24-152)-hFc

```
  1   ATGGATGCAA TGAAGAGAGG GCTCTGCTGT GTGCTGCTGC TGTGTGGAGC AGTCTTCGTT
      TACCTACGTT ACTTCTCTCC CGAGACGACA CACGACGACG ACACACCTCG TCAGAAGCAA

61   TCGCCCGGCG CCCAGAATCT GGATAGTATG CTTCATGGCA CTGGGATGAA ATCAGACTCC
      AGCGGGCCGC GGGTCTTAGA CCTATCATAC GAAGTACCGT GACCCTACTT TAGTCTGAGG

121   GACCAGAAAA AGTCAGAAAA TGGAGTAACC TTAGCACCAG AGGATACCTT GCCTTTTTTA
      CTGGTCTTTT TCAGTCTTTT ACCTCATTGG AATCGTGGTC TCCTATGGAA CGGAAAAAAT

181   AAGTGCTATT GCTCAGGGCA CTGTCCAGAT GATGCTATTA ATAACACATG CATAACTAAT
      TTCACGATAA CGAGTCCCGT GACAGGTCTA CTACGATAAT TATTGTGTAC GTATTGATTA

241   GGACATTGCT TTGCCATCAT AGAAGAAGAT GACCAGGGAG AAACCACATT AGCTTCAGGG
      CCTGTAACGA AACGGTAGTA TCTTCTTCTA CTGGTCCCTC TTTGGTGTAA TCGAAGTCCC

301   TGTATGAAAT ATGAAGGATC TGATTTTCAG TGCAAAGATT CTCCAAAAGC CCAGCTACGC
      ACATACTTTA TACTTCCTAG ACTAAAAGTC ACGTTTCTAA GAGGTTTTCG GGTCGATGCG

361   CGGACAATAG AATGTTGTCG GACCAATTTA TGTAACCAGT ATTTGCAACC CACACTGCCC
      GCCTGTTATC TTACAACAGC CTGGTTAAAT ACATTGGTCA TAAACGTTGG GTGTGACGGG

421   CCTGTTGTCA TAGGTCCGTT TTTTGATGGC AGCATTCGAA CCGGTGGGGG TACTCACACA
      GGACAACAGT ATCCAGGCAA AAAACTACCG TCGTAAGCTT GGCCACCCCC ATGAGTGTGT

481   TGCCCACCGT GCCCAGCACC TGAACTCCTG GGGGGACCGT CAGTCTTCCT CTTCCCCCCA
      ACGGGTGGCA CGGGTCGTGG ACTTGAGGAC CCCCCTGGCA GTCAGAAGGA GAAGGGGGGT

541   AAACCCAAGG ACACCCTCAT GATCTCCCGG ACCCCTGAGG TCACATGCGT GGTGGTGGAC
      TTTGGGTTCC TGTGGGAGTA CTAGAGGGCC TGGGGACTCC AGTGTACGCA CCACCACCTG

601   GTGAGCCACG AAGACCCTGA GGTCAAGTTC AACTGGTACG TGGACGGCGT GGAGGTGCAT
      CACTCGGTGC TTCTGGGACT CCAGTTCAAG TTGACCATGC ACCTGCCGCA CCTCCACGTA

661   AATGCCAAGA CAAAGCCGCG GGAGGAGCAG TACAACAGCA CGTACCGTGT GGTCAGCGTC
      TTACGGTTCT GTTTCGGCGC CCTCCTCGTC ATGTTGTCGT GCATGGCACA CCAGTCGCAG

721   CTCACCGTCC TGCACCAGGA CTGGCTGAAT GGCAAGGAGT ACAAGTGCAA GGTCTCCAAC
      GAGTGGCAGG ACGTGGTCCT GACCGACTTA CCGTTCCTCA TGTTCACGTT CCAGAGGTTG

781   AAAGCCCTCC CAGCCCCCAT CGAGAAAACC ATCTCCAAAG CCAAAGGGCA GCCCCGAGAA
      TTTCGGGAGG GTCGGGGGTA GCTCTTTTGG TAGAGGTTTC GGTTTCCCGT CGGGGCTCTT

841   CCACAGGTGT ACACCCTGCC CCCATCCCGG GAGGAGATGA CCAAGAACCA GGTCAGCCTG
      GGTGTCCACA TGTGGGACGG GGGTAGGGCC CTCCTCTACT GGTTCTTGGT CCAGTCGGAC
```

FIGURE 9 con't. A nucleotide sequence for TPA-hALK3(24-152)-hFc

```
 901    ACCTGCCTGG TCAAAGGCTT CTATCCCAGC GACATCGCCG TGGAGTGGGA GAGCAATGGG
        TGGACGGACC AGTTTCCGAA GATAGGGTCG CTGTAGCGGC ACCTCACCCT CTCGTTACCC

961    CAGCCGGAGA ACAACTACAA GACCACGCCT CCCGTGCTGG ACTCCGACGG CTCCTTCTTC
        GTCGGCCTCT TGTTGATGTT CTGGTGCGGA GGGCACGACC TGAGGCTGCC GAGGAAGAAG

1021    CTCTATAGCA AGCTCACCGT GGACAAGAGC AGGTGGCAGC AGGGGAACGT CTTCTCATGC
        GAGATATCGT TCGAGTGGCA CCTGTTCTCG TCCACCGTCG TCCCCTTGCA GAAGAGTACG

1081    TCCGTGATGC ATGAGGCTCT GCACAACCAC TACACGCAGA AGAGCCTCTC CCTGTCCCCG
        AGGCACTACG TACTCCGAGA CGTGTTGGTG ATGTGCGTCT TCTCGGAGAG GGACAGGGGC

1141    GGTAAA    (Sense strand - SEQ ID NO: 12)
        CCATTT    (Antisense strand - SEQ ID NO: 13)
```

FIGURE 10. Amino acid sequence for TPA-hALK3(24-152)-mFc

```
  1  MDAMKRGLCC VLLLCGAVFV SPGAQNLDSM LHGTGMKSDS DQKKSENGVT
 51  LAPEDTLPFL KCYCSGHCPD DAINNTCITN GHCFAIIEED DQGETTLASG
101  CMKYEGSDFQ CKDSPKAQLR RTIECCRTNL CNQYLQPTLP PVVIGPFFDG
151  SIRTGGGEPR VPITQNPCPP LKECPPCAAP DLLGGPSVFI FPPKIKDVLM
201  ISLSPMVTCV VVDVSEDDPD VQISWFVNNV EVHTAQTQTH REDYNSTLRV
251  VSALPIQHQD WMSGKEFKCK VNNRALPSPI EKTISKPRGP VRAPQVYVLP
301  PPAEEMTKKE FSLTCMITGF LPAEIAVDWT SNGRTEQNYK NTATVLDSDG
351  SYFMYSKLRV QKSTWERGSL FACSVVHEGL HNHLTTKTIS RSLGK
     (SEQ ID NO: 14)
```

FIGURE 11. A nucleotide sequence for TPA-hALK3(24-152)-mFc

```
   1  ATGGATGCAA TGAAGAGAGG GCTCTGCTGT GTGCTGCTGC TGTGTGGAGC AGTCTTCGTT
      TACCTACGTT ACTTCTCTCC CGAGACGACA CACGACGACG ACACACCTCG TCAGAAGCAA

61  TCGCCCGGCG CCCAGAATCT GGATAGTATG CTTCATGGCA CTGGGATGAA ATCAGACTCC
      AGCGGGCCGC GGGTCTTAGA CCTATCATAC GAAGTACCGT GACCCTACTT TAGTCTGAGG

121  GACCAGAAAA AGTCAGAAAA TGGAGTAACC TTAGCACCAG AGGATACCTT GCCTTTTTA
      CTGGTCTTTT TCAGTCTTTT ACCTCATTGG AATCGTGGTC TCCTATGGAA CGGAAAAAAT

181  AAGTGCTATT GCTCAGGGCA CTGTCCAGAT GATGCTATTA ATAACACATG CATAACTAAT
      TTCACGATAA CGAGTCCCGT GACAGGTCTA CTACGATAAT TATTGTGTAC GTATTGATTA

241  GGACATTGCT TTGCCATCAT AGAAGAAGAT GACCAGGGAG AAACCACATT AGCTTCAGGG
      CCTGTAACGA AACGGTAGTA TCTTCTTCTA CTGGTCCCTC TTTGGTGTAA TCGAAGTCCC

301  TGTATGAAAT ATGAAGGATC TGATTTTCAG TGCAAAGATT CTCCAAAAGC CCAGCTACGC
      ACATACTTTA TACTTCCTAG ACTAAAAGTC ACGTTTCTAA GAGGTTTTCG GGTCGATGCG

361  CGGACAATAG AATGTTGTCG GACCAATTTA TGTAACCAGT ATTTGCAACC CACACTGCCC
      GCCTGTTATC TTACAACAGC CTGGTTAAAT ACATTGGTCA TAAACGTTGG GTGTGACGGG

421  CCTGTTGTCA TAGGTCCGTT TTTTGATGGC AGCATTCGAA CCGGTGGGGG TGAGCCCAGA
      GGACAACAGT ATCCAGGCAA AAACTACCG TCGTAAGCTT GGCCACCCCC ACTCGGGTCT

481  GTGCCCATAA CACAGAACCC CTGTCCTCCA CTCAAAGAGT GTCCCCCATG CGCAGCTCCA
      CACGGGTATT GTGTCTTGGG GACAGGAGGT GAGTTTCTCA CAGGGGGTAC GCGTCGAGGT

541  GACCTCTTGG GTGGACCATC CGTCTTCATC TTCCCTCCAA AGATCAAGGA TGTACTCATG
      CTGGAGAACC CACCTGGTAG GCAGAAGTAG AAGGGAGGTT TCTAGTTCCT ACATGAGTAC

601  ATCTCCCTGA GCCCCATGGT CACATGTGTG GTGGTGGATG TGAGCGAGGA TGACCCAGAC
      TAGAGGGACT CGGGGTACCA GTGTACACAC CACCACCTAC ACTCGCTCCT ACTGGGTCTG

661  GTCCAGATCA GCTGGTTTGT GAACAACGTG GAAGTACACA CAGCTCAGAC ACAAACCCAT
      CAGGTCTAGT CGACCAAACA CTTGTTGCAC CTTCATGTGT GTCGAGTCTG TGTTTGGGTA

721  AGAGAGGATT ACAACAGTAC TCTCCGGGTG GTCAGTGCCC TCCCCATCCA GCACCAGGAC
      TCTCTCCTAA TGTTGTCATG AGAGGCCCAC CAGTCACGGG AGGGGTAGGT CGTGGTCCTG

781  TGGATGAGTG GCAAGGAGTT CAAATGCAAG GTCAACAACA GAGCCCTCCC ATCCCCCATC
      ACCTACTCAC CGTTCCTCAA GTTTACGTTC CAGTTGTTGT CTCGGGAGGG TAGGGGGTAG

841  GAGAAAACCA TCTCAAAACC CAGAGGGCCA GTAAGAGCTC CACAGGTATA TGTCTTGCCT
      CTCTTTTGGT AGAGTTTTGG GTCTCCCGGT CATTCTCGAG GTGTCCATAT ACAGAACGGA

901  CCACCAGCAG AAGAGATGAC TAAGAAAGAG TTCAGTCTGA CCTGCATGAT CACAGGCTTC
      GGTGGTCGTC TTCTCTACTG ATTCTTTCTC AAGTCAGACT GGACGTACTA GTGTCCGAAG

961  TTACCTGCCG AAATTGCTGT GGACTGGACC AGCAATGGGC GTACAGAGCA AAACTACAAG
      AATGGACGGC TTTAACGACA CCTGACCTGG TCGTTACCCG CATGTCTCGT TTTGATGTTC

1021  AACACCGCAA CAGTCCTGGA CTCTGATGGT TCTTACTTCA TGTACAGCAA GCTCAGAGTA
      TTGTGGCGTT GTCAGGACCT GAGACTACCA AGAATGAAGT ACATGTCGTT CGAGTCTCAT

1081  CAAAAGAGCA CTTGGGAAAG AGGAAGTCTT TTCGCCTGCT CAGTGGTCCA CGAGGGTCTG
      GTTTTCTCGT GAACCCTTTC TCCTTCAGAA AAGCGGACGA GTCACCAGGT GCTCCCAGAC
```

FIGURE 11 con't.  A nucleotide sequence for TPA-hALK3(24-152)-mFc

```
1141   CACAATCACC TTACGACTAA GACCATCTCC CGGTCTCTGG GTAAA
       GTGTTAGTGG AATGCTGATT CTGGTAGAGG GCCAGAGACC CATTT (Sense strand - SEQ ID NO: 15)
       (Antisense strand - SEQ ID NO: 16)
```

FIGURE 17. Effect of ALK3-Fc on trabecular bone microarchitecture
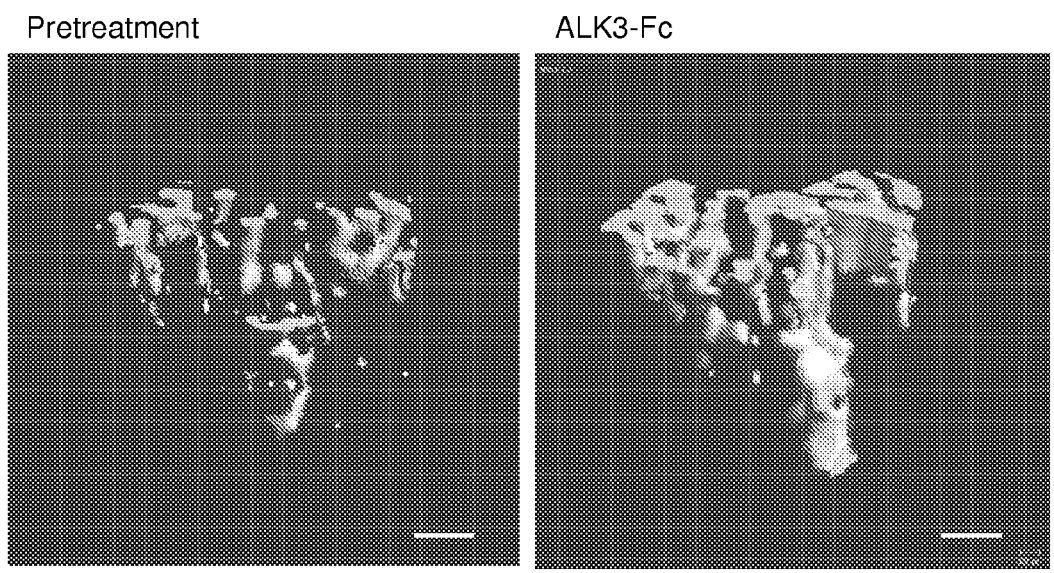

FIGURE 18. Approaches for interfering with BMP-ALK3 signaling
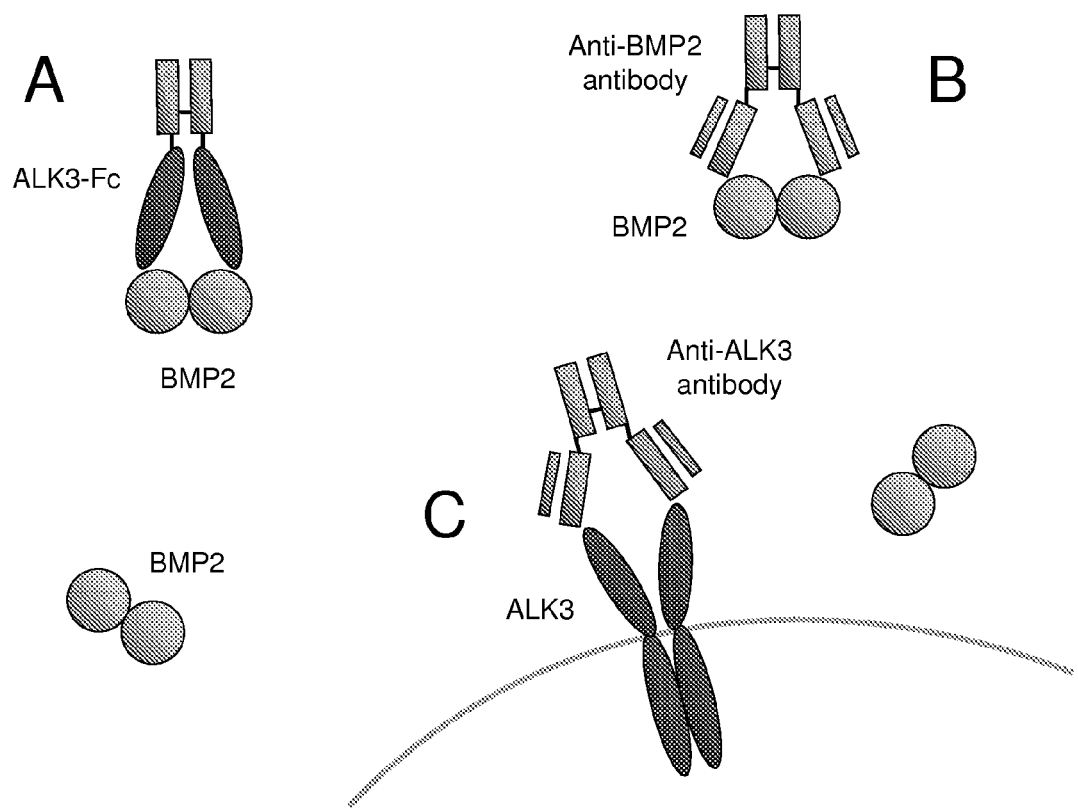

FIGURE 19. Effect of hALK3-mFc on maximum bone load
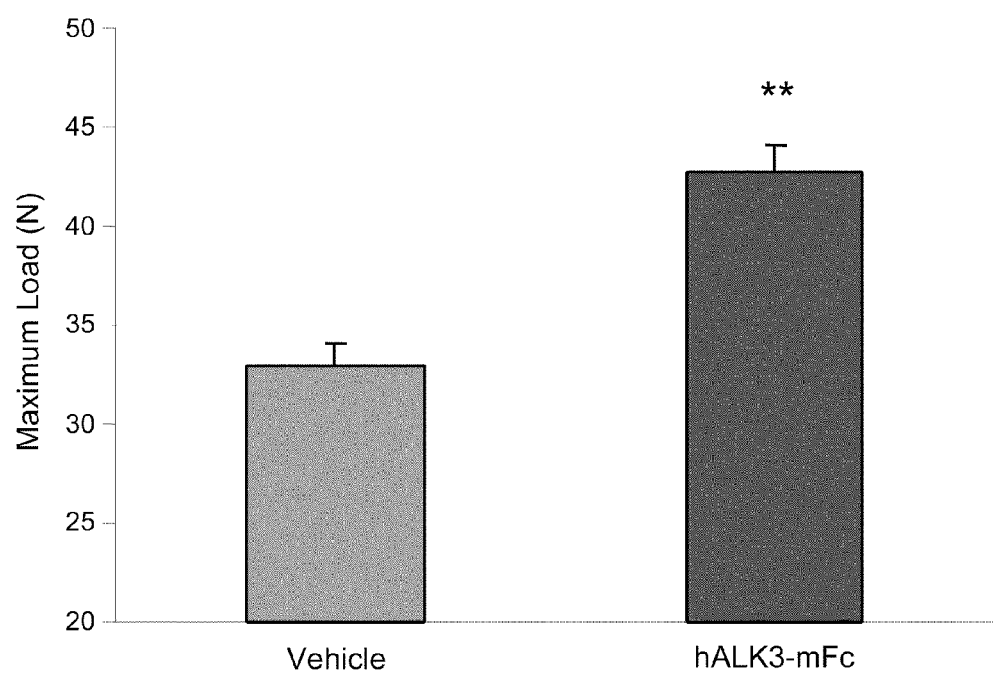

FIGURE 20. Effect of hALK3-mFc on bone stiffness
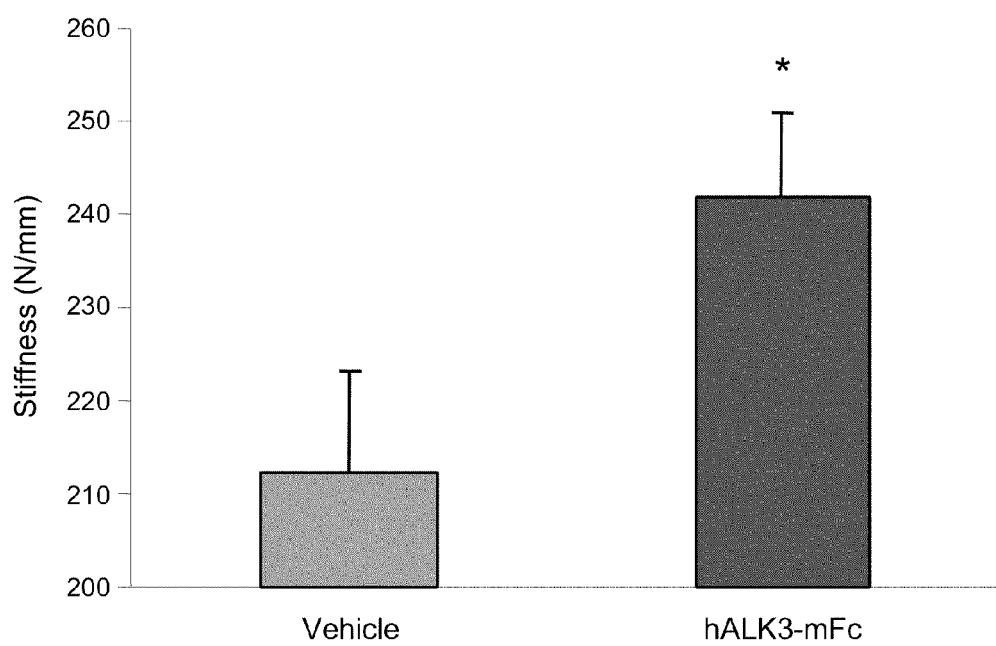

FIGURE 21. Effect of hALK3-mFc on energy to bone failure
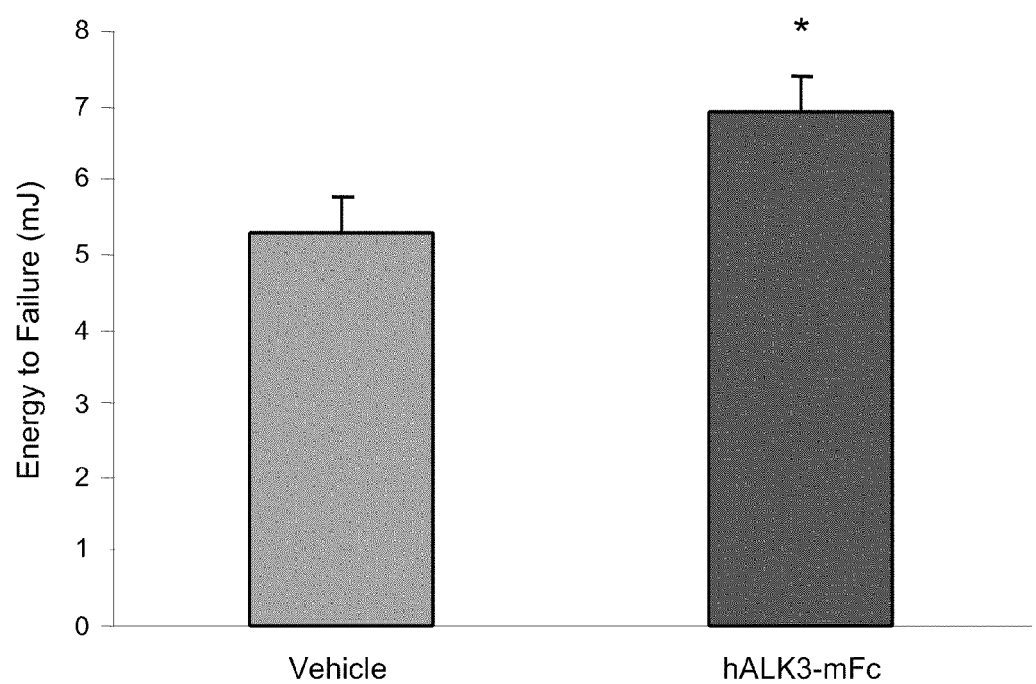

FIGURE 22. Effect of mALK3-mFc on trabecular bone volume in a mouse model of osteopenia
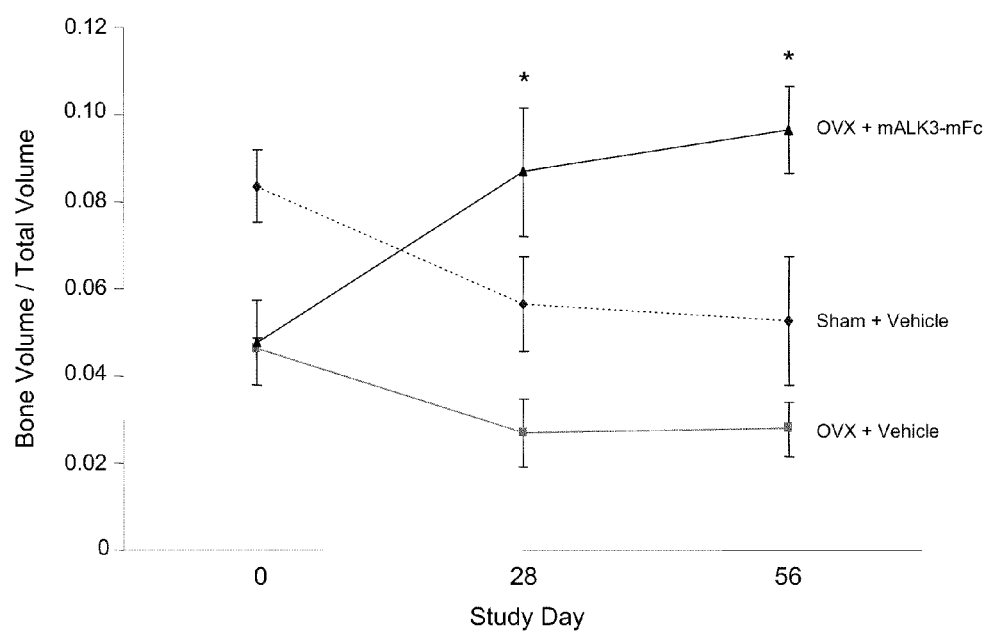

FIGURE 23. Effect of mALK3-mFc on cortical bone thickness in a mouse model of osteopenia
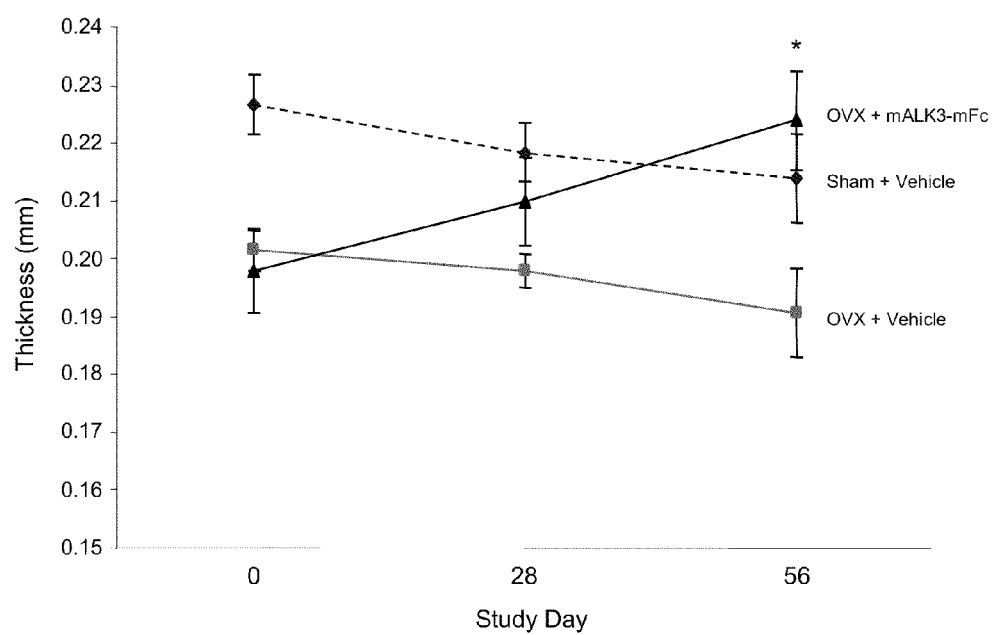

FIGURE 24. Effect of mALK3-mFc on endosteal circumference in a mouse model of osteopenia
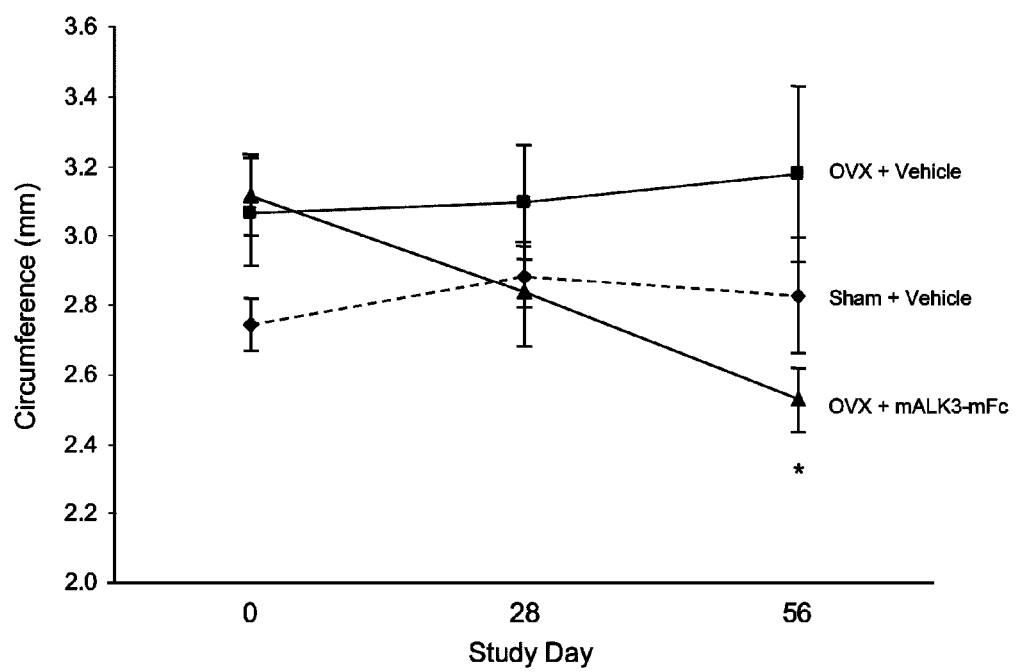

FIGURE 25. Effect of mALK3-mFc on whole-body bone mineral density in a mouse model of osteopenia
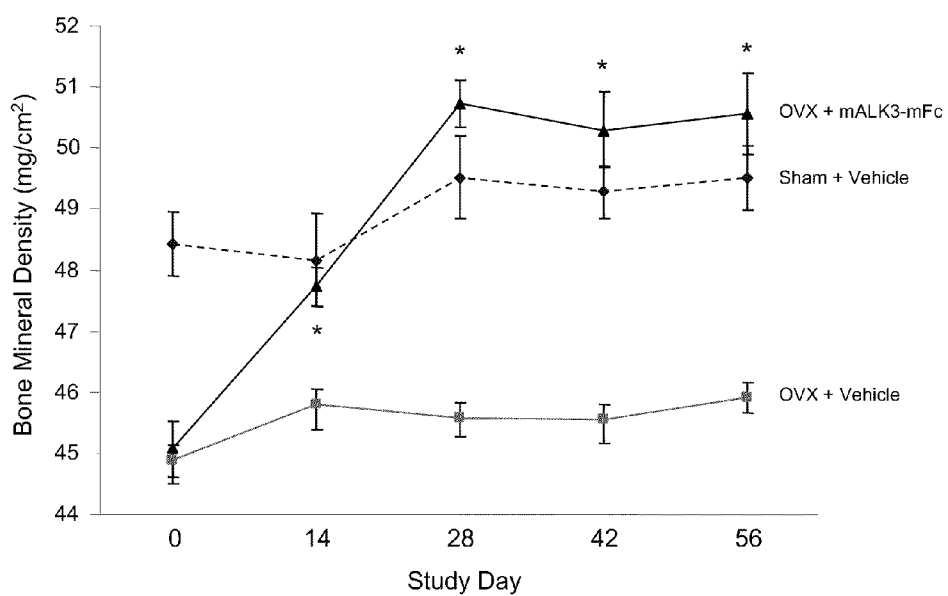

FIGURE 26. Effect of mALK3-mFc on vertebral bone mineral density in a mouse model of osteopenia
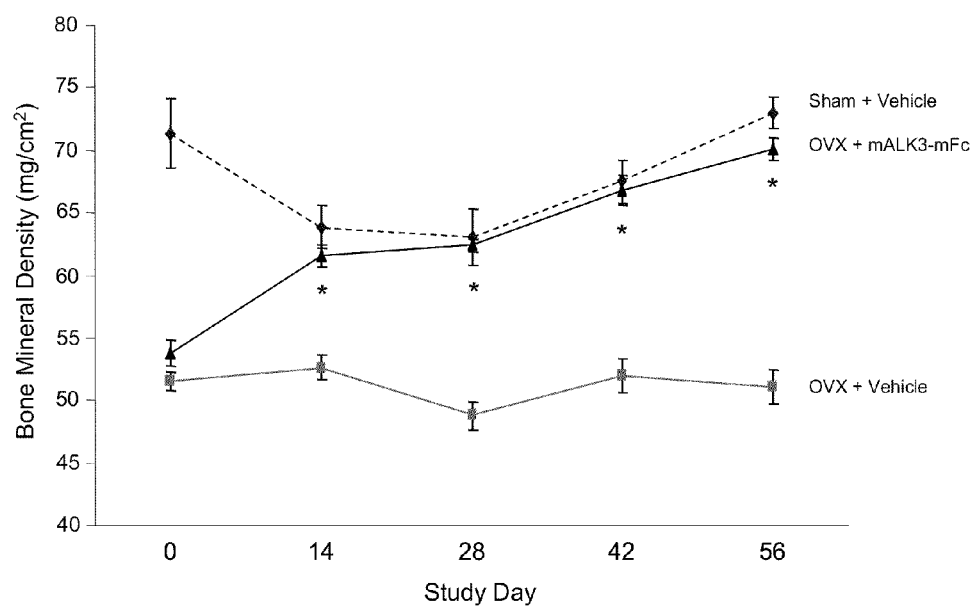

FIGURE 27. Effect of mALK3-mFc on femoral-tibial bone mineral density in a mouse model of osteopenia
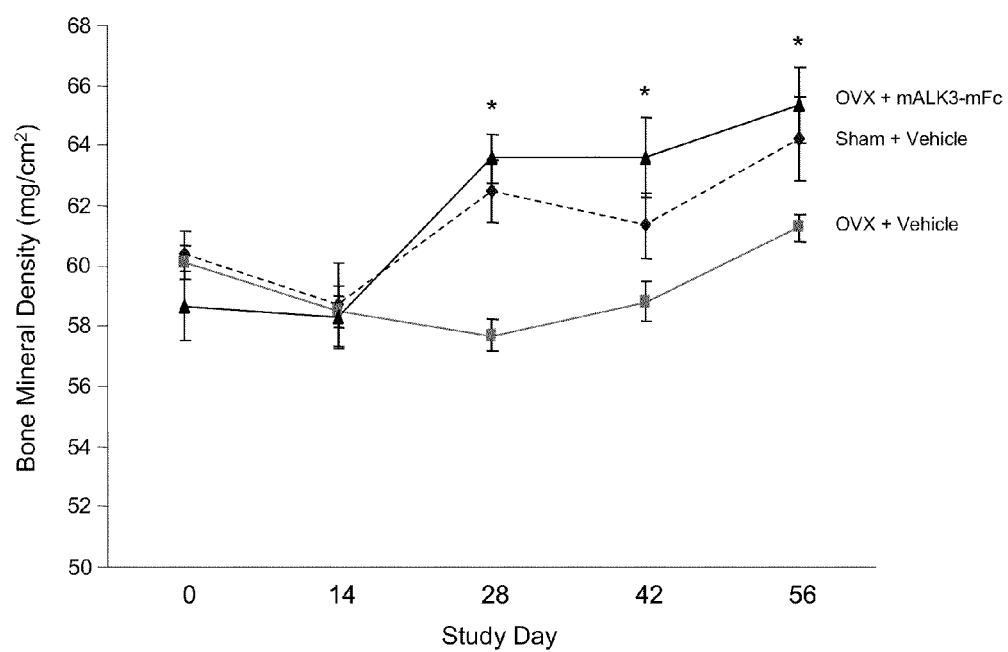

FIGURE 28. Effect of mALK3-mFc on vertebral bone microarchitecture in a mouse model of osteopenia
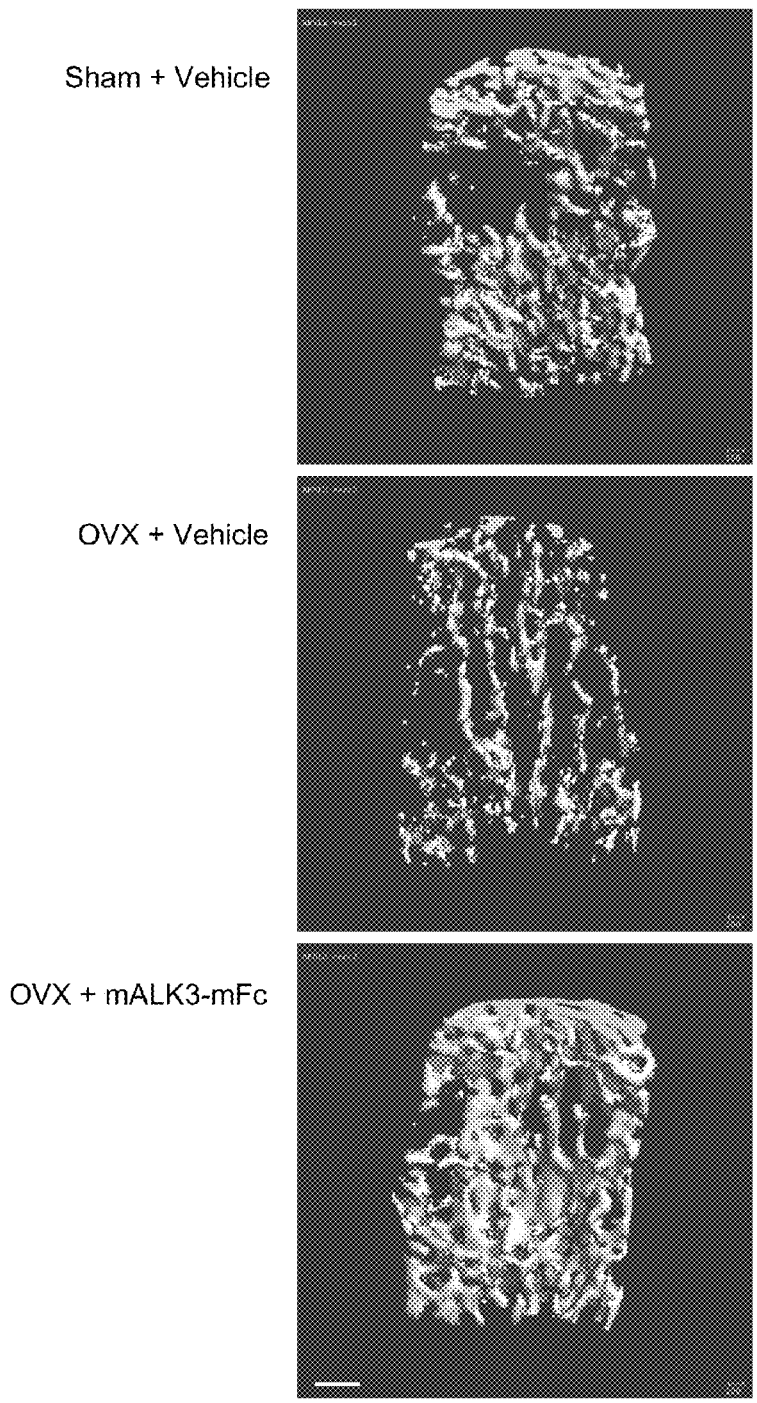

FIGURE 29. Effect of mALK3-mFc on bone volume assessed by histomorphometry in mice
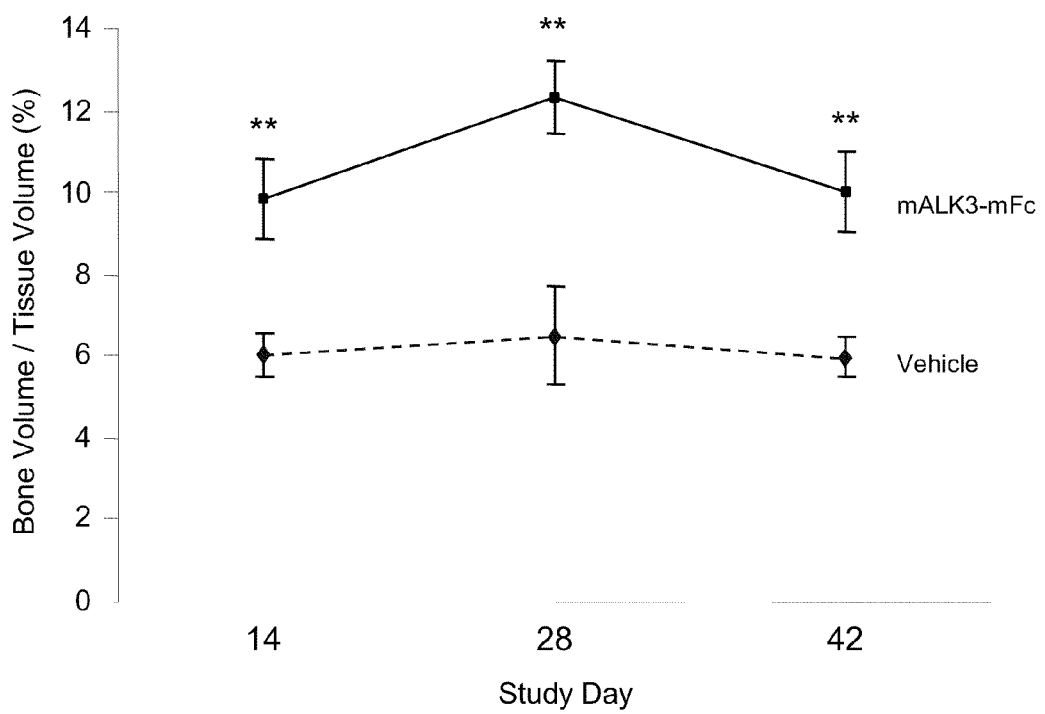

FIGURE 30. Effect of mALK3-mFc on bone formation rate assessed by histomorphometry in mice
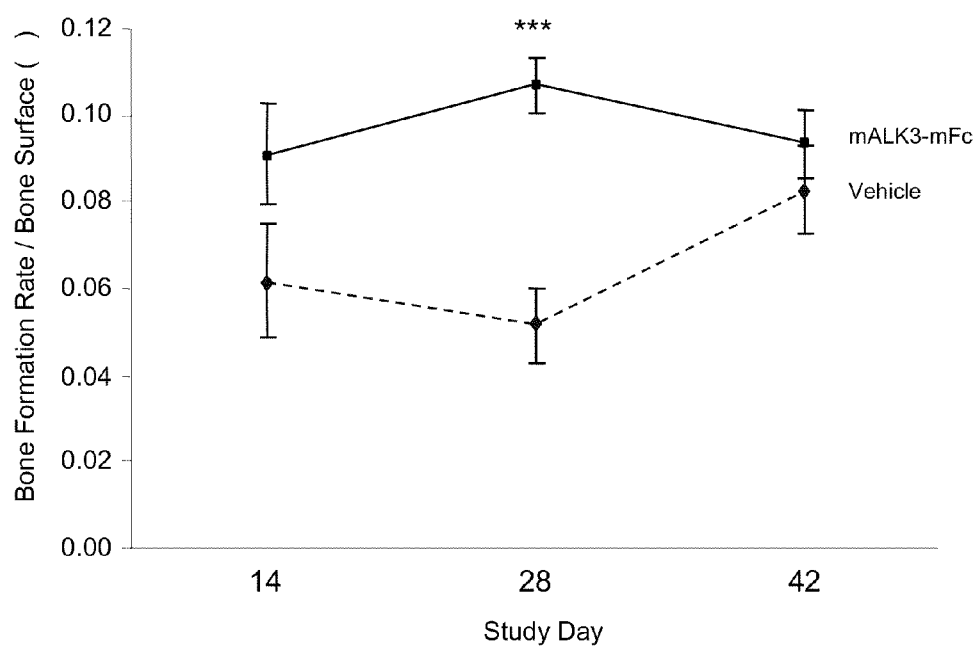

FIGURE 31. Effect of mALK3-mFc on bone mineralizing surface assessed by histomorphometry in mice
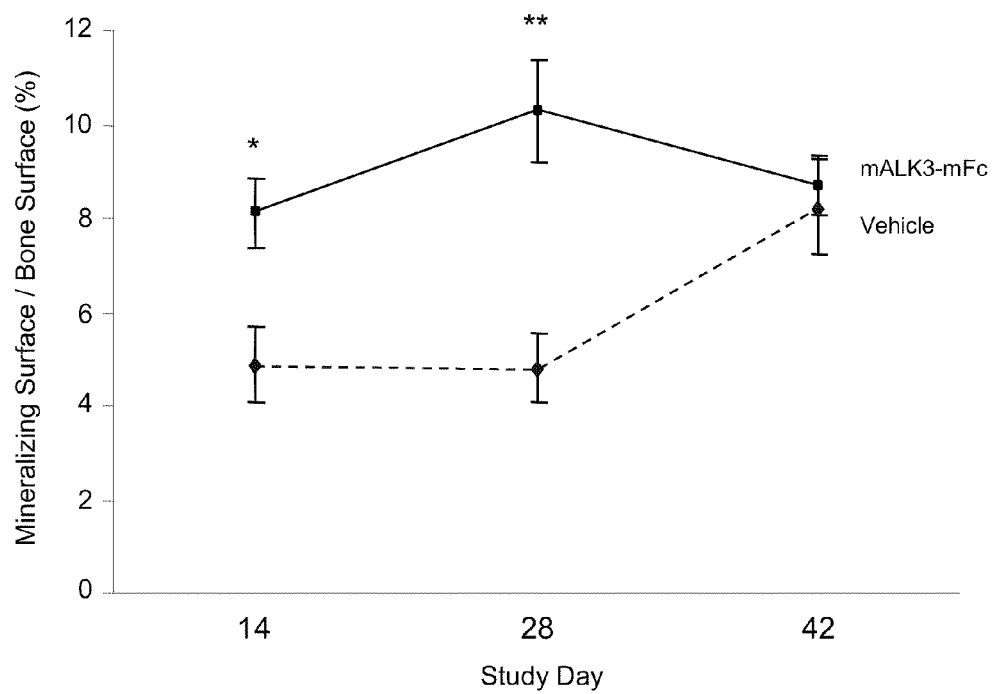

FIGURE 32. Effect of mALK3-mFc on osteoclast surface assessed by histomorphometry in mice
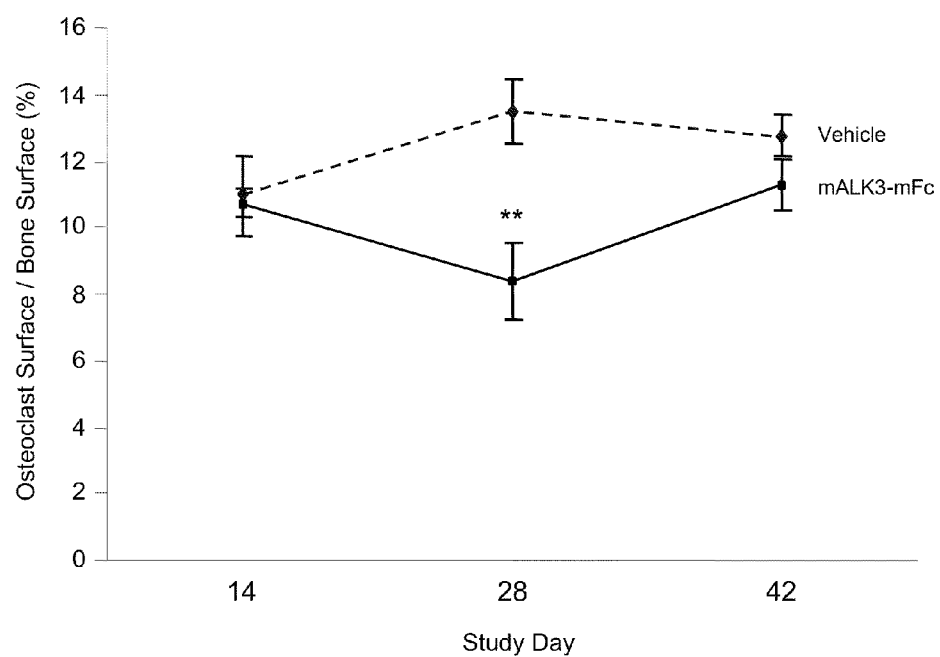

FIGURE 33. Effect of mALK3-mFc on serum RANKL levels in mice
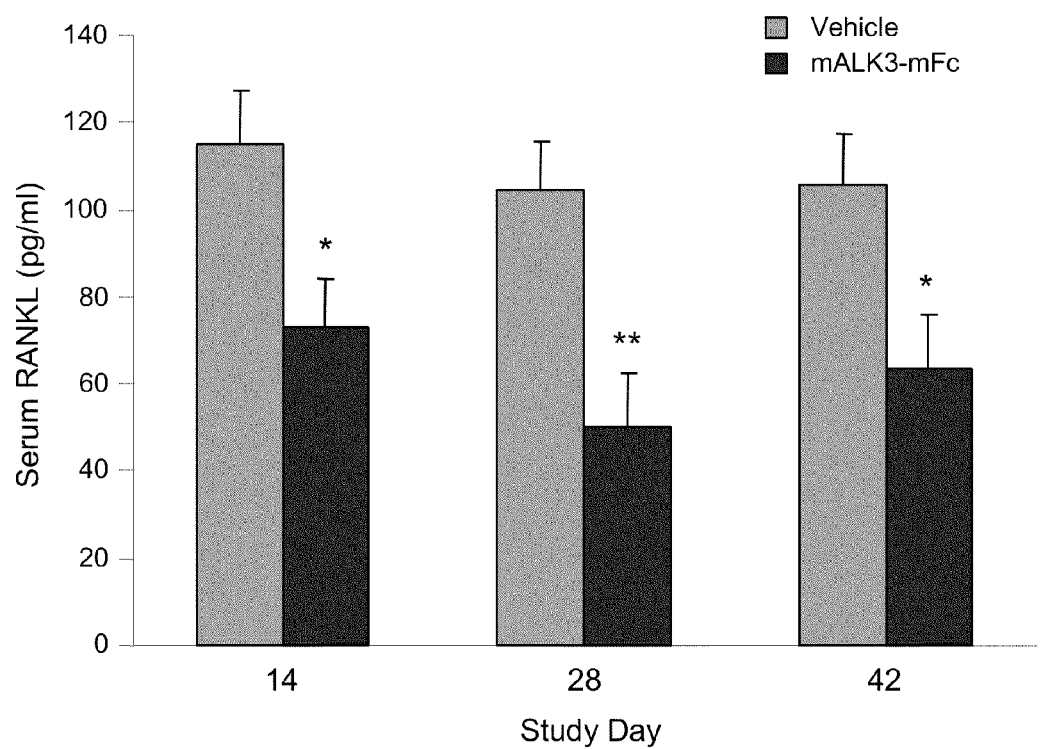

FIGURE 34. Effect of mALK3-mFc on serum osteoprotegerin levels in mice
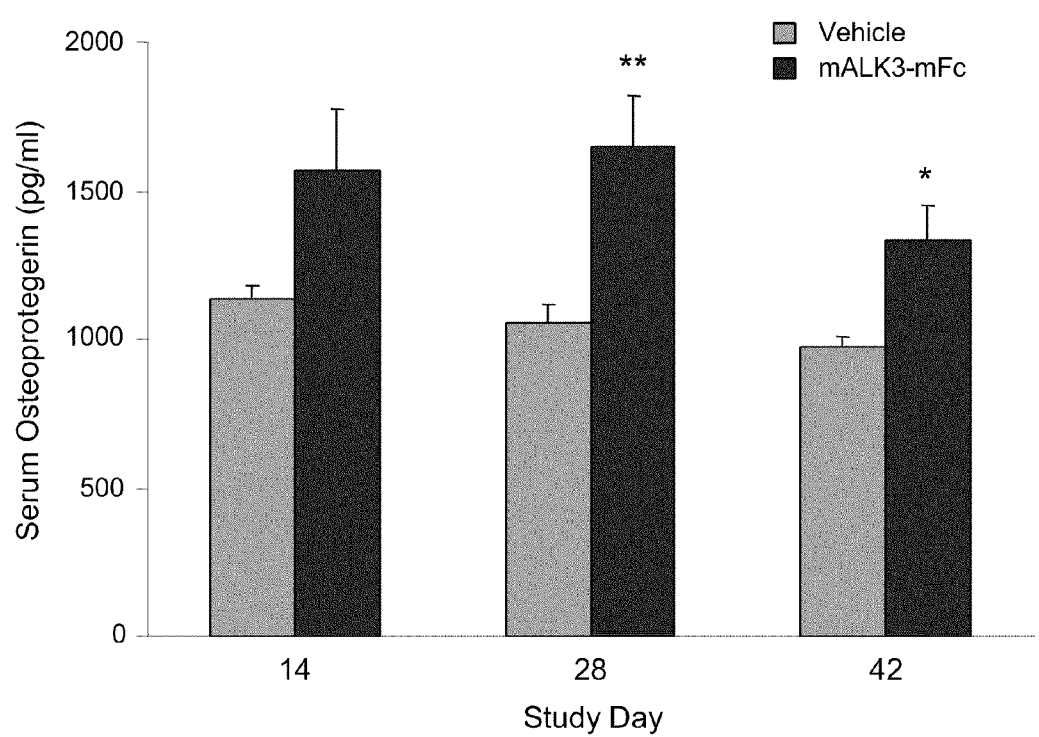

FIGURE 35. Effect of mALK3-mFc on bone sclerostin mRNA levels in mice
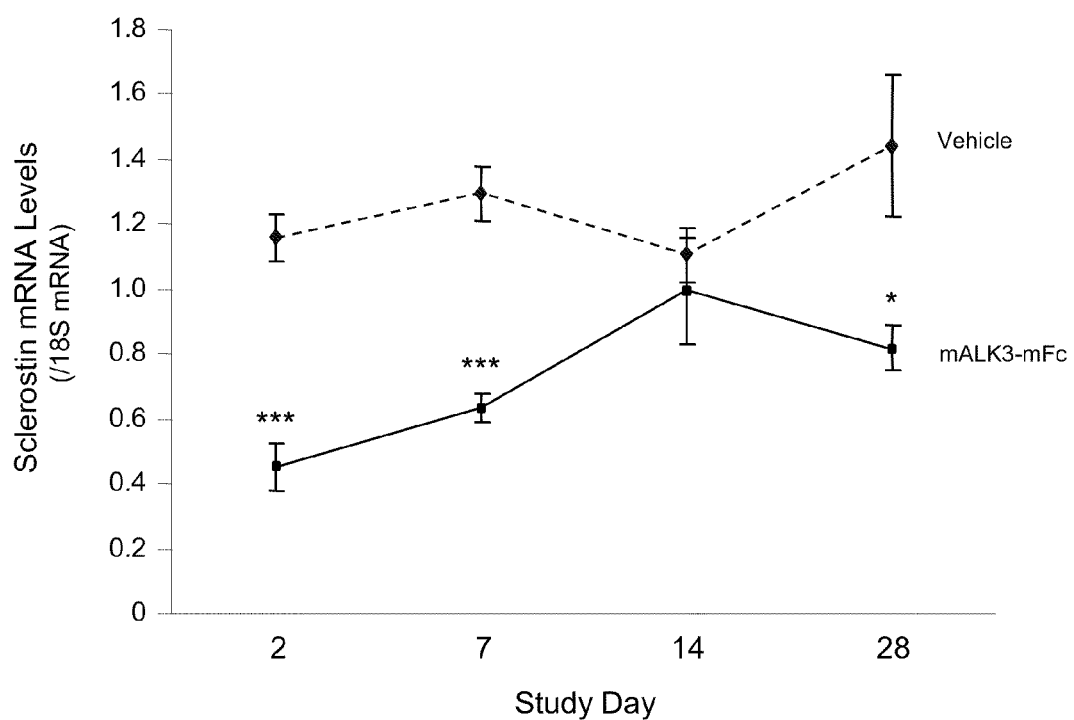

FIGURE 36. Effect of hALK3-hFc on trabecular bone volume in mice
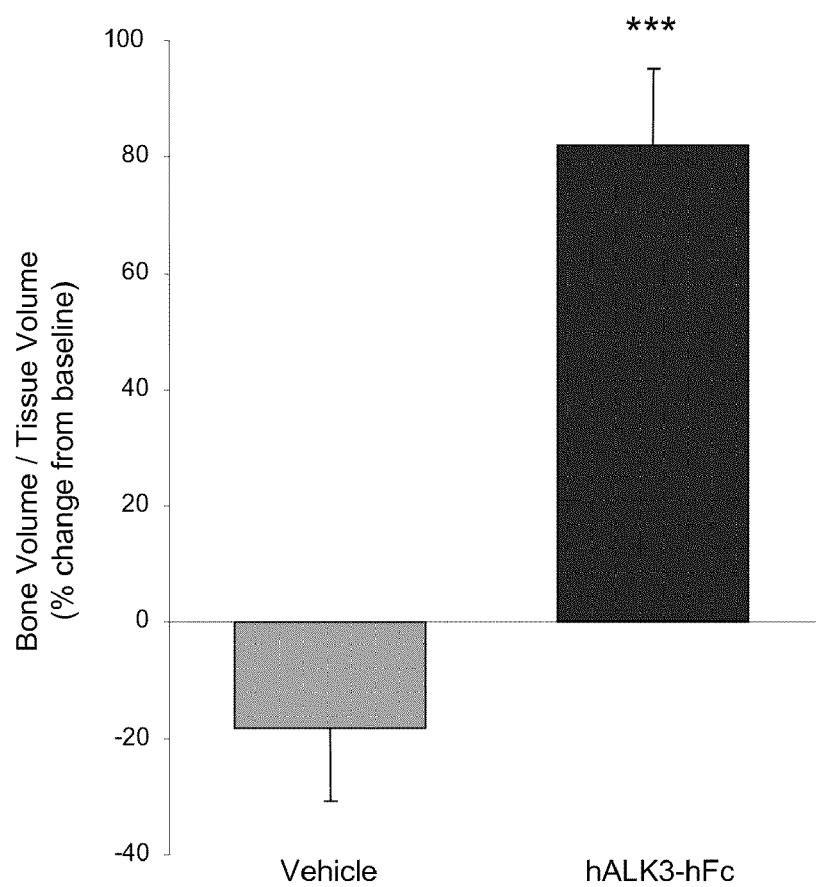

SEQUENCE LISTING

<160> NUMBER OF SEQ ID NOS: 48

<210> SEQ ID NO 1
<211> LENGTH: 532
<212> TYPE: PRT
<213> ORGANISM: Homo sapiens

<400> SEQUENCE: 1

```
Met Pro Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
            20                  25                  30

Thr Gly Met Lys Ser Asp Ser Asp Gln Lys Lys Ser Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Ala Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                165                 170                 175

Lys His Tyr Cys Lys Ser Ile Ser Ser Arg Arg Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285
```

```
Leu Gly Phe Ile Ala Ala Asp Ile Lys Gly Thr Gly Ser Trp Thr Gln
    290                 295                 300
Leu Tyr Leu Ile Thr Asp Tyr His Glu Asn Gly Ser Leu Tyr Asp Phe
305                 310                 315                 320
Leu Lys Cys Ala Thr Leu Asp Thr Arg Ala Leu Leu Lys Leu Ala Tyr
                325                 330                 335
Ser Ala Ala Cys Gly Leu Cys His Leu His Thr Glu Ile Tyr Gly Thr
            340                 345                 350
Gln Gly Lys Pro Ala Ile Ala His Arg Asp Leu Lys Ser Lys Asn Ile
        355                 360                 365
Leu Ile Lys Lys Asn Gly Ser Cys Cys Ile Ala Asp Leu Gly Leu Ala
    370                 375                 380
Val Lys Phe Asn Ser Asp Thr Asn Glu Val Asp Val Pro Leu Asn Thr
385                 390                 395                 400
Arg Val Gly Thr Lys Arg Tyr Met Ala Pro Glu Val Leu Asp Glu Ser
                405                 410                 415
Leu Asn Lys Asn His Phe Gln Pro Tyr Ile Met Ala Asp Ile Tyr Ser
            420                 425                 430
Phe Gly Leu Ile Ile Trp Glu Met Ala Arg Arg Cys Ile Thr Gly Gly
        435                 440                 445
Ile Val Glu Glu Tyr Gln Leu Pro Tyr Tyr Asn Met Val Pro Ser Asp
    450                 455                 460
Pro Ser Tyr Glu Asp Met Arg Glu Val Val Cys Val Lys Arg Leu Arg
465                 470                 475                 480
Pro Ile Val Ser Asn Arg Trp Asn Ser Asp Glu Cys Leu Arg Ala Val
                485                 490                 495
Leu Lys Leu Met Ser Glu Cys Trp Ala His Asn Pro Ala Ser Arg Leu
            500                 505                 510
Thr Ala Leu Arg Ile Lys Lys Thr Leu Ala Lys Met Val Glu Ser Gln
        515                 520                 525
Asp Val Lys Ile
    530

<210> SEQ ID NO 2
<211> LENGTH: 1596
<212> TYPE: DNA
<213> ORGANISM: Homo sapiens

<400> SEQUENCE: 2
atgcctcagc tatacattta catcagatta ttgggagcct atttgttcat catttctcgt      60
gttcaaggac agaatctgga tagtatgctt catggcactg ggatgaaatc agactccgac     120
cagaaaaagt cagaaaatgg agtaacctta gcaccagagg ataccttgcc ttttttaaag     180
tgctattgct cagggcactg tccagatgat gctattaata cacatgcat aactaatgga      240 cattgctttg ccatcataga agaagatgac cagggagaaa ccacattagc ttcagggtgt     300
atgaaatatg aaggatctga ttttcagtgc aaagattctc caaaagccca gctacgccgg     360
acaatagaat gttgtcggac caatttatgt aaccagtatt gcaacccac actgcccct      420 gttgtcatag gtccgttttt tgatggcagc attcgatggc tggttttgct catttctatg     480
gctgtctgca taattgctat gatcatcttc tccagctgct tttgttacaa acattattgc     540
aagagcatct caagcagacg tcgttacaat cgtgatttgg aacaggatga agcatttatt     600
ccagttggag aatcactaaa agaccttatt gaccagtcac aaagttctgg tagtgggtct     660
ggactacctt tattggttca gcgaactatt gccaaacaga ttcagatggt ccggcaagtt     720
```

```
ggtaaaggcc gatatggaga agtatggatg ggcaaatggc gtggcgaaaa agtggcggtg      780
aaagtattct ttaccactga agaagccagc tggtttcgag aacagaaat ctaccaaact       840 gtgctaatgc gccatgaaaa catacttggt ttcatagcgg cagacattaa aggtacaggt      900
tcctggactc agctctattt gattactgat taccatgaaa atggatctct ctatgacttc      960
ctgaaatgtg ctacactgga caccagagcc ctgcttaaat tggcttattc agctgcctgt    1020
ggtctgtgcc acctgcacac agaaatttat ggcacccaag aaagcccgc aattgctcat     1080 cgagacctaa agagcaaaaa catcctcatc aagaaaaatg ggagttgctg cattgctgac    1140
ctgggccttg ctgttaaatt caacagtgac acaaatgaag ttgatgtgcc cttgaatacc    1200
agggtgggca ccaaacgcta catggctccc gaagtgctgg acgaaagcct gaacaaaaac    1260
cacttccagc cctacatcat ggctgacatc tacagcttcg gcctaatcat ttgggagatg    1320
gctcgtcgtt gtatcacagg agggatcgtg gaagaatacc aattgccata ttacaacatg    1380
gtaccgagtg atccgtcata cgaagatatg cgtgaggttg tgtgtgtcaa acgtttgcgg    1440
ccaattgtgt ctaatcggtg aacagtgat gaatgtctac gagcagtttt gaagctaatg     1500
tcagaatgct gggcccacaa tccagcctcc agactcacag cattgagaat taagaagacg    1560
cttgccaaga tggttgaatc ccaagatgta aaaatc                               1596

<210> SEQ ID NO 3
<211> LENGTH: 129
<212> TYPE: PRT
<213> ORGANISM: Homo sapiens

<400> SEQUENCE: 3

Gln Asn Leu Asp Ser Met Leu His Gly Thr Gly Met Lys Ser Asp Ser
1               5                  10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
        35                  40                  45

Ile Asn Asn Thr Cys Ile Thr Asn Gly His Cys Phe Ala Ile Ile Glu
    50                  55                  60

Glu Asp Asp Gln Gly Glu Thr Thr Leu Ala Ser Gly Cys Met Lys Tyr
65                  70                  75                  80

Glu Gly Ser Asp Phe Gln Cys Lys Asp Ser Pro Lys Ala Gln Leu Arg
                85                  90                  95

Arg Thr Ile Glu Cys Cys Arg Thr Asn Leu Cys Asn Gln Tyr Leu Gln
            100                 105                 110

Pro Thr Leu Pro Pro Val Val Ile Gly Pro Phe Phe Asp Gly Ser Ile
        115                 120                 125

Arg

<210> SEQ ID NO 4
<211> LENGTH: 387
<212> TYPE: DNA
<213> ORGANISM: Homo sapiens

<400> SEQUENCE: 4
cagaatctgg atagtatgct tcatggcact gggatgaaat cagactccga ccagaaaaag      60
tcagaaaatg gagtaaccct agcaccagag gataccttgc cttttttaaa gtgctattgc     120
tcagggcact gtccagatga tgctattaat aacacatgca taactaatgg acattgcttt     180
gccatcatag aagaagatga ccagggagaa accacattag cttcagggtg tatgaaatat     240
```

```
gaaggatctg attttcagtg caaagattct ccaaaagccc agctacgccg gacaatagaa    300
tgttgtcgga ccaatttatg taaccagtat ttgcaaccca cactgccccc tgttgtcata    360
ggtccgtttt ttgatggcag cattcga                                        387
```

```
<210> SEQ ID NO 5
<211> LENGTH: 225
<212> TYPE: PRT
<213> ORGANISM: Homo sapiens

<400> SEQUENCE: 5
```

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

```
<210> SEQ ID NO 6
<211> LENGTH: 678
<212> TYPE: DNA
<213> ORGANISM: Homo sapiens

<400> SEQUENCE: 6
```

```
actcacacat gcccaccgtg cccagcacct gaactcctgg ggggaccgtc agtcttcctc    60
ttccccccaa acccaaggac accctcatg atctcccgga cccctgaggt cacatgcgtg     120
gtggtggacg tgagccacga agaccctgag gtcaagttca actggtacgt ggacggcgtg    180
gaggtgcata atgccaagac aaagccgcgg gaggagcagt acaacagcac gtaccgtgtg    240
gtcagcgtcc tcaccgtcct gcaccaggac tggctgaatg gcaaggagta caagtgcaag    300
gtctccaaca aagccctccc agcccccatc gagaaaacca tctccaaagc caagggcag     360
```

```
ccccgagaac cacaggtgta caccctgccc ccatcccggg aggagatgac caagaaccag    420
gtcagcctga cctgcctggt caaaggcttc tatcccagcg acatcgccgt ggagtgggag    480
agcaatgggc agccggagaa caactacaag accacgcctc ccgtgctgga ctccgacggc    540
tccttcttcc tctatagcaa gctcaccgtg gacaagagca ggtggcagca ggggaacgtc    600
ttctcatgct ccgtgatgca tgaggctctg cacaaccact acacgcagaa gagcctctcc    660
ctgtccccgg gtaaatga                                                 678
```

```
<210> SEQ ID NO 7
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

```
Gln Asn Leu Asp Ser Met Leu His Gly Thr Gly Met Lys Ser Asp Ser
  1               5                  10                  15

Asp Gln Lys Lys Ser Glu Asn Gly Val Thr Leu Ala Pro Glu Asp Thr
             20                  25                  30

Leu Pro Phe Leu Lys Cys Tyr Cys Ser Gly His Cys Pro Asp Asp Ala
         35                  40                  45

Ile Asn Asn Thr Cys Ile Thr Asn Gly His Cys Phe Ala Ile Ile Glu
     50                  55                  60

Glu Asp Asp Gln Gly Glu Thr Thr Leu Ala Ser Gly Cys Met Lys Tyr
 65                  70                  75                  80

Glu Gly Ser Asp Phe Gln Cys Lys Asp Ser Pro Lys Ala Gln Leu Arg
                 85                  90                  95

Arg Thr Ile Glu Cys Cys Arg Thr Asn Leu Cys Asn Gln Tyr Leu Gln
            100                 105                 110

Pro Thr Leu Pro Pro Val Val Ile Gly Pro Phe Phe Asp Gly Ser Ile
        115                 120                 125

Arg Thr Gly Gly Gly Thr His Thr Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300
```

```
Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
            325                 330                 335

Ser Val Met His Glu Ala Leu His Asn His Tyr Thr Gln Lys Ser Leu
        340                 345                 350

Ser Leu Ser Pro Gly Lys
        355

<210> SEQ ID NO 8
<211> LENGTH: 23
<212> TYPE: PRT
<213> ORGANISM: Unknown
<220> FEATURE:
<223> OTHER INFORMATION: Description of Unknown: Native leader sequence

<400> SEQUENCE: 8

Met Pro Gln Leu Tyr Ile Tyr Ile Arg Leu Leu Gly Ala Tyr Leu Phe
1               5                   10                  15

Ile Ile Ser Arg Val Gln Gly
            20

<210> SEQ ID NO 9
<211> LENGTH: 22
<212> TYPE: PRT
<213> ORGANISM: Unknown
<220> FEATURE:
<223> OTHER INFORMATION: Description of Unknown: Tissue plasminogen
      activator leader sequence

<400> SEQUENCE: 9

Met Asp Ala Met Lys Arg Gly Leu Cys Cys Val Leu Leu Leu Cys Gly
1               5                   10                  15

Ala Val Phe Val Ser Pro
            20

<210> SEQ ID NO 10
<211> LENGTH: 21
<212> TYPE: PRT
<213> ORGANISM: Apis sp.

<400> SEQUENCE: 10

Met Lys Phe Leu Val Asn Val Ala Leu Val Phe Met Val Val Tyr Ile
1               5                   10                  15

Ser Tyr Ile Tyr Ala
            20

<210> SEQ ID NO 11
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His
            20                  25                  30

Gly Thr Gly Met Lys Ser Asp Ser Asp Gln Lys Lys Ser Glu Asn Gly
        35                  40                  45

Val Thr Leu Ala Pro Glu Asp Thr Leu Pro Phe Leu Lys Cys Tyr Cys
```

```
              50                  55                  60
Ser Gly His Cys Pro Asp Asp Ala Ile Asn Asn Thr Cys Ile Thr Asn
 65                  70                  75                  80

Gly His Cys Phe Ala Ile Ile Glu Glu Asp Asp Gln Gly Glu Thr Thr
                 85                  90                  95

Leu Ala Ser Gly Cys Met Lys Tyr Glu Gly Ser Asp Phe Gln Cys Lys
                100                 105                 110

Asp Ser Pro Lys Ala Gln Leu Arg Arg Thr Ile Glu Cys Cys Arg Thr
            115                 120                 125

Asn Leu Cys Asn Gln Tyr Leu Gln Pro Thr Leu Pro Pro Val Val Ile
130                 135                 140

Gly Pro Phe Phe Asp Gly Ser Ile Arg Thr Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
            195                 200                 205

Lys Phe Asn Trp Tyr Val Asp Gly Val Glu Val His Asn Ala Lys Thr
210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
            275                 280                 285

Ser Arg Glu Glu Met Thr Lys Asn Gln Val Ser Leu Thr Cys Leu Val
            290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
            355                 360                 365

Asn His Tyr Thr Gln Lys Ser Leu Ser Leu Ser Pro Gly Lys
370                 375                 380

<210> SEQ ID NO 12
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggatgcaa tgaagagagg gctctgctgt gtgctgctgc tgtgtggagc agtcttcgtt      60
tcgcccggcg cccagaatct ggatagtatg cttcatggca ctgggatgaa atcagactcc     120
gaccagaaaa agtcagaaaa tggagtaacc ttagcaccag gaataccttg ccttttttta     180
aagtgctatt gctcagggca ctgtccagat gatgctatta taacacatg cataactaat      240
```

| | |
|---|---|
| ggacattgct tgccatcat agaagaagat gaccagggag aaaccacatt agcttcaggg | 300 |
| tgtatgaaat atgaaggatc tgattttcag tgcaaagatt ctccaaaagc ccagctacgc | 360 |
| cggacaatag aatgttgtcg gaccaattta tgtaaccagt atttgcaacc cacactgccc | 420 |
| cctgttgtca taggtccgtt ttttgatggc agcattcgaa ccggtggggg tactcacaca | 480 |
| tgcccaccgt gcccagcacc tgaactcctg gggggaccgt cagtcttcct cttcccccca | 540 |
| aaacccaagg acaccctcat gatctcccgg acccctgagg tcacatgcgt ggtggtggac | 600 |
| gtgagccacg aagaccctga ggtcaagttc aactggtacg tggacggcgt ggaggtgcat | 660 |
| aatgccaaga caaagccgcg ggaggagcag tacaacagca cgtaccgtgt ggtcagcgtc | 720 |
| ctcaccgtcc tgcaccagga ctggctgaat ggcaaggagt acaagtgcaa ggtctccaac | 780 |
| aaagccctcc cagcccccat cgagaaaacc atctccaaag ccaagggca gccccgagaa | 840 |
| ccacaggtgt acaccctgcc cccatcccgg gaggagatga ccaagaacca ggtcagcctg | 900 |
| acctgcctgg tcaaaggctt ctatcccagc gacatcgccg tggagtggga gagcaatggg | 960 |
| cagccggaga caactacaa gaccacgcct cccgtgctgg actccgacgg ctccttcttc | 1020 |
| ctctatagca agctcaccgt ggacaagagc aggtggcagc aggggaacgt cttctcatgc | 1080 |
| tccgtgatgc atgaggctct gcacaaccac tacacgcaga agagcctctc cctgtccccg | 1140 |
| ggtaaa | 1146 |

<210> SEQ ID NO 13
<211> LENGTH: 1146
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

| | |
|---|---|
| tttacccggg gacagggaga ggctcttctg cgtgtagtgg ttgtgcagag cctcatgcat | 60 |
| cacggagcat gagaagacgt tcccctgctg ccacctgctc ttgtccacgg tgagcttgct | 120 |
| atagaggaag aaggagccgt cggagtccag cacgggaggc gtggtcttgt agttgttctc | 180 |
| cggctgccca ttgctctccc actccacggc gatgtcgctg ggatagaagc cttgaccag | 240 |
| gcaggtcagg ctgacctggt tcttggtcat ctcctcccgg gatgggggca gggtgtacac | 300 |
| ctgtggttct cggggctgcc ctttggcttt ggagatggtt ttctcgatgg gggctgggag | 360 |
| ggctttgttg gagaccttgc acttgtactc cttgccattc agccagtcct ggtgcaggac | 420 |
| ggtgaggacg ctgaccacac ggtacgtgct gttgtactgc tcctcccgcg ctttgtctt | 480 |
| ggcattatgc acctccacgc cgtccacgta ccagttgaac ttgacctcag gtcttcgtg | 540 |
| gctcacgtcc accaccacgc atgtgacctc aggggtccgg gagatcatga gggtgtcctt | 600 |
| gggtttggg gggaagagga agactgacgg tcccccagg agttcaggtg ctgggcacgg | 660 |
| tgggcatgtg tgagtacccc caccggttcg aatgctgcca tcaaaaaacg gacctatgac | 720 |
| aacagggggc agtgtgggtt gcaaatactg gttacataaa ttggtccgac aacattctat | 780 |
| tgtccggcgt agctgggctt ttggagaatc tttgcactga aaatcagatc cttcatattt | 840 |
| catacaccct gaagctaatg tggtttctcc ctggtcatct tcttctatga tggcaaagca | 900 |
| atgtccatta gttatgcatg tgttattaat agcatcatct ggacagtgcc ctgagcaata | 960 |
| gcactttaaa aaaggcaagg tatcctctgg tgctaaggtt actccatttt ctgacttttt | 1020 |
| ctggtcggag tctgatttca tcccagtgcc atgaagcata ctatccagat tctgggcgcc | 1080 |

```
gggcgaaacg aagactgctc cacacagcag cagcacacag cagagccctc tcttcattgc   1140
atccat                                                              1146
```

<210> SEQ ID NO 14
<211> LENGTH: 395
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 14

```
Met Asp Ala Met Lys Arg Gly Leu Cys Cys Val Leu Leu Cys Gly
1               5                   10                  15

Ala Val Phe Val Ser Pro Gly Ala Gln Asn Leu Asp Ser Met Leu His
                20                  25                  30

Gly Thr Gly Met Lys Ser Asp Ser Asp Gln Lys Lys Ser Glu Asn Gly
            35                  40                  45

Val Thr Leu Ala Pro Glu Asp Thr Leu Pro Phe Leu Lys Cys Tyr Cys
    50                  55                  60

Ser Gly His Cys Pro Asp Asp Ala Ile Asn Asn Thr Cys Ile Thr Asn
65                  70                  75                  80

Gly His Cys Phe Ala Ile Ile Glu Glu Asp Asp Gln Gly Glu Thr Thr
                85                  90                  95

Leu Ala Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
        115                 120                 125

Asn Leu Cys Asn Gln Tyr Leu Gln Pro Thr Leu Pro Pro Val Val Ile
130                 135                 140

Gly Pro Phe Phe Asp Gly Ser Ile Arg Thr Gly Gly Gly Glu Pro Arg
145                 150                 155                 160

Val Pro Ile Thr Gln Asn Pro Cys Pro Pro Leu Lys Glu Cys Pro Pro
                165                 170                 175

Cys Ala Ala Pro Asp Leu Leu Gly Gly Pro Ser Val Phe Ile Phe Pro
            180                 185                 190

Pro Lys Ile Lys Asp Val Leu Met Ile Ser Leu Ser Pro Met Val Thr
        195                 200                 205

Cys Val Val Val Asp Val Ser Glu Asp Asp Pro Asp Val Gln Ile Ser
    210                 215                 220

Trp Phe Val Asn Asn Val Glu Val His Thr Ala Gln Thr Gln Thr His
225                 230                 235                 240

Arg Glu Asp Tyr Asn Ser Thr Leu Arg Val Val Ser Ala Leu Pro Ile
                245                 250                 255

Gln His Gln Asp Trp Met Ser Gly Lys Glu Phe Lys Cys Lys Val Asn
            260                 265                 270

Asn Arg Ala Leu Pro Ser Pro Ile Glu Lys Thr Ile Ser Lys Pro Arg
        275                 280                 285

Gly Pro Val Arg Ala Pro Gln Val Tyr Val Leu Pro Pro Pro Ala Glu
    290                 295                 300

Glu Met Thr Lys Lys Glu Phe Ser Leu Thr Cys Met Ile Thr Gly Phe
305                 310                 315                 320

Leu Pro Ala Glu Ile Ala Val Asp Trp Thr Ser Asn Gly Arg Thr Glu
                325                 330                 335

Gln Asn Tyr Lys Asn Thr Ala Thr Val Leu Asp Ser Asp Gly Ser Tyr
            340                 345                 350
```

Phe Met Tyr Ser Lys Leu Arg Val Gln Lys Ser Thr Trp Glu Arg Gly
    355                 360                 365

Ser Leu Phe Ala Cys Ser Val Val His Glu Gly Leu His Asn His Leu
370                 375                 380

Thr Thr Lys Thr Ile Ser Arg Ser Leu Gly Lys
385                 390                 395

<210> SEQ ID NO 15
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atggatgcaa tgaagagagg gctctgctgt gtgctgctgc tgtgtggagc agtcttcgtt    60
tcgcccggcg cccagaatct ggatagtatg cttcatggca ctgggatgaa atcagactcc   120
gaccagaaaa agtcagaaaa tggagtaacc ttagcaccag aggataccct gcctttttta   180
aagtgctatt gctcagggca ctgtccagat gatgctatta ataacacatg cataactaat   240
ggacattgct ttgccatcat agaagaagat gaccagggag aaaccacatt agcttcaggg   300
tgtatgaaat atgaaggatc tgatttttcag tgcaaagatt ctccaaaagc ccagctacgc   360
cggacaatag aatgttgtcg gaccaattta tgtaaccagt atttgcaacc cacactgccc   420
cctgttgtca taggtccgtt ttttgatggc agcattcgaa ccggtggggg tgagcccaga   480
gtgcccataa cacagaaccc ctgtcctcca ctcaaagagt gtccccatg cgcagctcca   540 gacctcttgg gtggaccatc cgtcttcatc ttccctccaa agatcaagga tgtactcatg   600
atctccctga gccccatggt cacatgtgtg gtggtggatg tgagcgagga tgacccagac   660
gtccagatca gctggtttgt gaacaacgtg aagtacaca cagctcagac acaaacccat   720
agagaggatt acaacagtac tctccgggtg gtcagtgccc tccccatcca gcaccaggac   780
tggatgagtg gcaaggagtt caaatgcaag gtcaacaaca gagccctccc atccccccatc   840 gagaaaacca tctcaaaacc cagagggcca gtaagagctc acaggtata tgtcttgcct   900 ccaccagcag aagagatgac taagaaagag ttcagtctga cctgcatgat cacaggcttc   960
ttacctgccg aaattgctgt ggactggacc agcaatgggc gtacagagca aaactacaag  1020
aacaccgcaa cagtcctgga ctctgatggt tcttacttca gtacagcaa gctcagagta  1080 caaaagagca cttgggaaag aggaagtctt ttcgcctgct cagtggtcca cgagggtctg  1140
cacaatcacc ttacgactaa gaccatctcc cggtctctgg gtaaa                  1185

<210> SEQ ID NO 16
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
tttacccaga gaccgggaga tggtcttagt cgtaaggtga ttgtgcagac cctcgtggac    60
cactgagcag gcgaaaagac ttcctctttc ccaagtgctc ttttgtactc tgagcttgct   120
gtacatgaag taagaaccat cagagtccag gactgttgcg gtgttcttgt agttttgctc   180
tgtacgccca ttgctggtcc agtccacagc aatttcggca ggtaagaagc ctgtgatcat   240

```
gcaggtcaga ctgaactctt tcttagtcat ctcttctgct ggtggaggca agacatatac    300
ctgtggagct cttactggcc ctctgggttt tgagatggtt ttctcgatgg gggatgggag    360
ggctctgttg ttgaccttgc atttgaactc cttgccactc atccagtcct ggtgctggat    420
ggggagggca ctgaccaccc ggagagtact gttgtaatcc tctctatggg tttgtgtctg    480
agctgtgtgt acttccacgt tgttcacaaa ccagctgatc tggacgtctg ggtcatcctc    540
gctcacatcc accaccacac atgtgaccat ggggctcagg gagatcatga gtacatcctt    600
gatctttgga gggaagatga agacggatgg tccacccaag aggtctggag ctgcgcatgg    660
gggacactct ttgagtggag acaggggtt ctgtgttatg ggcactctgg gctcaccccc    720
accggttcga atgctgccat caaaaaacgg acctatgaca cagggggca gtgtgggttg    780 caaatactgg ttacataaat tggtccgaca acattctatt gtccggcgta gctgggcttt    840
tggagaatct ttgcactgaa atcagatcc ttcatatttc atacaccctg aagctaatgt    900
ggtttctccc tggtcatctt cttctatgat ggcaaagcaa tgtccattag ttatgcatgt    960
gttattaata gcatcatctg gacagtgccc tgagcaatag cactttaaaa aaggcaaggt    1020
atcctctggt gctaaggtta ctccattttc tgacttttc tggtcggagt ctgatttcat    1080
cccagtgcca tgaagcatac tatccagatt ctgggcgccg gcgaaacga agactgctcc    1140 acacagcagc agcacacagc agagccctct cttcattgca tccat                   1185

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ala Gln Asn Leu Asp Ser Met Leu His Gly Thr Gly Met Lys
1               5                   10                  15

<210> SEQ ID NO 18
<211> LENGTH: 395
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His
            20                  25                  30

Gly Thr Gly Met Lys Ser Asp Leu Asp Gln Lys Lys Pro Glu Asn Gly
        35                  40                  45

Val Thr Leu Ala Pro Glu Asp Thr Leu Pro Phe Leu Lys Cys Tyr Cys
    50                  55                  60

Ser Gly His Cys Pro Asp Asp Ala Ile Asn Asn Thr Cys Ile Thr Asn
65                  70                  75                  80

Gly His Cys Phe Ala Ile Ile Glu Glu Asp Asp Gln Gly Glu Thr Thr
                85                  90                  95

Leu Thr Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
        115                 120                 125
```

```
Asn Leu Cys Asn Gln Tyr Leu Gln Pro Thr Leu Pro Pro Val Val Ile
    130                 135                 140

Gly Pro Phe Phe Asp Gly Ser Ile Arg Thr Gly Gly Glu Pro Arg
145                 150                 155                 160

Val Pro Ile Thr Gln Asn Pro Cys Pro Leu Lys Glu Cys Pro Pro
                165                 170                 175

Cys Ala Ala Pro Asp Leu Leu Gly Gly Pro Ser Val Phe Ile Phe Pro
                180                 185                 190

Pro Lys Ile Lys Asp Val Leu Met Ile Ser Leu Ser Pro Met Val Thr
            195                 200                 205

Cys Val Val Val Asp Val Ser Glu Asp Asp Pro Asp Val Gln Ile Ser
210                 215                 220

Trp Phe Val Asn Asn Val Glu Val His Thr Ala Gln Thr Gln Thr His
225                 230                 235                 240

Arg Glu Asp Tyr Asn Ser Thr Leu Arg Val Val Ser Ala Leu Pro Ile
                245                 250                 255

Gln His Gln Asp Trp Met Ser Gly Lys Glu Phe Lys Cys Lys Val Asn
                260                 265                 270

Asn Arg Ala Leu Pro Ser Pro Ile Glu Lys Thr Ile Ser Lys Pro Arg
                275                 280                 285

Gly Pro Val Arg Ala Pro Gln Val Tyr Val Leu Pro Pro Pro Ala Glu
            290                 295                 300

Glu Met Thr Lys Lys Glu Phe Ser Leu Thr Cys Met Ile Thr Gly Phe
305                 310                 315                 320

Leu Pro Ala Glu Ile Ala Val Asp Trp Thr Ser Asn Gly Arg Thr Glu
                325                 330                 335

Gln Asn Tyr Lys Asn Thr Ala Thr Val Leu Asp Ser Asp Gly Ser Tyr
                340                 345                 350

Phe Met Tyr Ser Lys Leu Arg Val Gln Lys Ser Thr Trp Glu Arg Gly
            355                 360                 365

Ser Leu Phe Ala Cys Ser Val Val His Glu Gly Leu His Asn His Leu
370                 375                 380

Thr Thr Lys Thr Ile Ser Arg Ser Leu Gly Lys
385                 390                 395

<210> SEQ ID NO 19
<211> LENGTH: 1149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atggatgcaa tgaagagagg gctctgctgt gtgctgctgc tgtgtggagc agtcttcgtt      60
tcgcccggcg cccagaatct ggatagtatg cttcatggca ctgggatgaa atcagactcc     120
gaccagaaaa agtcagaaaa tggagtaacc ttagcaccag aggatacctt gccttttta     180 aagtgctatt gctcagggca ctgtccagat gatgctatta ataacacatg cataactaat     240
ggacattgct ttgccatcat agaagaagat gaccagggag aaaccacatt agcttcaggg     300
tgtatgaaat atgaaggatc tgattttcag tgcaaagatt ctccaaaagc ccagctacgc     360
cggacaatag aatgttgtcg gaccaattta tgtaaccagt atttgcaacc cacactgccc     420
cctgttgtca taggtccgtt ttttgatggc agcattcgaa ccggtggtgg aactcacaca     480
tgcccaccgt gcccagcacc tgaactcctg ggggaccgt cagtcttcct cttccccca      540
```

```
aaacccaagg acaccctcat gatctcccgg accectgagg tcacatgcgt ggtggtggac    600
gtgagccacg aagaccctga ggtcaagttc aactggtacg tggacggcgt ggaggtgcat    660
aatgccaaga caaagccgcg ggaggagcag tacaacagca cgtaccgtgt ggtcagcgtc    720
ctcaccgtcc tgcaccagga ctggctgaat ggcaaggagt acaagtgcaa ggtctccaac    780
aaagccctcc cagcccccat cgagaaaacc atctccaaag ccaagggca gccccgagaa    840
ccacaggtgt acaccctgcc cccatcccgg gaggagatga ccaagaacca ggtcagcctg    900
acctgcctgg tcaaaggctt ctatcccagc gacatcgccg tggagtggga gagcaatggg    960
cagccggaga acaactacaa gaccacgcct cccgtgctgg actccgacgg ctccttcttc   1020
ctctatagca agctcaccgt ggacaagagc aggtggcagc aggggaacgt cttctcatgc   1080
tccgtgatgc atgaggctct gcacaaccac tacacgcaga agagcctctc cctgtctccg   1140
ggtaaatga                                                          1149
```

<210> SEQ ID NO 20
<211> LENGTH: 360
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
            20                  25                  30

Asp Thr Leu Pro Phe Leu Lys Cys Tyr Cys Ser Gly His Cys Pro Asp
        35                  40                  45

Asp Ala Ile Asn Asn Thr Cys Ile Thr Asn Gly His Cys Phe Ala Ile
    50                  55                  60

Ile Glu Glu Asp Asp Gln Gly Glu Thr Thr Leu Ala Ser Gly Cys Met
65                  70                  75                  80

Lys Tyr Glu Gly Ser Asp Phe Gln Cys Lys Asp Ser Pro Lys Ala Gln
                85                  90                  95

Leu Arg Arg Thr Ile Glu Cys Cys Arg Thr Asn Leu Cys Asn Gln Tyr
            100                 105                 110

Leu Gln Pro Thr Leu Pro Pro Val Val Ile Gly Pro Phe Phe Asp Gly
        115                 120                 125

Ser Ile Arg Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
```

```
                245                 250                 255
Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 21
<211> LENGTH: 1113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atggatgcaa tgaagagagg gctctgctgt gtgctgctgc tgtgtggagc agtcttcgtt      60
tcgcccggcg cccagaatct ggatagtatg cttcatggca ctgggatgaa atcagactcc     120
gaccagaaaa agtcagaaaa tggagtaacc ttagcaccag aggataccct gccttttta     180 aagtgctatt gctcagggca ctgtccagat gatgctatta taacacatg cataactaat     240 ggacattgct ttgccatcat agaagaagat gaccagggag aaaccacatt agcttcaggg     300
tgtatgaaat atgaaggatc tgattttcag tgcaaagatt ctccaaaagc ccagctacgc     360
cggacaatag aatgttgtcg gaccaattta tgtaaccagt atttgcaacc cacactgccc     420
cctaccggtg gtgaactca cacatgccca ccgtgcccag cacctgaact cctgggggga     480
ccgtcagtct tcctcttccc cccaaaaccc aaggacaccc tcatgatctc ccggacccct     540
gaggtcacat gcgtggtggt ggacgtgagc acgaagacc tgaggtcaa gttcaactgg     600 tacgtggacg gcgtggaggt gcataatgcc aagacaaagc cgcgggagga gcagtacaac     660
agcacgtacc gtgtggtcag cgtcctcacc gtcctgcacc aggactggct gaatggcaag     720
gagtacaagt gcaaggtctc caacaaagcc ctcccagccc ccatcgagaa aaccatctcc     780
aaagccaaag gcagccccg agaaccacag gtgtacaccc tgcccccatc ccgggaggag     840
atgaccaaga accaggtcag cctgacctgc ctggtcaaag gcttctatcc cagcgacatc     900
gccgtggagt gggagagcaa tgggcagccg gagaacaact acaagaccac gcctcccgtg     960
ctggactccg acggctcctt cttcctctat agcaagctca ccgtggacaa gagcaggtgg    1020
cagcagggga acgtcttctc atgctccgtg atgcatgagg ctctgcacaa ccactacacg    1080
cagaagagcc tctccctgtc tccgggtaaa tga                                 1113

<210> SEQ ID NO 22
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 22

```
Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
        35                  40                  45

Ile Asn Asn Thr Cys Ile Thr Asn Gly His Cys Phe Ala Ile Ile Glu
    50                  55                  60

Glu Asp Asp Gln Gly Glu Thr Thr Leu Ala Ser Gly Cys Met Lys Tyr
65                  70                  75                  80

Glu Gly Ser Asp Phe Gln Cys Lys Asp Ser Pro Lys Ala Gln Leu Arg
                85                  90                  95

Arg Thr Ile Glu Cys Cys Arg Thr Asn Leu Cys Asn Gln Tyr Leu Gln
            100                 105                 110

Pro Thr Leu Pro Pro Thr Gly Gly Thr His Thr Cys Pro Pro Cys
        115                 120                 125

Pro Ala Pro Glu Leu Leu Gly Gly Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

<210> SEQ ID NO 23
<211> LENGTH: 348
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

| Gly | Ala | Gln | Asn | Leu | Asp | Ser | Met | Leu | His | Gly | Thr | Gly | Met | Lys | Ser |
|---|---|---|---|---|---|---|---|---|---|---|---|---|---|---|---|
| 1 | | | | 5 | | | | | 10 | | | | | 15 | |

Asp Ser Asp Gln Lys Lys Ser Glu Asn Gly Val Thr Leu Ala Pro Glu
             20               25               30

Asp Thr Leu Pro Phe Leu Lys Cys Tyr Cys Ser Gly His Cys Pro Asp
           35              40              45

Asp Ala Ile Asn Asn Thr Cys Ile Thr Asn Gly His Cys Phe Ala Ile
 50                  55              60

Ile Glu Glu Asp Asp Gln Gly Glu Thr Thr Leu Ala Ser Gly Cys Met
65                 70               75              80

Lys Tyr Glu Gly Ser Asp Phe Gln Cys Lys Asp Ser Pro Lys Ala Gln
           85              90              95

Leu Arg Arg Thr Ile Glu Cys Cys Arg Thr Asn Leu Cys Asn Gln Tyr
         100              105            110

Leu Gln Pro Thr Leu Pro Pro Thr Gly Gly Thr His Thr Cys Pro
         115              120            125

Pro Cys Pro Ala Pro Glu Leu Leu Gly Gly Pro Ser Val Phe Leu Phe
    130              135             140

Pro Pro Lys Pro Lys Asp Thr Leu Met Ile Ser Arg Thr Pro Glu Val
145                 150              155              160

Thr Cys Val Val Val Asp Val Ser His Glu Asp Pro Glu Val Lys Phe
            165             170            175

Asn Trp Tyr Val Asp Gly Val Glu Val His Asn Ala Lys Thr Lys Pro
         180              185            190

Arg Glu Glu Gln Tyr Asn Ser Thr Tyr Arg Val Val Ser Val Leu Thr
         195              200            205

Val Leu His Gln Asp Trp Leu Asn Gly Lys Glu Tyr Lys Cys Lys Val
    210              215             220

Ser Asn Lys Ala Leu Pro Ala Pro Ile Glu Lys Thr Ile Ser Lys Ala
225                 230              235              240

Lys Gly Gln Pro Arg Glu Pro Gln Val Tyr Thr Leu Pro Pro Ser Arg
         245              250            255

Glu Glu Met Thr Lys Asn Gln Val Ser Leu Thr Cys Leu Val Lys Gly
         260              265            270

Phe Tyr Pro Ser Asp Ile Ala Val Glu Trp Glu Ser Asn Gly Gln Pro
    275              280             285

Glu Asn Asn Tyr Lys Thr Thr Pro Pro Val Leu Asp Ser Asp Gly Ser
    290              295             300

Phe Phe Leu Tyr Ser Lys Leu Thr Val Asp Lys Ser Arg Trp Gln Gln
305                 310              315              320

Gly Asn Val Phe Ser Cys Ser Val Met His Glu Ala Leu His Asn His
            325             330            335

Tyr Thr Gln Lys Ser Leu Ser Leu Ser Pro Gly Lys
         340              345

<210> SEQ ID NO 24
<211> LENGTH: 1131
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 24
atggatgcaa tgaagagagg gctctgctgt gtgctgctgc tgtgtggagc agtcttcgtt    60
tcgcccggcg cccttcatgg cactgggatg aaatcagact ccgaccagaa aaagtcagaa   120

```
aatggagtaa ccttagcacc agaggatacc ttgcctttt  taaagtgcta ttgctcaggg    180
cactgtccag atgatgctat taataacaca tgcataacta atggacattg ctttgccatc    240
atagaagaag atgaccaggg agaaaccaca ttagcttcag ggtgtatgaa atatgaagga    300
tctgattttc agtgcaaaga ttctccaaaa gcccagctac gccggacaat agaatgttgt    360
cggaccaatt tatgtaacca gtatttgcaa cccacactgc ccctgttgt  cataggtccg    420 ttttttgatg gcagcattcg aaccggtggt ggaactcaca catgcccacc gtgcccagca    480
cctgaactcc tggggggacc gtcagtcttc ctcttccccc caaaacccaa ggacaccctc    540
atgatctccc ggacccctga ggtcacatgc gtggtggtgg acgtgagcca cgaagaccct    600
gaggtcaagt tcaactggta cgtggacggc gtggaggtgc ataatgccaa gacaaagccg    660
cgggaggagc agtacaacag cacgtaccgt gtggtcagcg tcctcaccgt cctgcaccag    720
gactggctga atggcaagga gtacaagtgc aaggtctcca acaaagccct cccagccccc    780
atcgagaaaa ccatctccaa agccaaaggg cagccccgag aaccacaggt gtacaccctg    840
cccccatccc gggaggagat gaccaagaac caggtcagcc tgacctgcct ggtcaaaggc    900
ttctatccca gcgacatcgc cgtggagtgg gagagcaatg ggcagccgga gaacaactac    960
aagaccacgc ctcccgtgct ggactccgac ggctccttct tcctctatag caagctcacc   1020
gtggacaaga gcaggtggca gcaggggaac gtcttctcat gctccgtgat gcatgaggct   1080
ctgcacaacc actacacgca gaagagcctc tccctgtctc cgggtaaatg a            1131
```

<210> SEQ ID NO 25
<211> LENGTH: 346
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 25

```
Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
        35                  40                  45

Ile Asn Asn Thr Cys Ile Thr Asn Gly His Cys Phe Ala Ile Ile Glu
    50                  55                  60

Glu Asp Asp Gln Gly Glu Thr Thr Leu Ala Ser Gly Cys Met Lys Tyr
65                  70                  75                  80

Glu Gly Ser Asp Phe Gln Cys Lys Asp Ser Pro Lys Ala Gln Leu Arg
                85                  90                  95

Arg Thr Ile Glu Cys Cys Arg Thr Asn Leu Cys Asn Gln Tyr Leu Gln
            100                 105                 110

Pro Thr Leu Pro Pro Thr Gly Gly Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
```

```
                180                 185                 190
Glu Gln Tyr Asn Ser Thr Tyr Arg Val Val Ser Val Leu Thr Val Leu
            195                 200                 205
His Gln Asp Trp Leu Asn Gly Lys Glu Tyr Lys Cys Lys Val Ser Asn
        210                 215                 220
Lys Ala Leu Pro Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
    290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly Lys
            340                 345

<210> SEQ ID NO 26
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Ala Gln Asn Leu Asp Ser Met Leu His Gly Thr Gly Met Lys Ser
1               5                   10                  15
Asp Ser Asp Gln Lys Lys Ser Glu Asn Gly Val Thr Leu Ala Pro Glu
            20                  25                  30
Asp Thr Leu Pro Phe Leu Lys Cys Tyr Cys Ser Gly His Cys Pro Asp
        35                  40                  45
Asp Ala Ile Asn Asn Thr Cys Ile Thr Asn Gly His Cys Phe Ala Ile
    50                  55                  60
Ile Glu Glu Asp Asp Gln Gly Glu Thr Thr Leu Ala Ser Gly Cys Met
65                  70                  75                  80
Lys Tyr Glu Gly Ser Asp Phe Gln Cys Lys Asp Ser Pro Lys Ala Gln
                85                  90                  95
Leu Arg Arg Thr Ile Glu Cys Cys Arg Thr Asn Leu Cys Asn Gln Tyr
            100                 105                 110
Leu Gln Pro Thr Leu Pro Pro Thr Gly Gly Thr His Thr Cys Pro
        115                 120                 125
Pro Cys Pro Ala Pro Glu Leu Leu Gly Gly Pro Ser Val Phe Leu Phe
    130                 135                 140
Pro Pro Lys Pro Lys Asp Thr Leu Met Ile Ser Arg Thr Pro Glu Val
145                 150                 155                 160
Thr Cys Val Val Val Asp Val Ser His Glu Asp Pro Glu Val Lys Phe
                165                 170                 175
Asn Trp Tyr Val Asp Gly Val Glu Val His Asn Ala Lys Thr Lys Pro
            180                 185                 190
Arg Glu Glu Gln Tyr Asn Ser Thr Tyr Arg Val Val Ser Val Leu Thr
```

```
                195                 200                 205
Val Leu His Gln Asp Trp Leu Asn Gly Lys Glu Tyr Lys Cys Lys Val
210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 27
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atggatgcaa tgaagagagg gctctgctgt gtgctgctgc tgtgtggagc agtcttcgtt        60
tcgcccggcg cccttcatgg cactgggatg aaatcagact ccgaccagaa aaagtcagaa       120
aatggagtaa ccttagcacc agaggatacc ttgccttttt taaagtgcta ttgctcaggg       180
cactgtccag atgatgctat taataacaca tgcataacta atggacattg ctttgccatc       240
atagaagaag atgaccaggg agaaaccaca ttagcttcag ggtgtatgaa atatgaagga       300
tctgattttc agtgcaaaga ttctccaaaa gcccagctac gccggacaat agaatgttgt       360
cggaccaatt tatgtaacca gtatttgcaa cccacactgc cccctgttgt cataggtccg       420
ttttttgatg cagcattccg aaccggtggt ggaactcaca catgcccacc gtgcccagca       480
cctgaactcc tggggggacc gtcagtcttc ctcttccccc caaaacccaa ggacaccctc       540
atgatctccc ggacccctga ggtcacatgc gtggtggtgg acgtgagcca cgaagaccct       600
gaggtcaagt tcaactggta cgtggacggc gtggaggtgc ataatgccaa gacaaagccg       660
cgggaggagc agtacaacag cacgtaccgt gtggtcagcg tcctcaccgt cctgcaccag       720
gactggctga atggcaagga gtacaagtgc aaggtctcca acaaagccct cccagccccc       780
atcgagaaaa ccatctccaa agccaaaggg cagccccgag aaccacaggt gtacaccctg       840
cccccatccc gggaggagat gaccaagaac caggtcagcc tgacctgcct ggtcaaaggc       900
ttctatccca gcgacatcgc cgtggagtgg gagagcaatg ggcagccgga gaacaactac       960
aagaccacgc ctcccgtgct ggactccgac ggctccttct tcctctatag caagctcacc      1020
gtggacaaga gcaggtggca gcaggggaac gtcttctcat gctccgtgat gcatgaggct      1080
ctgcacaacc actacacgca gaagagcctc tccctgtctc cgggtaaatg a              1131

<210> SEQ ID NO 28
```

<211> LENGTH: 354
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Gly Ala Leu His Gly Thr Gly Met Lys Ser Asp Ser Asp Gln Lys Lys
1               5                   10                  15

Ser Glu Asn Gly Val Thr Leu Ala Pro Glu Asp Thr Leu Pro Phe Leu
            20                  25                  30

Lys Cys Tyr Cys Ser Gly His Cys Pro Asp Asp Ala Ile Asn Asn Thr
        35                  40                  45

Cys Ile Thr Asn Gly His Cys Phe Ala Ile Ile Glu Glu Asp Asp Gln
    50                  55                  60

Gly Glu Thr Thr Leu Ala Ser Gly Cys Met Lys Tyr Glu Gly Ser Asp
65                  70                  75                  80

Phe Gln Cys Lys Asp Ser Pro Lys Ala Gln Leu Arg Arg Thr Ile Glu
                85                  90                  95

Cys Cys Arg Thr Asn Leu Cys Asn Gln Tyr Leu Gln Pro Thr Leu Pro
            100                 105                 110

Pro Val Val Ile Gly Pro Phe Phe Asp Gly Ser Ile Arg Thr Gly Gly
        115                 120                 125

Gly Thr His Thr Cys Pro Pro Cys Pro Ala Pro Glu Leu Leu Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys

<210> SEQ ID NO 29
<211> LENGTH: 353

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Leu His Gly Thr Gly Met Lys Ser Asp Ser Asp Gln Lys Lys Ser
1               5                   10                  15

Glu Asn Gly Val Thr Leu Ala Pro Glu Asp Thr Leu Pro Phe Leu Lys
            20                  25                  30

Cys Tyr Cys Ser Gly His Cys Pro Asp Asp Ala Ile Asn Asn Thr Cys
        35                  40                  45

Ile Thr Asn Gly His Cys Phe Ala Ile Ile Glu Glu Asp Asp Gln Gly
    50                  55                  60

Glu Thr Thr Leu Ala Ser Gly Cys Met Lys Tyr Glu Gly Ser Asp Phe
65                  70                  75                  80

Gln Cys Lys Asp Ser Pro Lys Ala Gln Leu Arg Arg Thr Ile Glu Cys
                85                  90                  95

Cys Arg Thr Asn Leu Cys Asn Gln Tyr Leu Gln Pro Thr Leu Pro Pro
            100                 105                 110

Val Val Ile Gly Pro Phe Phe Asp Gly Ser Ile Arg Thr Gly Gly Gly
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 30
<211> LENGTH: 351
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 30

His Gly Thr Gly Met Lys Ser Asp Ser Asp Gln Lys Lys Ser Glu Asn
1               5                   10                  15

Gly Val Thr Leu Ala Pro Glu Asp Thr Leu Pro Phe Leu Lys Cys Tyr
            20                  25                  30

Cys Ser Gly His Cys Pro Asp Asp Ala Ile Asn Asn Thr Cys Ile Thr
        35                  40                  45

Asn Gly His Cys Phe Ala Ile Ile Glu Glu Asp Asp Gln Gly Glu Thr
    50                  55                  60

Thr Leu Ala Ser Gly Cys Met Lys Tyr Glu Gly Ser Asp Phe Gln Cys
65                  70                  75                  80

Lys Asp Ser Pro Lys Ala Gln Leu Arg Arg Thr Ile Glu Cys Cys Arg
                85                  90                  95

Thr Asn Leu Cys Asn Gln Tyr Leu Gln Pro Thr Leu Pro Pro Val Val
            100                 105                 110

Ile Gly Pro Phe Phe Asp Gly Ser Ile Arg Thr Gly Gly Thr His
            115                 120                 125

Thr Cys Pro Pro Cys Pro Ala Pro Glu Leu Leu Gly Gly Pro Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
            165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
            195                 200                 205

Val Leu Thr Val Leu His Gln Asp Trp Leu Asn Gly Lys Glu Tyr Lys
210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
            245                 250                 255

Pro Ser Arg Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
            275                 280                 285

Gly Gln Pro Glu Asn Asn Tyr Lys Thr Thr Pro Pro Val Leu Asp Ser
290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys
            340                 345                 350

<210> SEQ ID NO 31
<211> LENGTH: 352
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Leu His Gly Thr Gly Met Lys Ser Asp Ser Asp Gln Lys Lys Ser Glu
1               5                   10                  15

Asn Gly Val Thr Leu Ala Pro Glu Asp Thr Leu Pro Phe Leu Lys Cys
            20                  25                  30

Tyr Cys Ser Gly His Cys Pro Asp Asp Ala Ile Asn Asn Thr Cys Ile
        35                  40                  45

Thr Asn Gly His Cys Phe Ala Ile Ile Glu Glu Asp Asp Gln Gly Glu
    50                  55                  60

Thr Thr Leu Ala Ser Gly Cys Met Lys Tyr Glu Gly Ser Asp Phe Gln
65                  70                  75                  80

Cys Lys Asp Ser Pro Lys Ala Gln Leu Arg Arg Thr Ile Glu Cys Cys
                85                  90                  95

Arg Thr Asn Leu Cys Asn Gln Tyr Leu Gln Pro Thr Leu Pro Pro Val
            100                 105                 110

Val Ile Gly Pro Phe Phe Asp Gly Ser Ile Arg Thr Gly Gly Gly Thr
            115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350
```

<210> SEQ ID NO 32
<211> LENGTH: 1113
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
atggatgcaa tgaagagagg gctctgctgt gtgctgctgc tgtgtggagc agtcttcgtt    60
tcgcccggcg cccttcatgg cactgggatg aaatcagact ccgaccagaa aaagtcagaa   120
aatggagtaa ccttagcacc agaggatacc ttgccttttt taaagtgcta ttgctcaggg   180
cactgtccag atgatgctat taataacaca tgcataacta atggacattg ctttgccatc   240
atagaagaag atgaccaggg agaaaccaca ttagcttcag ggtgtatgaa atatgaagga   300
tctgattttc agtgcaaaga ttctccaaaa gcccagctac gccggacaat agaatgttgt   360
cggaccaatt tatgtaacca gtatttgcaa cccacactgc ccctgttgt cataggtccg    420
tttaccggtg gtggaactca cacatgccca ccgtgcccag cacctgaact cctgggggga   480
ccgtcagtct tcctcttccc cccaaaaccc aaggacaccc tcatgatctc ccggacccct   540
gaggtcacat gcgtggtggt ggacgtgagc cacgaagacc ctgaggtcaa gttcaactgg   600
tacgtggacg gcgtggaggt gcataatgcc aagacaaagc cgcgggagga gcagtacaac   660
agcacgtacc gtgtggtcag cgtcctcacc gtcctgcacc aggactggct gaatggcaag   720
gagtacaagt gcaaggtctc caacaaagcc ctcccagccc ccatcgagaa aaccatctcc   780
aaagccaaag gcagccccg agaaccacag gtgtacaccc tgcccccatc ccgggaggag   840
atgaccaaga accaggtcag cctgacctgc ctggtcaaag gcttctatcc cagcgacatc   900
gccgtggagt gggagagcaa tgggcagccg gagaacaact acaagaccac gcctcccgtg   960
ctggactccg acggctcctt cttcctctat agcaagctca ccgtggacaa gagcaggtgg  1020
cagcagggga acgtcttctc atgctccgtg atgcatgagg ctctgcacaa ccactacacg  1080
cagaagagcc tctccctgtc tccgggtaaa tga                               1113
```

<210> SEQ ID NO 33
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gly Ala Leu His Gly Thr Gly Met Lys Ser Asp Ser Asp Gln Lys Lys
1               5                   10                  15

Ser Glu Asn Gly Val Thr Leu Ala Pro Glu Asp Thr Leu Pro Phe Leu
            20                  25                  30

Lys Cys Tyr Cys Ser Gly His Cys Pro Asp Asp Ala Ile Asn Asn Thr
        35                  40                  45

Cys Ile Thr Asn Gly His Cys Phe Ala Ile Glu Glu Asp Asp Gln
    50                  55                  60

Gly Glu Thr Thr Leu Ala Ser Gly Cys Met Lys Tyr Glu Gly Ser Asp
65                  70                  75                  80

Phe Gln Cys Lys Asp Ser Pro Lys Ala Gln Leu Arg Arg Thr Ile Glu
                85                  90                  95

Cys Cys Arg Thr Asn Leu Cys Asn Gln Tyr Leu Gln Pro Thr Leu Pro
            100                 105                 110

Pro Val Val Ile Gly Pro Phe Thr Gly Gly Gly Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160
```

```
Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
                340                 345

<210> SEQ ID NO 34
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Leu His Gly Thr Gly Met Lys Ser Asp Ser Asp Gln Lys Lys Ser
1               5                   10                  15

Glu Asn Gly Val Thr Leu Ala Pro Glu Asp Thr Leu Pro Phe Leu Lys
            20                  25                  30

Cys Tyr Cys Ser Gly His Cys Pro Asp Asp Ala Ile Asn Asn Thr Cys
        35                  40                  45

Ile Thr Asn Gly His Cys Phe Ala Ile Ile Glu Glu Asp Asp Gln Gly
    50                  55                  60

Glu Thr Thr Leu Ala Ser Gly Cys Met Lys Tyr Glu Gly Ser Asp Phe
65                  70                  75                  80

Gln Cys Lys Asp Ser Pro Lys Ala Gln Leu Arg Arg Thr Ile Glu Cys
                85                  90                  95

Cys Arg Thr Asn Leu Cys Asn Gln Tyr Leu Gln Pro Thr Leu Pro Pro
            100                 105                 110

Val Val Ile Gly Pro Phe Thr Gly Gly Thr His Thr Cys Pro Pro
        115                 120                 125

Cys Pro Ala Pro Glu Leu Leu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Lys Phe Asn
                165                 170                 175
```

```
Trp Tyr Val Asp Gly Val Glu Val His Asn Ala Lys Thr Lys Pro Arg
            180                 185                 190

Glu Glu Gln Tyr Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Ala Leu Pro Ala Pro Ile Glu Lys Thr Ile Ser Lys Ala Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 35
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

His Gly Thr Gly Met Lys Ser Asp Ser Asp Gln Lys Ser Glu Asn
1               5                   10                  15

Gly Val Thr Leu Ala Pro Glu Asp Thr Leu Pro Phe Leu Lys Cys Tyr
            20                  25                  30

Cys Ser Gly His Cys Pro Asp Asp Ala Ile Asn Asn Thr Cys Ile Thr
        35                  40                  45

Asn Gly His Cys Phe Ala Ile Ile Glu Glu Asp Asp Gln Gly Glu Thr
    50                  55                  60

Thr Leu Ala Ser Gly Cys Met Lys Tyr Glu Gly Ser Asp Phe Gln Cys
65                  70                  75                  80

Lys Asp Ser Pro Lys Ala Gln Leu Arg Arg Thr Ile Glu Cys Cys Arg
                85                  90                  95

Thr Asn Leu Cys Asn Gln Tyr Leu Gln Pro Thr Leu Pro Pro Val Val
            100                 105                 110

Ile Gly Pro Phe Thr Gly Gly Thr His Thr Cys Pro Pro Cys Pro
        115                 120                 125

Ala Pro Glu Leu Leu Gly Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190
```

```
Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 36
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Leu His Gly Thr Gly Met Lys Ser Asp Ser Asp Gln Lys Lys Ser Glu
1               5                   10                  15

Asn Gly Val Thr Leu Ala Pro Glu Asp Thr Leu Pro Phe Leu Lys Cys
            20                  25                  30

Tyr Cys Ser Gly His Cys Pro Asp Asp Ala Ile Asn Asn Thr Cys Ile
        35                  40                  45

Thr Asn Gly His Cys Phe Ala Ile Ile Glu Glu Asp Asp Gln Gly Glu
    50                  55                  60

Thr Thr Leu Ala Ser Gly Cys Met Lys Tyr Glu Gly Ser Asp Phe Gln
65                  70                  75                  80

Cys Lys Asp Ser Pro Lys Ala Gln Leu Arg Arg Thr Ile Glu Cys Cys
                85                  90                  95

Arg Thr Asn Leu Cys Asn Gln Tyr Leu Gln Pro Thr Leu Pro Pro Val
            100                 105                 110

Val Ile Gly Pro Phe Thr Gly Gly Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205
```

```
His Gln Asp Trp Leu Asn Gly Lys Glu Tyr Lys Cys Lys Val Ser Asn
            210                 215                 220
Lys Ala Leu Pro Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
                275                 280                 285
Asn Tyr Lys Thr Thr Pro Pro Val Leu Asp Ser Asp Gly Ser Phe Phe
        290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly Lys
            340                 345

<210> SEQ ID NO 37
<211> LENGTH: 1095
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atggatgcaa tgaagagagg gctctgctgt gtgctgctgc tgtgtggagc agtcttcgtt      60
tcgcccggcg cccttcatgg cactgggatg aaatcagact ccgaccagaa aaagtcagaa     120
aatggagtaa ccttagcacc agaggatacc ttgccttttt taaagtgcta ttgctcaggg     180
cactgtccag atgatgctat taataacaca tgcataacta atggacattg ctttgccatc     240
atagaagaag atgaccaggg agaaaccaca ttagcttcag ggtgtatgaa atatgaagga     300
tctgattttc agtgcaaaga ttctccaaaa gcccagctac gccggacaat gaatgttgt      360 cggaccaatt tatgtaacca gtatttgcaa cccacactgc ccctaccggt ggtggaact      420 cacacatgcc caccgtgccc agcacctgaa ctcctggggg gaccgtcagt cttcctcttc     480
cccccaaaac ccaaggacac cctcatgatc tcccggaccc ctgaggtcac atgcgtggtg     540
gtggacgtga gccacgaaga ccctgaggtc aagttcaact ggtacgtgga cggcgtggag     600
gtgcataatg ccaagacaaa gccgcgggag gagcagtaca acagcacgta ccgtgtggtc     660
agcgtcctca ccgtcctgca ccaggactgg ctgaatggca aggagtacaa gtgcaaggtc     720
tccaacaaag ccctcccagc ccccatcgag aaaaccatct ccaaagccaa agggcagccc     780
cgagaaccac aggtgtacac cctgccccca tcccgggagg agatgaccaa gaaccaggtc     840
agcctgacct gcctggtcaa aggcttctat cccagcgaca tcgccgtgga gtgggagagc     900
aatgggcagc cggagaacaa ctacaagacc acgcctcccg tgctggactc cgacggctcc     960
ttcttcctct atagcaagct caccgtggac aagagcaggt ggcagcaggg gaacgtcttc    1020
tcatgctccg tgatgcatga ggctctgcac aaccactaca cgcagaagag cctctccctg    1080
tctccgggta aatga                                                    1095

<210> SEQ ID NO 38
<211> LENGTH: 342
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 38

Gly Ala Leu His Gly Thr Gly Met Lys Ser Asp Ser Asp Gln Lys Lys
1               5                   10                  15

Ser Glu Asn Gly Val Thr Leu Ala Pro Glu Asp Thr Leu Pro Phe Leu
            20                  25                  30

Lys Cys Tyr Cys Ser Gly His Cys Pro Asp Asp Ala Ile Asn Asn Thr
        35                  40                  45

Cys Ile Thr Asn Gly His Cys Phe Ala Ile Ile Glu Glu Asp Asp Gln
    50                  55                  60

Gly Glu Thr Thr Leu Ala Ser Gly Cys Met Lys Tyr Glu Gly Ser Asp
65                  70                  75                  80

Phe Gln Cys Lys Asp Ser Pro Lys Ala Gln Leu Arg Arg Thr Ile Glu
                85                  90                  95

Cys Cys Arg Thr Asn Leu Cys Asn Gln Tyr Leu Gln Pro Thr Leu Pro
            100                 105                 110

Pro Thr Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 39
<211> LENGTH: 341
<212> TYPE: PRT
<213> ORGANISM: Artificial Sequence
<220> FEATURE:
<223> OTHER INFORMATION: Description of Artificial Sequence: Synthetic

```
polypeptide

<400> SEQUENCE: 39

Ala Leu His Gly Thr Gly Met Lys Ser Asp Ser Asp Gln Lys Lys Ser
1               5                   10                  15

Glu Asn Gly Val Thr Leu Ala Pro Glu Asp Thr Leu Pro Phe Leu Lys
            20                  25                  30

Cys Tyr Cys Ser Gly His Cys Pro Asp Asp Ala Ile Asn Asn Thr Cys
        35                  40                  45

Ile Thr Asn Gly His Cys Phe Ala Ile Ile Glu Glu Asp Asp Gln Gly
    50                  55                  60

Glu Thr Thr Leu Ala Ser Gly Cys Met Lys Tyr Glu Gly Ser Asp Phe
65                  70                  75                  80

Gln Cys Lys Asp Ser Pro Lys Ala Gln Leu Arg Arg Thr Ile Glu Cys
                85                  90                  95

Cys Arg Thr Asn Leu Cys Asn Gln Tyr Leu Gln Pro Thr Leu Pro Pro
            100                 105                 110

Thr Gly Gly Gly Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 40
<211> LENGTH: 339
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40
```

His Gly Thr Gly Met Lys Ser Asp Ser Asp Gln Lys Lys Ser Glu Asn
1               5                   10                  15

Gly Val Thr Leu Ala Pro Glu Asp Thr Leu Pro Phe Leu Lys Cys Tyr
            20                  25                  30

Cys Ser Gly His Cys Pro Asp Asp Ala Ile Asn Asn Thr Cys Ile Thr
            35                  40                  45

Asn Gly His Cys Phe Ala Ile Ile Glu Glu Asp Asp Gln Gly Glu Thr
        50                  55                  60

Thr Leu Ala Ser Gly Cys Met Lys Tyr Glu Gly Ser Asp Phe Gln Cys
65                  70                  75                  80

Lys Asp Ser Pro Lys Ala Gln Leu Arg Arg Thr Ile Glu Cys Cys Arg
                85                  90                  95

Thr Asn Leu Cys Asn Gln Tyr Leu Gln Pro Thr Leu Pro Pro Thr Gly
            100                 105                 110

Gly Gly Thr His Thr Cys Pro Pro Cys Pro Ala Pro Glu Leu Leu Gly
            115                 120                 125

Gly Pro Ser Val Phe Leu Phe Pro Pro Lys Pro Lys Asp Thr Leu Met
        130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Glu Glu Met Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys

<210> SEQ ID NO 41
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Leu His Gly Thr Gly Met Lys Ser Asp Ser Asp Gln Lys Lys Ser Glu
1               5                   10                  15

Asn Gly Val Thr Leu Ala Pro Glu Asp Thr Leu Pro Phe Leu Lys Cys
            20                  25                  30

Tyr Cys Ser Gly His Cys Pro Asp Asp Ala Ile Asn Asn Thr Cys Ile
        35                  40                  45

Thr Asn Gly His Cys Phe Ala Ile Ile Glu Gly Asp Asp Gln Gly Glu
 50                  55                  60

Thr Thr Leu Ala Ser Gly Cys Met Lys Tyr Glu Gly Ser Asp Phe Gln
 65                  70                  75                  80

Cys Lys Asp Ser Pro Lys Ala Gln Leu Arg Arg Thr Ile Glu Cys Cys
                85                  90                  95

Arg Thr Asn Leu Cys Asn Gln Tyr Leu Gln Pro Thr Leu Pro Pro Thr
            100                 105                 110

Gly Gly Gly Thr His Thr Cys Pro Pro Cys Pro Ala Pro Glu Leu Leu
            115                 120                 125

Gly Gly Pro Ser Val Phe Leu Phe Pro Pro Lys Pro Lys Asp Thr Leu
        130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Ala Leu Pro Ala Pro
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Glu Glu Met Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
        275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Gly Gly Gly
1

<210> SEQ ID NO 43
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Gly Gly Gly
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly Gly
1

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Gly Gly Gly Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Gly Gly Gly Gly
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 47

His His His His His His
1               5

<210> SEQ ID NO 48
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
```

-continued

```
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 48

Thr His Thr Cys Pro Pro Cys Pro Ala Pro Glu Leu Leu Gly Gly Pro
1               5                  10                  15

Ser Val Phe Leu Phe Pro Pro Lys Pro Lys Asp Thr Leu Met Ile Ser
            20                  25                  30

Arg Thr Pro Glu Val Thr Cys Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225
```

BMP-ALK3 ANTAGONISTS AND USES FOR PROMOTING BONE GROWTH

RELATED APPLICATIONS

This application claims the benefit of U.S. Provisional Application Nos. 61/211,557, filed on Mar. 30, 2009, 61/306,331, filed on Feb. 19, 2010, and 61/314,556, filed on Mar. 16, 2010. All the teachings of the above-referenced applications are incorporated herein by reference.

SEQUENCE LISTING

The instant application contains a Sequence Listing which has been submitted via EFS-Web and is hereby incorporated by reference in its entirety. Said ASCII copy, created on May 20, 2010, is named PHPH471 txt and is 99,730 bytes in size.

BACKGROUND OF THE INVENTION

Disorders of the bone, ranging from osteoporosis to fractures, represent a set of pathological states for which there are few effective pharmaceutical agents. Treatment instead focuses on physical and behavioral interventions, including immobilization, exercise and changes in diet. It would be beneficial to have therapeutic agents that promote bone growth and increase bone density for the purpose of treating a variety of bone disorders.

Bone growth and mineralization are dependent on the activities of two cell types, osteoclasts and osteoblasts, although chondrocytes and cells of the vasculature also participate in critical aspects of these processes. Developmentally, bone formation occurs through two mechanisms, endochondral ossification and intramembranous ossification, with the former responsible for longitudinal bone formation and the later responsible for the formation of topologically flat bones, such as the bones of the skull. Endochondral ossification requires the sequential formation and degradation of cartilaginous structures in the growth plates that serve as templates for the formation of osteoblasts, osteoclasts, the vasculature and subsequent mineralization. During intramembranous ossification, bone is formed directly in the connective tissues. Both processes require the infiltration of osteoblasts and subsequent matrix deposition.

Fractures and other structural disruptions of bone are healed through a process that, at least superficially, resembles the sequence of developmental events of osteogenesis, including the formation of cartilaginous tissue and subsequent mineralization. The process of fracture healing can occur in two ways. Direct or primary bone healing occurs without callus formation. Indirect or secondary bone healing occurs with a callus precursor stage. Primary healing of fractures involves the reformation of mechanical continuity across a closely-set disruption. Under suitable conditions, bone-resorbing cells surrounding the disruption show a tunnelling resorptive response and establish pathways for the penetration of blood vessels and subsequent healing. Secondary healing of bones follows a process of inflammation, soft callus formation, callus mineralisation and callus remodelling. In the inflammation stage, haematoma and haemorrhage formation results from the disruption of periosteal and endosteal blood vessels at the site of injury. Inflammatory cells invade the area. In soft callus formation stage, the cells produce new vessels, fibroblasts, intracellular material and supporting cells, forming granulation tissue in the space between the fracture fragments. Clinical union across the disruption is established by fibrous or cartilaginous tissue (soft callus). Osteoblasts are formed and mediate the mineralization of soft callus, which is then replaced by lamellar bone and subjected to the normal remodeling processes.

In addition to fractures and other physical disruptions of bone structure, loss of bone mineral content and bone mass can be caused by a wide variety of conditions and may result in significant medical problems. Changes to bone mass occur in a relatively predictable way over the life of an individual. Up to about age 30, bones of both men and women grow to maximal mass through linear growth of the endochondral growth plates and radial growth. After about age 30 (for trabecular bone, e.g., flat bones such as the vertebrae and pelvis) and age 40 (for cortical bone, e.g., long bones found in the limbs), slow bone loss occurs in both men and women. In women, a final phase of substantial bone loss also occurs, probably due to postmenopausal estrogen deficiencies. During this phase, women may lose an additional 10% of bone mass from the cortical bone and 25% from the trabecular compartment. Whether progressive bone loss results in a pathological condition such as osteoporosis depends largely on the initial bone mass of the individual and whether there are exacerbating conditions.

Bone loss is sometimes characterized as an imbalance in the normal bone remodeling process. Healthy bone is constantly subject to remodeling. Remodeling begins with resorption of bone by osteoclasts. The resorbed bone is then replaced by new bone tissue, which is characterized by collagen formation by osteoblasts, and subsequent calcification. In healthy individuals the rates of resorption and formation are balanced. Osteoporosis is a chronic, progressive condition, marked by a shift towards resorption, resulting in an overall decrease in bone mass and bone mineralization. Osteoporosis in humans is preceded by clinical osteopenia (bone mineral density that is greater than one standard deviation but less than 2.5 standard deviations below the mean value for young adult bone). Worldwide, approximately 75 million people are at risk for osteoporosis.

Thus, methods for controlling the balance between osteoclast and osteoblast activity can be useful for promoting the healing of fractures and other damage to bone as well as the treatment of disorders, such as osteoporosis, associated with loss of bone mass and bone mineralization.

With respect to osteoporosis, estrogen, calcitonin, osteocalcin with vitamin K, or high doses of dietary calcium are all used as therapeutic interventions. Other therapeutic approaches to osteoporosis include bisphosphonates, parathyroid hormone, calcimimetics, statins, anabolic steroids, lanthanum and strontium salts, and sodium fluoride. Such therapeutics, however, are often associated with undesirable side effects.

Bone loss is also a significant complication of many cancers, and may be caused by tumor metastases to bone, the activation of osteoclasts or the effects of chemotherapeutic treatment. In particular, anti-estrogen therapies that are used widely in the treatment of breast cancer can cause significant bone loss.

Other bone disorders, such as osteogenesis imperfecta, may result from genetic, developmental, nutritional of other pathologies and deficiencies.

Thus, it is an object of the present disclosure to provide compositions and methods for promoting bone growth and mineralization.

SUMMARY OF THE INVENTION

In part, the disclosure demonstrates that molecules having ALK3 or BMP antagonist activity ("ALK3 antagonists" and "BMP antagonists") can be used to increase bone density, promote bone growth, and/or increase bone strength. This observation is particularly surprising, given the large body of literature and clinical experience indicating that many BMPs, and particularly BMP2, BMP4 and BMP7, are potent stimulators of bone formation. The disclosure demonstrates that a soluble form of ALK3 acts as an inhibitor of BMP-ALK3 signaling and promotes increased bone density, bone growth, and bone strength in vivo. While not wishing to be bound to any particular mechanism, it appears that the soluble form of ALK3 achieves this effect by inhibiting BMP2 and/or BMP4, and perhaps other ligands which signal through ALK3. Thus, the disclosure establishes that antagonists of the BMP-ALK3 signaling pathway may be used to increase bone density and promote bone growth. While soluble ALK3 may affect bone through a mechanism other than, or in addition to, BMP antagonism, the disclosure nonetheless demonstrates that desirable therapeutic agents may be selected on the basis of BMP-ALK3 antagonist activity. Therefore, in certain embodiments, the disclosure provides methods for using BMP-ALK3 antagonists, including, for example, BMP-binding ALK3 polypeptides, anti-BMP antibodies, anti-ALK3 antibodies, BMP- or ALK3-targeted small molecules and aptamers, and nucleic acids that decrease expression of BMP and ALK3, to treat disorders associated with low bone density or low bone strength, such as osteoporosis, or to promote bone growth in patients in need thereof, such as in patients having a bone fracture. In additional embodiments, the disclosure identifies truncated forms of ALK3 polypeptides (e.g., ALK3-Fc polypeptides) that have advantageous properties and retain appropriate BMP2 or BMP4 binding.

In certain aspects, the disclosure provides polypeptides comprising a soluble ALK3 polypeptide that binds to BMP2 and/or BMP4. The soluble ALK3 polypeptide may bind to additional ligands also. ALK3 polypeptides may be formulated as a pharmaceutical preparation comprising the BMP-binding ALK3 polypeptide and a pharmaceutically acceptable carrier. Preferably, the BMP-binding ALK3 polypeptide binds to BMP2 and/or BMP4 with a $K_D$ less than 1 micromolar or less than 100, 10 or 1 nanomolar. Preferably the composition is at least 95% pure, with respect to other polypeptide components, as assessed by size exclusion chromatography, and more preferably, the composition is at least 98% pure. A BMP-binding ALK3 polypeptide for use in such a preparation may be any of those disclosed herein, such as a polypeptide having an amino acid sequence selected from SEQ ID NOs: 3, 7, 11, 14, 20, 22, 23, 25, 26, 28, 29, 30, 31, 33, 34, 35, 36, 38, 39, 40, or 41, or having an amino acid sequence that is at least 80%, 85%, 90%, 95%, 97%, 98% or 99% identical to an amino acid sequence selected from SEQ ID NOs: 3, 7, 11, 14, 20, 22, 23, 25, 26, 28, 29, 30, 31, 33, 34, 35, 36, 38, 39, 40, or 41, including N- and/or C-terminal truncations of no more than 1, 2, 3, 4, 5, 6, 7, 8, 9, 10, 11, 12, 13, 14, 15, 16, 17, 18, 19, 20, 21, 22, 23, 24 or 25 amino acids of SEQ ID NO:3, and optionally fused to an Fc fusion protein, with or without a linker. In particular, the disclosure provides ALK3 polypeptides with a truncation of 0 to 7 amino acids at the N-terminus of the ALK3 ECD portion and 0 to 12 amino acids at the C-terminus of the ALK3 ECD portion, thus describing a function portion corresponding to amino acids 8 to 117 of SEQ ID NO:3 and polypeptides comprising a protein that is at least 80%, 85%, 90%, 95%, 97%, 98% or 99% identical to the amino acid sequence of 8 to 117 of SEQ ID NO:3. Notably, human ALK3 and murine ALK3 have 97 to 98% identity at the amino acid sequence level in the extracellular domain, and proteins comprising such domains from the human or mouse protein are shown herein to exhibit similar activity in vitro and in vivo. A BMP-binding ALK3 polypeptide may include a functional fragment of a natural ALK3 polypeptide, such as one comprising at least 10, 20 or 30 amino acids of a sequence selected from SEQ ID NOs: 1 or 3. Surprisingly, as demonstrated herein, ALK3 proteins that include a deletion of amino acids at the C-terminal region of the ALK3 extracellular domain retain activity against BMP2 and BMP4 while diminishing activity against other ligands (e.g., BMP6 and BMP7) thus providing an improvement in ligand selectivity, which is generally desirable to diminish unanticipated off-target effects in clinical development or commercialization. Such variations may include a deletion of no more than 6 or 7, no more than 12 or no more than 24 amino acids from the C-terminus of SEQ ID NO:3. Optionally, a form truncated at the C-terminus may also be truncated by no more than 1, 2, 3, 4, 5, 6 or 7 amino acids at the N-terminus. The aforementioned variations of ALK3 proteins may be included in an ALK3-Fc fusion protein, which may comprise any linker disclosed herein (or no linker at all), including a linker having the sequence GGG or TGGG (SEQ ID NO: 42) or SGGG (SEQ ID NO: 43), and an Fc portion derived from a human IgG1, IgG2, IgG3 or IgG4 or other mammamlian immunoglobulin.

A soluble, BMP-binding ALK3 polypeptide may include one, two, five or more alterations in the amino acid sequence (e.g., in the ligand-binding domain) relative to a naturally occurring ALK3 polypeptide. The alteration in the amino acid sequence may, for example, alter glycosylation of the polypeptide when produced in a mammalian, insect or other eukaryotic cell or alter proteolytic cleavage of the polypeptide relative to the naturally occurring ALK3 polypeptide.

A BMP-binding ALK3 polypeptide may be a fusion protein that has, as one domain, an ALK3 polypeptide (e.g., a ligand-binding portion of ALK3) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. An BMP-binding ALK3 fusion protein may include an immunoglobulin Fc domain (wild-type or mutant) or a serum albumin or other polypeptide portion that provides desirable properties such as improved pharmacokinetics, improved solubility or improved stability. In a preferred embodiment, an ALK3-Fc fusion comprises a relatively unstructured linker positioned between the Fc domain and the extracellular ALK3 domain. This unstructured linker may correspond to the C-terminal end of the extracellular domain of ALK3, or it may be an artificial sequence of 1, 2, 3, 4 or 5 amino acids or a length of between 5 and 15, 20, 30, 50 or more amino acids that are relatively free of secondary structure, or a mixture of both. A linker may be rich in glycine and proline residues and may, for example, contain a single sequence of threonine/serine and glycines or repeating sequences of threonine/serine and/or glycines (e.g., GGG, GGGG (SEQ ID NO: 44), TG$_4$ (SEQ ID NO: 45), SG$_4$ (SEQ ID NO: 46), TG$_3$ (SEQ ID NO: 42), or SG$_3$ (SEQ ID NO: 43) singlets or repeats). A fusion protein may include a purification subsequence, such as an epitope tag, a FLAG tag, a polyhistidine sequence, and a GST fusion. Optionally, a soluble ALK3 polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as a compound that is used to treat a bone disorder. Preferably, a pharmaceutical preparation is substantially pyrogen free. In general, it is preferable that an ALK3 protein be expressed in a mammalian cell line that mediates suitably natural glycosylation of the ALK3 protein so as to diminish the likelihood of an unfavorable immune response in a patient. Human and CHO cell lines have been used successfully, and it is expected that other common mammalian expression systems will be useful.

In certain aspects, the disclosure provides nucleic acids encoding a soluble BMP-binding ALK3 polypeptide. An isolated polynucleotide may comprise a coding sequence for a soluble, BMP-binding ALK3 polypeptide, such as described above. For example, an isolated nucleic acid may include a sequence coding for an extracellular domain (e.g., ligand-binding domain) of ALK3 and a sequence that would code for part or all of the transmembrane domain and/or the cytoplasmic domain of ALK3, but for a stop codon positioned within the transmembrane domain or the cytoplasmic domain, or positioned between the extracellular domain and the transmembrane domain or cytoplasmic domain. For example, an isolated polynucleotide may comprise a full-length ALK3 polynucleotide sequence such as SEQ ID NO: 2 or 4, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ALK3. Preferred nucleic acid sequences are SEQ ID NO: 12, 13, 15, 16, 19, 21, 24, 27, 32 or 37 and nucleic acids that hybridize to such nucleic acids or the complements thereof under stringent hybridization conditions. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a soluble, BMP-binding ALK3 polypeptide. Such a method may include expressing any of the nucleic acids (e.g., SEQ ID NO: 2, 4, 12, 13, 15, 16, 19, 21, 24, 27, 32 or 37) disclosed herein in a suitable cell, such as a Chinese hamster ovary (CHO) cell. Such a method may comprise: a) culturing a cell under conditions suitable for expression of the soluble ALK3 polypeptide, wherein said cell is transformed with a soluble ALK3 expression construct; and b) recovering the soluble ALK3 polypeptide so expressed. Soluble ALK3 polypeptides may be recovered as crude, partially purified or highly purified fractions. Purification may be achieved by a series of purification steps, including, for example, one, two or three or more of the following, in any order: protein A chromatography, anion exchange chromatography (e.g., Q sepharose), hydrophobic interaction chromatography (e.g., phenylsepharose), size exclusion chromatography, and cation exchange chromatography.

In certain aspects, a BMP-ALK3 antagonist disclosed herein, such as a soluble, BMP-binding ALK3 polypeptide, may be used in a method for promoting bone growth or increasing bone density in a subject. In certain embodiments, the disclosure provides methods for treating a disorder associated with low bone density, or to promote bone growth, in patients in need thereof. A method may comprise administering to a subject in need thereof an effective amount of BMP-ALK3 antagonist. In certain aspects, the disclosure provides uses of BMP-ALK3 antagonist for making a medicament for the treatment of a disorder or condition as described herein.

In certain aspects, the disclosure provides a method for identifying an agent that stimulates growth of, or increased mineralization of, bone. The method comprises: a) identifying a test agent that binds to BMPs or a ligand-binding domain of an ALK3 polypeptide; and b) evaluating the effect of the agent on growth of, or mineralization of, bone.

BRIEF DESCRIPTION OF THE DRAWINGS

FIG. 1 shows the native amino acid sequence of human ALK3 precursor (SEQ ID NO: 1). The ALK3 extracellular domain (residues 24-152) is underlined.

FIG. 2 shows the native nucleotide sequence encoding human ALK3 precursor (SEQ ID NO: 2). The sequence encoding the ALK3 extracellular domain (nucleotides 70-456) is underlined.

FIG. 3 shows the native amino acid sequence of the extracellular domain of human ALK3 (SEQ ID NO: 3).

FIG. 4 shows the native nucleotide sequence encoding the extracellular domain of human ALK3 (SEQ ID NO: 4).

FIG. 5 shows the native amino acid sequence of human IgG1 Fc domain (SEQ ID NO: 5).

FIG. 6 shows the native nucleotide sequence encoding human IgG1 Fc domain (SEQ ID NO: 6).

FIG. 7 shows the amino acid sequence of leaderless hALK3(24-152)-hFc (SEQ ID NO: 7). The human ALK3 extracellular domain (SEQ ID NO: 3) is underlined, and the TGGG linker sequence (SEQ ID NO: 42) is in bold.

FIG. 8 shows the full amino acid sequence of hALK3(24-152)-hFc with TPA leader (SEQ ID NO: 11). The human ALK3 extracellular domain (SEQ ID NO: 3) is underlined, and the TGGG linker sequence (SEQ ID NO: 42) is in bold.

FIG. 9 shows a nucleotide sequence encoding hALK3(24-152)-hFc with TPA leader. SEQ ID NO: 12 corresponds to the coding strand, and SEQ ID NO: 13 corresponds to the anti-coding strand. The sequence encoding the human ALK3 extracellular domain (SEQ ID NO: 4) is underlined.

FIG. 10 shows the full amino acid sequence of hALK3(24-152)-mFc with TPA leader (SEQ ID NO: 14). The human ALK3 extracellular domain (SEQ ID NO: 3) is underlined, and the TGGG linker sequence (SEQ ID NO: 42) is in bold.

FIG. 11 shows a nucleotide sequence encoding hALK3 (24-152)-mFc with TPA leader. SEQ ID NO: 15 corresponds to the coding strand, and SEQ ID NO: 16 corresponds to the anti-coding strand. The sequence encoding the human ALK3 extracellular domain (SEQ ID NO: 4) is underlined.

FIG. 17 shows the effect of hALK3(24-152)-mFc treatment for 4 weeks on trabecular bone microarchitecture in female mice. Representative three-dimensional images of trabecular bone in the proximal tibia were generated by micro-CT. Scale bars=300 μm.

FIG. 18 shows examples of three approaches disclosed herein to interfere with signaling by the BMP-ALK3 signaling axis for the purpose of stimulating bone formation. A: ALK3-Fc. B: Antibody against selected BMP ligand(s). C. Antibody against the ligand binding region of ALK3 extracellular domain. "BMP2" is used to illustrate that the BMP may be BMP2, BMP4 or another high affinity ligand of ALK3.

FIG. 19 shows the effect of hALK3(24-152)-mFc treatment for 6 weeks on maximum bone load in female mice. Unilateral analysis of the femur was conducted ex vivo with an Instron mechanical testing device. Data in newtons (N) are means (n=8 per group)±SEM. **, P<0.01 vs. vehicle. hALK3 (24-152)-mFc increased maximum bone load by 30%.

FIG. 20 shows the effect of hALK3(24-152)-mFc treatment for 6 weeks on bone stiffness in female mice. Unilateral analysis of the femur was conducted ex vivo with an Instron mechanical testing device. Data in newtons (N) per mm are means (n=8 per group)±SEM. *, P<0.05 vs. vehicle. hALK3 (24-152)-mFc increased bone stiffness by 14%.

FIG. 21 shows the effect of hALK3(24-152)-mFc treatment for 6 weeks on energy to bone failure in female mice. Unilateral analysis of the femur was conducted ex vivo with an Instron mechanical testing device. Data in millijoules (mJ) are means (n=8 per group)±SEM. *, P<0.05 vs. vehicle. hALK3(24-152)-mFc increased energy to failure by 32%.

FIG. 22 shows the effect of mALK3(24-152)-mFc treatment on trabecular bone volume in an OVX mouse model of established osteopenia. Measurements of the proximal tibia were made by micro-CT. Data are means (n=7-8 per group), and error bars represent±2 SEM. *, P<0.05 vs. OVX+vehicle. Prior to dosing, OVX mice had reduced trabecular bone volume compared to sham-operated mice. Compared to OVX controls, mALK3(24-152)-mFc increased bone volume significantly at 28 and 56 days of treatment.

FIG. 23 shows the effect of mALK3(24-152)-mFc treatment on cortical bone thickness in an OVX mouse model of osteopenia. Measurements of cortical bone were made by micro-CT. Data are means (n=7-8 per group), and error bars represent±2 SEM. *, P<0.05 vs. OVX+vehicle. Compared to OVX controls, mALK3(24-152)-mFc increased cortical thickness significantly at 56 days of treatment.

FIG. 24 shows the effect of mALK3(24-152)-mFc treatment on endosteal circumference in an OVX mouse model of osteopenia. Measurements of the tibial shaft were made by micro-CT. Data are means (n=7-8 per group), and error bars represent±2 SEM. *, P<0.05 vs. OVX+vehicle. Compared to OVX controls, mALK3(24-152)-mFc reduced endosteal circumference significantly at 56 days of treatment, thus providing additional evidence of cortical bone growth.

FIG. 25 shows the effect of mALK3(24-152)-mFc treatment on whole-body bone mineral density in an OVX mouse model of osteopenia as determined by DEXA. Data are means (n=7-8 per group)±SEM. *, P<0.05 vs. OVX+vehicle. Compared to OVX controls, mALK3(24-152)-mFc increased whole-body bone density significantly at 14, 28, 42, and 56 days of treatment.

FIG. 26 shows the effect of mALK3(24-152)-mFc treatment on vertebral bone mineral density in an OVX mouse model of osteopenia. Analysis of the lumbar spine (vertebrae L1-L6) was conducted by DEXA. Data are means (n=7-8 per group)±SEM. *, P<0.05 vs. OVX+vehicle. Compared to OVX controls, mALK3(24-152)-mFc increased vertebral bone density significantly at 14, 28, 42, and 56 days of treatment.

FIG. 27 shows the effect of mALK3-mFc treatment on bone mineral density of the femur-tibia in an OVX mouse model of osteopenia as determined by DEXA. Analysis of the entire femur and proximal tibia was conducted by DEXA. Data are means (n=7-8 per group)±SEM. *, P<0.05 vs. OVX+ vehicle. Compared to OVX controls, mALK3(24-152)-mFc increased femoral-tibial bone density significantly at 28, 42, and 56 days of treatment.

FIG. 28 shows the effect of mALK3(24-152)-mFc for 56 days on vertebral bone microarchitecture in an OVX mouse model of osteopenia. Representative three-dimensional images of trabecular bone in lumbar vertebrae (L5) were generated ex vivo by micro-CT. Scale bar=300 μm.

FIG. 29 shows the effect of mALK3(24-152)-mFc on bone volume in female mice as assessed in the distal femur by histomophometry. Data are means±SEM; n=6 per group per time point. **, P<0.01 vs. vehicle at corresponding time points. Compared to vehicle, mALK3(24-152)-mFc increased bone volume significantly at all time points.

FIG. 30 shows the effect of mALK3(24-152)-mFc on bone formation rate in female mice as assessed in the distal femur by histomophometry. Data are means±SEM; n=6 per group per time point. ***, P<0.001 vs. vehicle at corresponding time point. Compared to vehicle, mALK3(24-152)-mFc increased bone formation rate significantly at 28 days of treatment, thus providing evidence of anabolic bone formation.

FIG. 31 shows the effect of mALK3(24-152)-mFc on bone mineralizing surface in female mice as assessed in the distal femur by histomophometry. Data are means±SEM; n=6 per group per time point. **, P<0.01; *, P<0.05 vs. vehicle at corresponding time points. Compared to vehicle, mALK3 (24-152)-mFc increased mineralizing surface significantly at 14 and 28 days of treatment, thus providing additional evidence of anabolic bone formation.

FIG. 32 shows the effect of mALK3(24-152)-mFc on osteoclast surface in female mice as assessed in the distal femur by histomophometry. Data are means±SEM; n=6 per group per time point. **, P<0.01 vs. vehicle at corresponding time point. Compared to vehicle, mALK3(24-152)-mFc reduced osteoclast surface significantly at 28 days of treatment, thus providing evidence of antiresorptive bone formation.

FIG. 33 shows the effect of mALK3(24-152)-mFc on serum levels of RANKL (receptor activator for nuclear factor κB ligand) in female mice as determined by Luminex xMAP® assay. Data are means±SEM; n=6 per group per time point. **, P<0.01; *, P<0.05 vs. vehicle at corresponding time points. Compared to vehicle, mALK3(24-152)-mFc reduced circulating RANKL levels significantly at all time points.

FIG. 34 shows the effect of mALK3(24-152)-mFc on serum osteoprotegerin (OPG) levels in female mice as determined by Luminex xMAP® assay. Data are means±SEM; n=6 per group per time point. **, P<0.01; *, P<0.05 vs. vehicle at corresponding time points. Compared to vehicle, mALK3(24-152)-mFc increased circulating OPG levels significantly at 28 and 42 days of treatment.

FIG. 35 shows the effect of mALK3(24-152)-mFc on sclerostin mRNA levels in the femur and tibia of female mice as assessed by real-time polymerase chain reaction (RT-PCR). Data are means±SEM. ***, P<0.001; *, P<0.05 vs. vehicle at corresponding time points. Compared to vehicle, mALK3 (24-152)-mFc reduced sclerostin mRNA levels significantly at 2, 7, and 28 days of treatment.

FIG. 36 shows the effect of hALK3(24-152)-hFc on bone volume in female mice. Bone volume was assessed in the proximal tibia by micro-CT at Day 0 (baseline) and again at Day 42 (ex vivo). Data are means±SEM; n=6 per group. ***, P<0.001 vs. vehicle. Over the course of the experiment, bone volume decreased by nearly 20% in vehicle-treated controls but increased by more than 80% with hALK3(24-152)-hFc treatment.

DETAILED DESCRIPTION OF THE INVENTION

1. Overview

Figure 12:
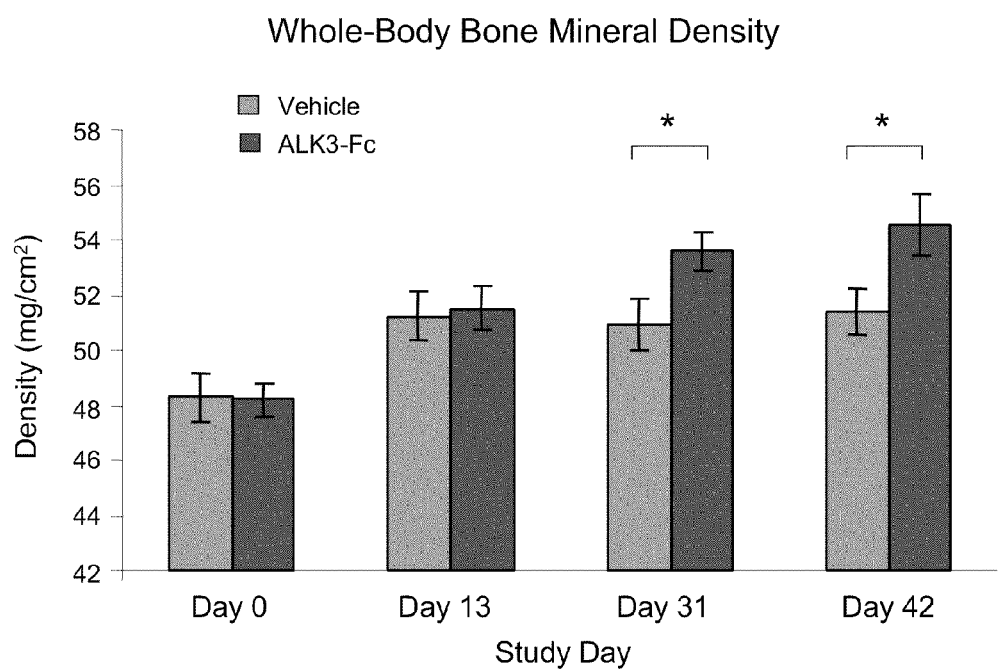
FIG. 12 shows the effect of hALK3(24-152)-mFc treatment on whole-body bone mineral density in female mice. Measurements were made by dual energy x-ray absorptiometry (DEXA). Data are means (n=8 per group)±SEM. *, $P<0.05$ vs. vehicle by unpaired t-test. hALK3(24-152)-mFc increased whole-body bone density significantly after 31 and 42 days of treatment.

In part, the present disclosure demonstrates the surprising result that inhibitors of the BMP-ALK3 signaling pathway, such as an ALK3-Fc protein, promote bone formation in animals. ALK3 is a receptor for members of the transforming growth factor-beta (TGF-beta)/bone morphogenetic protein (BMP) superfamily. The TGF-beta/BMP superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350: 2682-8.

TGF-$\beta$ signals are mediated by heteromeric complexes of type I and type II serine/threonine kinase receptors, which phosphorylate and activate downstream Smad proteins upon ligand stimulation (Massague, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Activin receptor-like kinase-3 (ALK3) is a type I receptor mediating effects of multiple ligands in the BMP family and is also known as bone morphogenetic protein receptor, type IA (BMPR1A), or activin A receptor, type II-like kinase (ACVRLK). Unlike several type I receptors with ubiquitous tissue expression, ALK3 displays a restricted pattern of expression consistent with more specialized functionality (ten Dijke, 1993, Oncogene 8:2879-2887). ALK3 is generally recognized as a high affinity receptor for BMP2, BMP4, BMP7 and other members of the BMP family. BMP2 and BMP7 are potent stimulators of osteoblastic differentiation, and are now used clinically to induce bone formation in spine fusions and certain non-union fractures. ALK3 is regarded as a key receptor in mediating BMP2 and BMP4 signaling in osteoblasts (Lavery et al., 2008, J. Biol. Chem. 283:20948-20958). A homozygous ALK3 knockout mouse dies early in embryogenesis (day 9.5), however, adult mice carrying a conditional disruption of ALK3 in osteoblasts have been recently reported to exhibit increased bone mass, although the newly formed bone showed evidence of disorganization (Kamiya, 2008, J. Bone Miner. Res. 23:2007-2017; Kamiya, 2008, Development 135:3801-3811). This finding is in startling contrast to the effectiveness of BMP2 and BMP7 (ligands for ALK3) as bone building agents in clinical use.

As demonstrated herein, a soluble ALK3 polypeptide (ALK3-Fc), which shows substantial preference in binding to BMP2 and BMP4 is effective to promote bone growth and increase bone density in vivo. While not wishing to be bound to any particular mechanism, it is expected that the effect of ALK3 is caused primarily by a BMP antagonist effect, given the very strong BMP2 and BMP4 binding (picomolar dissociation constant) exhibited by the particular soluble ALK3 construct used in these studies. Regardless of mechanism, it is apparent from the data presented herein that BMP-ALK3 antagonists do increase bone density in normal mice. Surprisingly, the bone generated by treatment with ALK3-Fc shows no evidence of the type of disorganization observed in the ALK3 conditional knockout mice. It should be noted that bone is a dynamic tissue, with growth or shrinkage and increased or decreased density depending on a balance of factors that produce bone and stimulate mineralization (primarily osteoblasts) and factors that destroy and demineralize bone (primarily osteoclasts). Bone growth and mineralization may be increased by increasing the productive factors, by decreasing the destructive factors, or both. The terms "promote bone growth" and "increase bone mineralization" refer to the observable physical changes in bone and are intended to be neutral as to the mechanism by which changes in bone occur.

The mouse model for bone growth/density that was used in the studies described herein is considered to be highly predictive of efficacy in humans, and therefore, this disclosure provides methods for using ALK3 polypeptides and other BMP-ALK3 antagonists to promote bone growth and increase bone density in humans. BMP-ALK3 antagonists include, for example, BMP-binding soluble ALK3 polypeptides, antibodies that bind to BMP and disrupt ALK3 binding, antibodies that bind to ALK3 and disrupt BMP binding, non-antibody proteins selected for BMP or ALK3 binding (see e.g., WO/2002/088171, WO/2006/055689, WO/2002/032925, WO/2005/037989, US 2003/0133939, and US 2005/0238646 for examples of such proteins and methods for design and selection of same), randomized peptides selected for BMP or ALK3 binding, often affixed to an Fc domain. Two different proteins (or other moieties) with BMP or ALK3 binding activity, especially BMP binders that block the type I (e.g., a soluble type I activin receptor) and type II (e.g., a soluble type II activin receptor) binding sites, respectively, may be linked together to create a bifunctional binding molecule. Nucleic acid aptamers, small molecules and other agents that inhibit the BMP-ALK3 signaling axis are also contemplated. Additionally, nucleic acids, such as antisense molecules, siRNAs or ribozymes that inhibit BMPs, or, particularly, ALK3 expression, can be used as BMP-ALK3 antagonists.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. ALK3 Polypeptides

In certain aspects, the present invention relates to ALK3 polypeptides. As used herein, the term "ALK3" refers to a family of activin receptor-like kinase-3 (ALK3) [also referred to as bone morphogenetic protein receptor, type IA (BMPR1A), or activin A receptor, type II-like kinase (ACVRLK)] proteins from any species and variants derived from such ALK3 proteins by mutagenesis or other modification. Reference to ALK3 herein is understood to be a reference to any one of the currently identified forms. Members of the ALK3 family are generally transmembrane proteins, composed of a ligand-binding extracellular domain with a cysteine-rich region, a transmembrane domain, and a cytoplasmic domain with predicted serine/threonine kinase activity.

The term "ALK3 polypeptide" includes polypeptides comprising any naturally occurring polypeptide of an ALK3 family member as well as any variants thereof (including mutants, fragments, fusions, and peptidomimetic forms) that retain a useful activity. For example, ALK3 polypeptides include polypeptides derived from the sequence of any known ALK3 having a sequence at least about 80% identical to the sequence of an ALK3 polypeptide, and preferably at least 85%, 90%, 95%, 97%, 99% or greater identity. For example, an ALK3 polypeptide of the invention may bind to and inhibit the function of an ALK3 protein and/or BMPs. Preferably, an ALK3 polypeptide promotes bone growth and bone mineralization. Examples of ALK3 polypeptides include human ALK3 precursor polypeptide (SEQ ID NO: 1) and soluble human ALK3 polypeptides (e.g., SEQ ID NOs: 3, 7, 11, 14, 20, 22, 23, 25, 26, 28, 29, 30, 31, 33, 34, 35, 36, 38, 39, 40, or 41).

The human ALK3 precursor protein sequence (SEQ ID NO: 1) is shown in FIG. 1, and the nucleic acid sequence encoding human ALK3 precursor protein (SEQ ID NO: 2; nucleotides 549-2144 of Genbank entry NM_004329) is shown in FIG. 2. The human ALK3 soluble (extracellular), processed polypeptide sequence (SEQ ID NO: 3) is shown in FIG. 3, and the nucleic acid sequence encoding the human ALK3 extracellular domain (SEQ ID NO: 4; nucleotides 618-1004 of Genbank entry NM_004329) is shown in FIG. 4.

In a specific embodiment, the invention relates to soluble ALK3 polypeptides. As described herein, the term "soluble ALK3 polypeptide" generally refers to polypeptides comprising an extracellular domain of an ALK3 protein. The term "soluble ALK3 polypeptide," as used herein, includes any naturally occurring extracellular domain of an ALK3 protein as well as any variants thereof (including mutants, fragments and peptidomimetic forms). A BMP-binding ALK3 polypeptide is one that retains the ability to bind to BMPs, particularly BMP2 and BMP4. Preferably, a BMP-binding ALK3 polypeptide will bind to BMP with a dissociation constant of 1 nM or less. The amino acid sequence of human ALK3 precursor protein is provided in FIG. 1. The extracellular domain of an ALK3 protein binds to BMP and is generally soluble, and thus can be termed a soluble, BMP-binding ALK3 polypeptide. Examples of soluble, BMP-binding ALK3 polypeptides include the soluble polypeptide illustrated in SEQ ID NOs: 3, 7, 11, 14, 20, 22, 23, 25, 26, 28, 29, 30, 31, 33, 34, 35, 36, 38, 39, 40, or 41. SEQ ID NO:7 is referred to as ALK3(24-152)-hFc, and is described further in the Examples. Other examples of soluble, BMP-binding ALK3 polypeptides comprise a signal sequence in addition to the extracellular domain of an ALK3 protein, for example, the native ALK3 leader sequence (SEQ ID NO: 8), the tissue plaminogen activator (TPA) leader (SEQ ID NO: 9) or the honey bee melittin leader (SEQ ID NO: 10). The ALK3-hFc polypeptide illustrated in SEQ ID NO: 11 uses a TPA leader.

Functionally active fragments of ALK3 polypeptides can be obtained by screening polypeptides recombinantly produced from the corresponding fragment of the nucleic acid encoding an ALK3 polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ALK3 protein or signaling mediated by BMPs.

Functionally active variants of ALK3 polypeptides can be obtained by screening libraries of modified polypeptides recombinantly produced from the corresponding mutagenized nucleic acids encoding an ALK3 polypeptide. The variants can be produced and tested to identify those that can function as antagonists (inhibitors) of ALK3 protein or signaling mediated by BMPs. In certain embodiments, a functional variant of the ALK3 polypeptides comprises an amino acid sequence that is at least 75% identical to an amino acid sequence selected from SEQ ID NO: 3, 7, 11, 14, 20, 22, 23, 25, 26, 28, 29, 30, 31, 33, 34, 35, 36, 38, 39, 40, or 41. In certain cases, the functional variant has an amino acid sequence at least 80%, 85%, 90%, 95%, 97%, 98%, 99% or 100% identical to an amino acid sequence selected from SEQ ID NO: 3, 7, 11, 14, 20, 22, 23, 25, 26, 28, 29, 30, 31, 33, 34, 35, 36, 38, 39, 40, or 41.

Functional variants may be generated by modifying the structure of an ALK3 polypeptide for such purposes as enhancing therapeutic efficacy, or stability (e.g., ex vivo shelf life and resistance to proteolytic degradation in vivo). Such modified ALK3 polypeptides, when selected to retain BMP binding, are considered functional equivalents of the naturally-occurring ALK3 polypeptides. Modified ALK3 polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ALK3 polypeptide results in a functional homolog can be readily determined by assessing the ability of the variant ALK3 polypeptide to produce a response in cells in a fashion similar to the wild-type ALK3 polypeptide.

In certain embodiments, the present invention contemplates specific mutations of the ALK3 polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagines-X-serine) (where "X" is any amino acid) which is specifically recognized by appropriate cellular glycosylation enzymes. The alteration may also be made by the addition of, or substitution by, one or more serine or threonine residues to the sequence of the wild-type ALK3 polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ALK3 polypeptide is by chemical or enzymatic coupling of glycosides to the ALK3 polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ALK3 polypeptide may be accomplished chemically and/or enzymatically. Chemical deglycosylation may involve, for example, exposure of the ALK3 polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ALK3 polypeptides can be achieved by the use of a variety of endo- and exo-glycosidases as described by Thotakura et al. (1987) Meth. Enzymol. 138:350. The sequence of an ALK3 polypeptide may be adjusted, as appropriate, depending on the type of expression system used, as mammalian, yeast, insect and plant cells may all introduce differing glycosylation patterns that can be affected by the amino acid sequence of the peptide. In general, ALK3 proteins for use in humans will be expressed in a mammalian cell line that provides proper glycosylation, such as HEK293 or CHO cell lines, although other mammalian expression cell lines, yeast cell lines with engineered glycosylation enzymes and insect cells are expected to be useful as well.

This disclosure further contemplates a method of generating mutants, particularly sets of combinatorial mutants of an ALK3 polypeptide, as well as truncation mutants; pools of combinatorial mutants are especially useful for identifying functional variant sequences. The purpose of screening such combinatorial libraries may be to generate, for example, ALK3 polypeptide variants which can act as either agonists or antagonist, or alternatively, which possess novel activities altogether. A variety of screening assays are provided below, and such assays may be used to evaluate variants. For example, an ALK3 polypeptide variant may be screened for ability to bind to an ALK3 ligand, to prevent binding of an ALK3 ligand to an ALK3 polypeptide or to interfere with signaling caused by an ALK3 ligand.

The activity of an ALK3 polypeptide or its variants may also be tested in a cell-based or in vivo assay. For example, the effect of an ALK3 polypeptide variant on the expression of genes involved in bone production or bone destruction may be assessed. This may, as needed, be performed in the presence of one or more recombinant ALK3 ligand proteins (e.g., BMP2 or BMP4), and cells may be transfected so as to produce an ALK3 polypeptide and/or variants thereof, and optionally, an ALK3 ligand. Likewise, an ALK3 polypeptide may be administered to a mouse or other animal, and one or more bone properties, such as density or volume may be assessed. The healing rate for bone fractures may also be evaluated. Dual-energy x-ray absorptiometry (DEXA) is a well-established, non-invasive, quantitative technique for assessing bone density in an animal. In humans, central DEXA systems may be used to evaluate bone density in the spine and pelvis. These are the best predictors of overall bone density. Peripheral DEXA systems may be used to evaluate bone density in peripheral bones, including, for example, the bones of the hand, wrist, ankle and foot. Traditional x-ray imaging systems, including CAT scans, may be used to evaluate bone growth and fracture healing. The mechanical strength of bone may also be evaluated.

Combinatorially-derived variants can be generated which have a selective or generally increased potency relative to a naturally occurring ALK3 polypeptide. Likewise, mutagenesis can give rise to variants which have intracellular half-lives dramatically different than the corresponding a wild-type ALK3 polypeptide. For example, the altered protein can be rendered either more stable or less stable to proteolytic degradation or other cellular processes which result in destruction of, or otherwise inactivation of a native ALK3 polypeptide. Such variants, and the genes which encode them, can be utilized to alter ALK3 polypeptide levels by modulating the half-life of the ALK3 polypeptides. For instance, a short half-life can give rise to more transient biological effects and can allow tighter control of recombinant ALK3 polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ALK3 polypeptide sequences. For instance, a mixture of synthetic oligonucleotides can be enzymatically ligated into gene sequences such that the degenerate set of potential ALK3 polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ALK3 polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ALK3 polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ALK3 polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include BMP binding assays and BMP-mediated cell signaling assays.

In certain embodiments, the ALK3 polypeptides of the invention may further comprise post-translational modifications in addition to any that are naturally present in the ALK3 polypeptides. Such modifications include, but are not limited to, acetylation, carboxylation, glycosylation, phosphorylation, lipidation, and acylation. As a result, the modified ALK3 polypeptides may contain non-amino acid elements, such as polyethylene glycols, lipids, poly- or mono-saccharide, and phosphates. Effects of such non-amino acid elements on the functionality of an ALK3 polypeptide may be tested as described herein for other ALK3 polypeptide variants. When an ALK3 polypeptide is produced in cells by cleaving a nascent form of the ALK3 polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ALK3 polypeptides.

In certain aspects, functional variants or modified forms of the ALK3 polypeptides include fusion proteins having at least a portion of the ALK3 polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt- conjugated resins are used. Many of such matrices are available in "kit" form, such as the Pharmacia GST purification system and the QlAexpress™ system (Qiagen) useful with (HIS$_6$(SEQ ID NO: 47)) fusion partners. As another example, a fusion domain may be selected so as to facilitate detection of the ALK3 polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ALK3 polypeptide is fused with a domain that stabilizes the ALK3 polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth or muscle growth, as desired).

As a specific example, the present invention provides a fusion protein comprising a soluble extracellular domain of ALK3 fused to an Fc domain (e.g., SEQ ID NO: 5 in FIG. 5). Examples of Fc domains are shown below:

```
                                            (SEQ ID NO: 48)
THTCPPCPAPELLGGPSVFLFPPKPKDTLMISRTPEVTCVVVD (A)VSHEDPEVKFNWYVDGVEVHNAKTKPREEQYNSTYRVVSV

LTVLHQDWLNGKEYKCK(A)VSNKALPVPIEKTISKAKGQPRE

PQVYTLPPSREEMTKNQVSLTCLVKGFYPSDIAVEWESNGQPE

NNYKTTPPVLDSDGPFFLYSKLTVDKSRWQQGNVFSCSVMHEA

LHN(A)HYTQKSLSLSPGK*
```

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, an ALK3 polypeptide may be placed C-terminal to a heterologous domain, or, alternatively, a heterologous domain may be placed C-terminal to an ALK3 polypeptide. The ALK3 polypeptide domain and the heterologous domain need not be adjacent in a fusion protein, and additional domains or amino acid sequences may be included C- or N-terminal to either domain or between the domains.

In certain embodiments, the ALK3 polypeptides of the present invention contain one or more modifications that are capable of stabilizing the ALK3 polypeptides. For example, such modifications enhance the in vitro half life of the ALK3 polypeptides, enhance circulatory half life of the ALK3 polypeptides or reduce proteolytic degradation of the ALK3 polypeptides. Such stabilizing modifications include, but are not limited to, fusion proteins (including, for example, fusion proteins comprising an ALK3 polypeptide and a stabilizer domain), modifications of a glycosylation site (including, for example, addition of a glycosylation site to an ALK3 polypeptide), and modifications of carbohydrate moiety (including, for example, removal of carbohydrate moieties from an ALK3 polypeptide). In the case of fusion proteins, an ALK3 polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the ALK3 polypeptides, which are isolated from, or otherwise substantially free of, other proteins. ALK3 polypeptides will generally be produced by expression from recombinant nucleic acids.

3. Nucleic Acids Encoding ALK3 Polypeptides

In certain aspects, the invention provides isolated and/or recombinant nucleic acids encoding any of the ALK3 polypeptides (e.g., soluble ALK3 polypeptides), including fragments, functional variants and fusion proteins disclosed herein. For example, SEQ ID NO: 2 encodes the naturally occurring human ALK3 precursor polypeptide, while SEQ ID NO: 4 encodes the processed extracellular domain of ALK3. The subject nucleic acids may be single-stranded or double stranded. Such nucleic acids may be DNA or RNA molecules. These nucleic acids may be used, for example, in methods for making ALK3 polypeptides or as direct therapeutic agents (e.g., in a gene therapy approach).

In certain aspects, the subject nucleic acids encoding ALK3 polypeptides are further understood to include nucleic acids that are variants of SEQ ID NO: 2 or 4. Variant nucleotide sequences include sequences that differ by one or more nucleotide substitutions, additions or deletions, such as allelic variants.

In certain embodiments, the invention provides isolated or recombinant nucleic acid sequences that are at least 80%, 85%, 90%, 95%, 97%, 98%, 99% or 100% identical to SEQ ID NO: 2, 4, 12, 13, 15, 16, 19, 21, 24, 27, 32 or 37. One of ordinary skill in the art will appreciate that nucleic acid sequences complementary to SEQ ID NO: 2, 4, 12, 13, 15, 16, 19, 21, 24, 27, 32 or 37 and variants of SEQ ID NO: 2, 4, 12, 13, 15, 16, 19, 21, 24, 27, 32 or 37 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 2, 4, 12, 13, 15, 16, 19, 21, 24, 27, 32 or 37, complement sequence of SEQ ID NO: 2, 4, 12, 13, 15, 16, 19, 21, 24, 27, 32 or 37, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0× SSC at 50° C. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6× SSC at room temperature followed by a wash at 2× SSC at room temperature.

Isolated nucleic acids which differ from the nucleic acids as set forth in SEQ ID NOs: 2, 4, 12, 13, 15, 16, 19, 21, 24, 27, 32 or 37 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ALK3 polypeptide and operably linked to at least one regulatory sequence. Regulatory sequences are art-recognized and are selected to direct expression of the ALK3 polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ALK3 polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant ALK3 polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ALK3 polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ALK3 polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO: 2, 4, 12, 13, 15, 16, 19, 21, 24, 27, 32 or 37) for one or more of the subject ALK3 polypeptides. The host cell may be any prokaryotic or eukaryotic cell. For example, an ALK3 polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject ALK3 polypeptides. For example, a host cell transfected with an expression vector encoding an ALK3 polypeptide can be cultured under appropriate conditions to allow expression of the ALK3 polypeptide to occur. The ALK3 polypeptide may be secreted and isolated from a mixture of cells and medium containing the ALK3 polypeptide. Alternatively, the ALK3 polypeptide may be retained cytoplasmically or in a membrane fraction and the cells harvested, lysed and the protein isolated. A cell culture includes host cells, media and other byproducts. Suitable media for cell culture are well known in the art. The subject ALK3 polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ALK3 polypeptides and affinity purification with an agent that binds to a domain fused to the ALK3 polypeptide (e.g., a protein A column may be used to purify an ALK3-Fc fusion). In a preferred embodiment, the ALK3 polypeptide is a fusion protein containing a domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ALK3-hFc protein was purified to a purity of >98% as determined by size exclusion chromatography and >95% as determined by SDS PAGE. This level of purity was sufficient to achieve desirable effects on bone in mice and an acceptable safety profile in mice, rats and non-human primates.

In another embodiment, a fusion gene coding for a purification leader sequence, such as a poly-(His)/enterokinase cleavage site sequence at the N-terminus of the desired portion of the recombinant ALK3 polypeptide, can allow purification of the expressed fusion protein by affinity chromatography using a $Ni^{2+}$ metal resin. The purification leader sequence can then be subsequently removed by treatment with enterokinase to provide the purified ALK3 polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Alternative BMP and ALK3 Antagonists

The data presented herein demonstrates that antagonists of BMP-ALK3 signaling can be used to promote bone growth and bone mineralization. Although soluble ALK3 polypeptides, and particularly ALK3-Fc, are preferred antagonists, and although such antagonists may affect bone through a mechanism other than BMP antagonism (e.g., BMP inhibition may be an indicator of the tendency of an agent to inhibit the activities of a spectrum of molecules, including, perhaps, other members of the TGF-beta superfamily, and such collective inhibition may lead to the desired effect on bone), other types of BMP-ALK3 antagonists are expected to be useful, including anti-BMP (e.g., BMP2 or BMP4) antibodies, anti-ALK3 antibodies, antisense, RNAi or ribozyme nucleic acids that inhibit the production of ALK3, BMP2 or BMP4 and other inhibitors of BMP or ALK3, particularly those that disrupt BMP-ALK3 binding.

An antibody that is specifically reactive with an ALK3 polypeptide (e.g., a soluble ALK3 polypeptide) and which either binds competitively to ligand with the ALK3 polypeptide or otherwise inhibits ALK3-mediated signaling may be used as an antagonist of ALK3 polypeptide activities. Likewise, an antibody that is specifically reactive with an BMP polypeptide and which disrupts ALK3 binding may be used as an antagonist.

By using immunogens derived from an ALK3 polypeptide or a BMP polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ALK3 polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ALK3 or BMP polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ALK3 polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ALK3 polypeptide and monoclonal antibodies isolated from a culture comprising such hybridoma cells.

The term "antibody" as used herein is intended to include fragments thereof which are also specifically reactive with a subject polypeptide. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, chimeric, humanized and fully human molecules having affinity for an ALK3 or BMP polypeptide conferred by at least one CDR region of the antibody. An antibody may further comprise a label attached thereto and able to be detected (e.g., the label can be a radioisotope, fluorescent compound, enzyme or enzyme co-factor).

In certain embodiments, the antibody is a recombinant antibody, which term encompasses any antibody generated in part by techniques of molecular biology, including CDR-grafted or chimeric antibodies, human or other antibodies assembled from library-selected antibody domains, single chain antibodies and single domain antibodies (e.g., human $V_H$ proteins or camelid $V_{HH}$ proteins). In certain embodiments, an antibody of the invention is a monoclonal antibody, and in certain embodiments, the invention makes available methods for generating novel antibodies. For example, a method for generating a monoclonal antibody that binds specifically to an ALK3 polypeptide or BMP polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ALK3 polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less. Given the extraordinarily tight binding between BMPs and ALK3, it is expected that a neutralizing anti-BMP or anti-ALK3 antibody would generally have a dissociation constant of $10^{-9}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

Examples of categories of nucleic acid compounds that are BMP or ALK3 antagonists include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50, 35, 30, 25, 22, 20 or 18 nucleotides of the full-length ALK3 nucleic acid sequence or BMP nucleic acid sequence. The region of complementarity will preferably be at least 8 nucleotides, and optionally at least 10 or at least 15 nucleotides, and optionally between 15 and 25 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA or any other variation. The duplex portion of double stranded or single stranded "hairpin" RNAi construct will preferably have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, bone growth and mineralization.

5. Screening Assays

In certain aspects, the present invention relates to the use of ALK3 polypeptides (e.g., soluble ALK3 polypeptides) and BMP polypeptides to identify compounds (agents) which are agonist or antagonists of the BMP-ALK3 signaling pathway. Compounds identified through this screening can be tested to assess their ability to modulate bone growth or mineralization in vitro. Optionally, these compounds can further be tested in animal models to assess their ability to modulate tissue growth in vivo.

There are numerous approaches to screening for therapeutic agents for modulating tissue growth by targeting BMPs and ALK3 polypeptides. In certain embodiments, high-throughput screening of compounds can be carried out to identify agents that perturb BMPs or ALK3-mediated effects on bone. In certain embodiments, the assay is carried out to screen and identify compounds that specifically inhibit or reduce binding of an ALK3 polypeptide to BMPs. Alternatively, the assay can be used to identify compounds that enhance binding of an ALK3 polypeptide to BMPs. In a further embodiment, the compounds can be identified by their ability to interact with a BMP or ALK3 polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ALK3 polypeptide and BMPs.

Merely to illustrate, in an exemplary screening assay of the present invention, the compound of interest is contacted with an isolated and purified ALK3 polypeptide which is ordinarily capable of binding to BMPs. To the mixture of the compound and ALK3 polypeptide is then added a composition containing an ALK3 ligand. Detection and quantification of ALK3/BMP complexes provides a means for determining the compound's efficacy at inhibiting (or potentiating) complex formation between the ALK3 polypeptide and BMPs. The efficacy of the compound can be assessed by generating dose response curves from data obtained using various concentrations of the test compound. Moreover, a control assay can also be performed to provide a baseline for comparison. For example, in a control assay, isolated and a purified BMP is added to a composition containing the ALK3 polypeptide, and the formation of ALK3/BMP complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ALK3 polypeptide and BMPs may be detected by a variety of techniques. For instance, modulation of the formation of complexes can be quantitated using, for example, detectably labeled proteins such as radiolabeled (e.g., $^{32}P$, $^{35}S$, $_{14}C$ or $^{3}H$), fluorescently labeled (e.g., FITC), or enzymatically labeled ALK3 polypeptide or BMPs, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between an ALK3 polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between an ALK3 polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between an ALK3 polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with an ALK3 or BMP polypeptide of the invention. The interaction between the compound and the ALK3 or BMP polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a BMP or ALK3 polypeptide. This may include a solid phase or fluid phase binding event. Alternatively, the gene encoding a BMP or ALK3 polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for modulating (stimulating or inhibiting) bone formation and increasing bone mass. Therefore, any compound identified can be tested in whole cells or tissues, in vitro or in vivo, to confirm their ability to modulate bone growth or mineralization. Various methods known in the art can be utilized for this purpose.

For example, the effect of the ALK3 or BMP polypeptides or test compounds on bone or cartilage growth can be determined by measuring induction of Msx2 or differentiation of osteoprogenitor cells into osteoblasts in cell based assays (see, e.g., Daluiski et al., Nat Genet. 2001, 27(1):84-8; Hino et al., Front Biosci. 2004, 9:1520-9). Another example of cell-based assays includes analyzing the osteogenic activity of the subject ALK3 or BMP polypeptides and test compounds in mesenchymal progenitor and osteoblastic cells. To illustrate, recombinant adenoviruses expressing a BMP or ALK3 polypeptide can be constructed to infect pluripotent mesenchymal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8):1544-52).

The present invention also contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. Andersson et al., J. Endocrinol. 170:529-537 describe a mouse osteoporosis model in which mice are ovariectomized, which causes the mice to lose substantial bone mineral content and bone mineral density, with the trabecular bone losing roughly 50% of bone mineral density. Bone density could be increased in the ovariectomized mice by administration of factors such as parathyroid hormone. In certain aspects, the present invention makes use of fracture healing assays that are known in the art. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

6. Exemplary Therapeutic Uses

In certain embodiments, BMP-ALK3 antagonists (e.g., ALK3 polypeptides) of the present invention can be used for treating or preventing a disease or condition that is associated with bone damage, whether, e.g., through breakage, loss or demineralization. In certain embodiments, the present invention provides methods of treating or preventing bone damage in an individual in need thereof through administering to the individual a therapeutically effective amount of an BMP-ALK3 antagonist, particularly an ALK3 polypeptide. Given the potential for a dual effect on bone resorption and formation, such compounds may be useful in a wide range of diseases that are currently treated with anabolic (e.g., parathyroid hormone and derivatives thereof) or anti-resorptive agents (e.g., bisphosphonates). In certain embodiments, the present invention provides methods of promoting bone growth or mineralization in an individual in need thereof through administering to the individual a therapeutically effective amount of a BMP-ALK3 antagonist, particularly an ALK3 polypeptide. These methods are optionally aimed at therapeutic and prophylactic treatments of animals, and more preferably, humans. In certain embodiments, the disclosure provides for the use of BMP-ALK3 antagonists (particularly soluble ALK3 polypeptides and neutralizing antibodies targeted to BMPs or ALK3) for the treatment of disorders associated with low bone density or decreased bone strength.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established. In either case, prevention or treatment may be discerned in the diagnosis provided by a physician and the intended result of administration of the therapeutic agent.

The disclosure provides methods of inducing bone and/or cartilage formation, preventing bone loss, increasing bone mineralization or preventing the demineralization of bone. For example, the subject BMP-ALK3 antagonists have application in treating bone loss disorders, such as osteoporosis and the healing of bone fractures and cartilage defects or other bone defects, injuries and disorders in humans and other animals. ALK3 or BMP polypeptides may be useful in patients that are diagnosed with subclinical low bone density, as a protective measure against the development of osteoporosis.

In one specific embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. In certain cases, the subject BMP-ALK3 antagonists may provide an environment to attract bone-forming cells, stimulate growth of bone-forming cells or induce differentiation of progenitors of bone-forming cells. BMP-ALK3 antagonists of the invention may also be useful in the treatment of osteoporosis.

Rosen et al. (ed) Primer on the Metabolic Bone Diseases and Disorders of Mineral Metabolism, 7$^{th}$ ed. American Society for Bone and Mineral Research, Washington D.C. (incorporated herein by reference) provides an extensive discussion of bone disorders that may be subject to treatment with ALK3-BMP antagonists. A partial listing is provided herein. Methods and compositions of the invention can be applied to conditions characterized by or causing bone loss, such as osteoporosis (including secondary osteoporosis), hyperparathyroidism, chronic kidney disease mineral bone disorder, sex hormone deprivation or ablation (e.g. androgen and/or estrogen), glucocorticoid treatment, rheumatoid arthritis, severe burns, hyperparathyroidism, hypercalcemia, hypocalcemia, hypophosphatemia, osteomalacia (including tumor-induced osteomalacia), hyperphosphatemia, vitamin D deficiency, hyperparathyroidism (including familial hyperparathyroidism) and pseudohypoparathyroidism, tumor metastases to bone, bone loss as a consequence of a tumor or chemotherapy, tumors of the bone and bone marrow (e.g., multiple myeloma), ischemic bone disorders, periodontal disease and oral bone loss, Cushing's disease, Paget's disease, thyrotoxicosis, chronic diarrheal state or malabsorption, renal tubular acidosis, or anorexia nervosa. Methods and compositions of the invention may also be applied to conditions characterized by a failure of bone formation or healing, including non-union fractures, fractures that are otherwise slow to heal, fetal and neonatal bone dysplasias (e.g., hypocalcemia, hypercalcemia, calcium receptor defects and vitamin D deficiency), osteonecrosis (including osteonecrosis of the jaw) and osteogenesis imperfecta. Additionally, the anabolic effects will cause such antagonists to diminish bone pain associated with bone damage or erosion. As a consequence of the anti-resorptive effects, such antagonists may be useful to treat disorders of abnormal bone formation, such as osteoblastic tumor metastases (e.g., associated with primary prostate or breast cancer), osteogenic osteosarcoma, osteopetrosis, progressive diaphyseal dysplasia, endosteal hyperostosis, osteopoikilosis, and melorheostosis. Other disorders that may be treated include fibrous dysplasia and chondrodysplasias.

In addition to the foregoing discussion, persons having any of the following profiles may be candidates for treatment with an ALK3 antagonist: a post-menopausal woman and not taking estrogen or other hormone replacement therapy; a person with a personal or maternal history of hip fracture or smoking; a post-menopausal woman who is tall (over 5 feet 7 inches) or thin (less than 125 pounds); a man with clinical conditions associated with bone loss; a person using medications that are known to cause bone loss, including corticosteroids such as Prednisone™, various anti-seizure medications such as Dilantin™ and certain barbiturates, or high-dose thyroid replacement drugs; a person having type 1 diabetes, liver disease, kidney disease, a family history of osteoporosis; a person having high bone turnover (e.g., excessive collagen in urine samples); a person with a thyroid condition, such as hyperthyroidism; a person who has experienced a fracture after only mild trauma; a person who has had x-ray evidence of vertebral fracture or other signs of osteoporosis.

Osteoporosis (meaning, generally speaking, a state of low bone density or strength) may be caused by, or associated with, various factors. Being female, particularly a post-menopausal female, having a low body weight, and leading a sedentary lifestyle are all risk factors for osteoporosis (loss of bone mineral density, leading to fracture risk).

Osteoporosis can also result as a condition associated with another disorder or from the use of certain medications. Osteoporosis resulting from drugs or another medical condition is known as secondary osteoporosis. In a condition known as Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenytoin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Bone loss resulting from cancer therapy is widely recognized and termed cancer therapy induced bone loss (CTIBL). Bone metastases can create cavities in the bone that may be corrected by treatment with BMP-ALK3 antagonists.

Optionally, BMP-ALK3 antagonists, particularly a soluble ALK3, disclosed herein may be used in cancer patients. Patients having certain tumors (e.g. prostate, breast, multiple myeloma or any tumor causing hyperparathyroidism) are at high risk for bone loss due to tumor-induced bone loss as well as bone metastases and therapeutic agents. Such patients may be treated with BMP-ALK3 antagonists even in the absence of evidence of bone loss or bone metastases. Patients may also be monitored for evidence of bone loss or bone metastases, and may be treated with BMP-ALK3 antagonists in the event that indicators suggest an increased risk. Generally, DEXA scans are employed to assess changes in bone density, while indicators of bone remodeling may be used to assess the likelihood of bone metastases. Serum markers may be monitored. Bone specific alkaline phosphatase (BSAP) is an enzyme that is present in osteoblasts. Blood levels of BSAP are increased in patients with bone metastasis and other conditions that result in increased bone remodeling. Osteocalcin and procollagen peptides are also associated with bone formation and bone metastases. Increases in BSAP have been detected in patients with bone metastasis caused by prostate cancer, and to a lesser degree, in bone metastases from breast cancer. Bone Morphogenetic Protein-7 (BMP-7) levels are high in prostate cancer that has metastasized to bone, but not in bone metastases due to bladder, skin, liver, or lung cancer. Type I Carboxy-terminal telopeptide (ICTP) is a crosslink found in collagen that is formed during the resorption of bone. Since bone is constantly being broken down and reformed, ICTP will be found throughout the body. However, at the site of bone metastasis, the level will be significantly higher than in an area of normal bone. ICTP has been found in high levels in bone metastasis due to prostate, lung, and breast cancer. Another collagen crosslink, Type I N-terminal telopeptide (NTx), is produced along with ICTP during bone turnover. The amount of NTx is increased in bone metastasis caused by many different types of cancer including lung, prostate, and breast cancer. Also, the levels of NTx increase with the progression of the bone metastasis. Therefore, this marker can be used to both detect metastasis as well as measure the extent of the disease. Other markers of resorption include pyridinoline and deoxypyridinoline. Any increase in resorption markers or markers of bone metastases indicate the need for BMP-ALK3 antagonist therapy in a patient.

In another embodiment, BMP-ALK3 antagonists may be used in patients with chronic kidney disease mineral bone disorder (CKD-MBD), a broad syndrome of interrelated skeletal, cardiovascular, and mineral-metabolic disorders arising from kidney disease. CKD-MBD encompasses various skeletal pathologies often referred to as renal osteodystrophy (ROD), which is a preferred embodiment for treatment with BMP-ALK3 antagonists. Depending on the relative contribution of diffent pathogenic factors, ROD is manifested as diverse pathologic patterns of bone remodeling (Hruska et al., 2008, Chronic kidney disease mineral bone disorder (CKD-MBD); in Rosen et al. (ed) Primer on the Metabolic Bone Diseases and Disorders of Mineral Metabolism, $7^{th}$ ed. American Society for Bone and Mineral Research, Washington D.C., pp 343-349). At one end of the spectrum is ROD with uremic osteodystrophy and low bone turnover, characterized by a low number of active remodeling sites, profoundly suppressed bone formation, and low bone resorption. At the other extreme is ROD with hyperparathyroidism, high bone turnover, and osteitis fibrosa. Given that BMP-ALK3 antagonists exert both anabolic and antiresorptive effects, these agents may be useful in patients across the ROD pathology spectrum.

BMP-ALK3 antagonists may be conjointly administered with other pharmaceutical agents. Conjoint administration may be accomplished by administration of a single co-formulation, by simultaneous administration or by administration at separate times. BMP-ALK3 antagonists may be particularly advantageous if administered with other bone-active agents. A patient may benefit from conjointly receiving BMP-ALK3 antagonist and taking calcium supplements, vitamin D, appropriate exercise and/or, in some cases, other medication. Examples of other medications incude, bisphosphonates (alendronate, ibandronate and risedronate), calcitonin, estrogens, parathyroid hormone and raloxifene. The bisphosphonates (alendronate, ibandronate and risedronate), calcitonin, estrogens and raloxifene affect the bone remodeling cycle and are classified as anti-resorptive medications. Bone remodeling consists of two distinct stages: bone resorption and bone formation. Anti-resorptive medications slow or stop the bone-resorbing portion of the bone-remodeling cycle but do not slow the bone-forming portion of the cycle. As a result, new formation continues at a greater rate than bone resorption, and bone density may increase over time. Teriparatide, a form of parathyroid hormone, increases the rate of bone formation in the bone remodeling cycle. Alendronate is approved for both the prevention (5 mg per day or 35 mg once a week) and treatment (10 mg per day or 70 mg once a week) of postmenopausal osteoporosis. Alendronate reduces bone loss, increases bone density and reduces the risk of spine, wrist and hip fractures. Alendronate also is approved for treatment of glucocorticoid-induced osteoporosis in men and women as a result of long-term use of these medications (i.e., prednisone and cortisone) and for the treatment of osteoporosis in men. Alendronate plus vitamin D is approved for the treatment of osteoporosis in postmenopausal women (70 mg once a week plus vitamin D), and for treatment to improve bone mass in men with osteoporosis. Ibandronate is approved for the prevention and treatment of postmenopausal osteoporosis. Taken as a once-a-month pill (150 mg), ibandronate should be taken on the same day each month. Ibandronate reduces bone loss, increases bone density and reduces the risk of spine fractures. Risedronate is approved for the prevention and treatment of postmenopausal osteoporosis. Taken daily (5 mg dose) or weekly (35 mg dose or 35 mg dose with calcium), risedronate slows bone loss, increases bone density and reduces the risk of spine and non-spine fractures. Risedronate also is approved for use by men and women to prevent and/or treat glucocorticoid-induced osteoporosis that results from long-term use of these medications (i.e., prednisone or cortisone). Calcitonin is a naturally occurring hormone involved in calcium regulation and bone metabolism. In women who are more than 5 years beyond menopause, calcitonin slows bone loss, increases spinal bone density, and may relieve the pain associated with bone fractures. Calcitonin reduces the risk of spinal fractures. Calcitonin is available as an injection (50-100 IU daily) or nasal spray (200 IU daily). Estrogen therapy (ET)/Hormone therapy (HT) is approved for the prevention of osteoporosis. ET has been shown to reduce bone loss, increase bone density in both the spine and hip, and reduce the risk of hip and spinal fractures in postmenopausal women. ET is administered most commonly in the form of a pill or skin patch that delivers a low dose of approximately 0.3 mg daily or a standard dose of approximately 0.625 mg daily and is effective even when started after age 70. When estrogen is taken alone, it can increase a woman's risk of developing cancer of the uterine lining (endometrial cancer). To eliminate this risk, healthcare providers prescribe the hormone progestin in combination with estrogen (hormone replacement therapy or HT) for those women who have an intact uterus. ET/HT relieves menopause symptoms and has been shown to have a beneficial effect on bone health. Side effects may include vaginal bleeding, breast tenderness, mood disturbances and gallbladder disease. Raloxifene, 60 mg a day, is approved for the prevention and treatment of postmenopausal osteoporosis. It is from a class of drugs called Selective Estrogen Receptor Modulators (SERMs) that have been developed to provide the beneficial effects of estrogens without their potential disadvantages. Raloxifene increases bone mass and reduces the risk of spine fractures. Data are not yet available to demonstrate that raloxifene can reduce the risk of hip and other non-spine fractures. Teriparatide, a form of parathyroid hormone, is approved for the treatment of osteoporosis in postmenopausal women and men who are at high risk for a fracture. This medication stimulates new bone formation and significantly increases bone mineral density. In postmenopausal women, fracture reduction was noted in the spine, hip, foot, ribs and wrist. In men, fracture reduction was noted in the spine, but there were insufficient data to evaluate fracture reduction at other sites. Teriparatide is self-administered as a daily injection for up to 24 months.

7. Pharmaceutical Compositions

In certain embodiments, BMP-ALK3 antagonists (e.g., ALK3 polypeptides) of the present invention are formulated with a pharmaceutically acceptable carrier. For example, an ALK3 polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition systemically, or locally as an implant or device. When administered, the therapeutic composition for use in this invention is, of course, in a pyrogen-free, physiologically acceptable form. Therapeutically useful agents other than the ALK3 antagonists which may also optionally be included in the composition as described above, may be administered simultaneously or sequentially with the subject compounds (e.g., ALK3 polypeptides) in the methods of the invention.

Typically, ALK3 antagonists will be administered parentally. Pharmaceutical compositions suitable for parenteral administration may comprise one or more ALK3 polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone). In certain embodiments, compositions of the present invention may include a matrix capable of delivering one or more therapeutic compounds (e.g., ALK3 polypeptides) to a target tissue site (e.g., bone), providing a structure for the developing tissue and optimally capable of being resorbed into the body. For example, the matrix may provide slow release of the ALK3 polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ALK3 polypeptides). The various factors include, but are not limited to, amount of bone weight desired to be formed, the degree of bone density loss, the site of bone damage, the condition of the damaged bone, the patient's age, sex, and diet, the severity of any disease that may be contributing to bone loss, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, the present invention also provides gene therapy for the in vivo production of ALK3 polypeptides. Such therapy would achieve its therapeutic effect by introduction of the ALK3 polynucleotide sequences into cells or tissues having the disorders as listed above. Delivery of ALK3 polynucleotide sequences can be achieved using a recombinant expression vector such as a chimeric virus or a colloidal dispersion system. Preferred for therapeutic delivery of ALK3 polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes.

All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ALK3 polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ALK3 polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebro sides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

Exemplification

The invention now being generally described, it will be more readily understood by reference to the following examples, which are included merely for purposes of illustration of certain embodiments of the present invention, and are not intended to limit the invention.

EXAMPLE 1

Generation of ALK3-Fc Fusion Proteins

The amino acid sequence and corresponding nucleotide sequence for native human ALK3 are shown in FIGS. 1, 2. Applicants designed an ALK3-hFc fusion protein in which the extracellular domain (native residues 24-152) of human ALK3 (FIGS. 3, 4) is fused C-terminally with a human Fc domain (FIGS. 5, 6) via a minimal linker (comprised of amino acid residues TGGG (SEQ ID NO: 42)) to yield the protein shown in FIG. 7. The following three leader sequences were considered:

(i) Native:
(SEQ ID NO: 8)
MPQLYIYIRLLGAYLFIISRVQG (ii) Tissue plasminogen activator (TPA):
(SEQ ID NO: 9)
MDAMKRGLCCVLLLCGAVFVSP (iii) Honey bee melittin (HBML):
(SEQ ID NO: 10)
MKFLVNVALVFMVVYISYIYA The selected form of hALK3(24-152)-hFc (SEQ ID NO: 11) employs the TPA leader and has the unprocessed amino-acid sequence shown in FIG. 8. A sense nucleotide sequence encoding this fusion protein and the corresponding antisense sequence are indicated in FIG. 9. Shown below is an alternative sense nucleotide sequence encoding hALK3(24-152)-hFc, which incorporates a C→T substitution at position 1137 (underlined) that does not alter the amino acid sequence.

```
                                            (SEQ ID NO: 19)
   1 ATGGATGCAA TGAAGAGAGG GCTCTGCTGT GTGCTGCTGC

41 TGTGTGGAGC AGTCTTCGTT TCGCCCGGCG CCCAGAATCT

81 GGATAGTATG CTTCATGGCA CTGGGATGAA ATCAGACTCC

121 GACCAGAAAA AGTCAGAAAA TGGAGTAACC TTAGCACCAG

161 AGGATACCTT GCCTTTTTTA AAGTGCTATT GCTCAGGGCA

201 CTGTCCAGAT GATGCTATTA ATAACACATG CATAACTAAT

241 GGACATTGCT TTGCCATCAT AGAAGAAGAT GACCAGGGAG

281 AAACCACATT AGCTTCAGGG TGTATGAAAT ATGAAGGATC

321 TGATTTTCAG TGCAAAGATT CTCCAAAAGC CCAGCTACGC

361 CGGACAATAG AATGTTGTCG GACCAATTTA TGTAACCAGT

401 ATTTGCAACC CACACTGCCC CCTGTTGTCA TAGGTCCGTT

441 TTTTGATGGC AGCATTCGAA CCGGTGGTGG AACTCACACA

481 TGCCCACCGT GCCCAGCACC TGAACTCCTG GGGGGACCGT

521 CAGTCTTCCT CTTCCCCCCA AAACCCAAGG ACACCCTCAT

561 GATCTCCCGG ACCCCTGAGG TCACATGCGT GGTGGTGGAC

601 GTGAGCCACG AAGACCCTGA GGTCAAGTTC AACTGGTACG

641 TGGACGGCGT GGAGGTGCAT AATGCCAAGA CAAAGCCGCG

681 GGAGGAGCAG TACAACAGCA CGTACCGTGT GGTCAGCGTC

721 CTCACCGTCC TGCACCAGGA CTGGCTGAAT GGCAAGGAGT

761 ACAAGTGCAA GGTCTCCAAC AAAGCCCTCC CAGCCCCCAT

801 CGAGAAAACC ATCTCCAAAG CCAAAGGGCA GCCCCGAGAA

841 CCACAGGTGT ACACCCTGCC CCCATCCCGG GAGGAGATGA

881 CCAAGAACCA GGTCAGCCTG ACCTGCCTGG TCAAAGGCTT

921 CTATCCCAGC GACATCGCCG TGGAGTGGGA GAGCAATGGG

961 CAGCCGGAGA ACAACTACAA GACCACGCCT CCCGTGCTGG

1001 ACTCCGACGG CTCCTTCTTC CTCTATAGCA AGCTCACCGT
```

-continued

```
1041 GGACAAGAGC AGGTGGCAGC AGGGGAACGT CTTCTCATGC

1081 TCCGTGATGC ATGAGGCTCT GCACAACCAC TACACGCAGA

1121 AGAGCCTCTC CCTGTCTCCG GGTAAATGA
```

A variant of hALK3(24-152)-Fc with the TPA leader and with murine Fc substituted for human Fc is shown in FIG. 10. A sense nucleotide sequence encoding this variant and its corresponding antisense sequence are indicated in FIG. 11. Applicants constructed a form of hALK3(24-152)-mFc having an asparagine at position 71 (position 70 in the native ALK3 ECD sequence). The protein was expressed in CHO cell lines, and N-terminal sequencing revealed a primary species with an N-terminal block, indicating a start at the native glutamine (Q) residue, consistent with the protein of SEQ ID NO:7, and a single minor sequence of GAQNLDSM-LHGTGMK (SEQ ID NO: 17). Applicants additionally constructed a hALK3(24-152)-hFc protein having the native ALK3 sequence. Another ALK3-Fc variant comprising the murine ALK3 extracellular domain (native residues 24-152 in the murine precursor) and murine Fc domain was generated by similar methods. The amino acid sequence of this variant, mALK3(24-152)-mFc, is shown below with the ALK3 domain underlined:

```
                                               (SEQ ID NO: 18)
  1 MDAMKRGLCC VLLLCGAVFV SPGAQNLDSM LHGTGMKSDL DQKKPENGVT

51 LAPEDTLPFL KCYCSGHCPD DAINNTCITN GHCFAIIEED DQGETTLTSG

101 CMKYEGSDFQ CKDSPKAQLR RTIECCRTNL CNQYLQPTLP PVVIGPFFDG

151 SIRTGGGEPR VPITQNPCPP LKECPPCAAP DLLGGPSVFI FPPKIKDVLM

201 ISLSPMVTCV VVDVSEDDPD VQISWFVNNV EVHTAQTQTH REDYNSTLRV

251 VSALPIQHQD WMSGKEFKCK VNNRALPSPI EKTISKPRGP VRAPQVYVLP

301 PPAEEMTKKE FSLTCMITGF LPAEIAVDWT SNGRTEQNYK NTATVLDSDG

351 SYFMYSKLRV QKSTWERGSL FACSVVHEGL HNHLTTKTIS RSLGK
```

EXAMPLE 2

Ligand Binding to ALK3-Fc

Biacore™ methodology was used to determine the binding affinity of ALK3-Fc fusion proteins for more than 15 members of the BMP/GDF family. mALK3-mFc derived from HEK 293 cells displayed high-affinity binding to hBMP2 and hBMP4 ($K_D$=2.43×10$^{-9}$ and 9.47×10$^{-10}$, respectively), as well as moderate-affinity binding to several other ligands, including hBMP6 and hBMP7. hALK3(24-152)-hFc displayed a similar binding profile. Specifically, hALK3(24-152)-hFc derived from HEK 293 cells bound to hBMP2 and hBMP4 with $K_D$s of 6.53×10$^{-10}$ and 1.02×10$^{-9}$, respectively, while hALK3(24-152)-hFc derived from CHO cells bound to hBMP2 and hBMP4 with $K_D$s of 4.53×10$^{-10}$ and 7.03×10$^{-10}$, respectively. Like mALK3(24-152)-mFc, hALK3(24-152)-hFc derived from both cell types exhibited moderate affinity binding to hBMP6 and hBMP7, among other ligands.

The overall selectivity of ALK3-Fc for BMP2 and BMP4 is notable. While not wishing to be bound to any particular mechanism, Applicants hypothesize, based on these results, that ALK3-Fc exerts its effects in vivo primarily by binding BMP2 and BMP4 and thereby inhibiting signaling by these ligands. Accordingly, it is predicted that antibodies against BMP2 and/or BMP4 would also stimulate bone formation. Alternatively, an antibody against the ALK3 ligand-binding domain would be expected to inhibit ALK3-mediated signaling more broadly. FIG. 18 shows diagrammatically examples of three approaches proposed here to interfere with signaling by BMP2, BMP4, and potentially additional ligands for the purpose of promoting bone formation.

A series of ALK3-Fc proteins incorporating truncated variants of the human ALK3 extracellular domain (ECD) were generated and compared with hALK3(24-152)-hFc for their ligand binding affinities. ALK3 ECD variants with N-terminal deletions of 6, 12, 27, or 31 amino acids, C-terminal deletions of 6 or 12 amino acids, and a double-truncation were expressed in HEK 293 cells and purified by Mab chromatography (Protein A column). Biacore™ methodology was used to screen members of the BMP/GDF/TGFβ ligand superfamily for binding to these variants.

Binding Affinity ($K_D$, in pM) of Selected Human Ligands for Human ALK3 ECD Variants

| Construct Expressed in 293 Cells | | Ligand | | | |
|---|---|---|---|---|---|
| | | hBMP2 | hBMP4 | hBMP6 | hBMP7 |
| Full Length | hALK3(24-152)-hFc | 653 | 1020 | 17300 | 5990 |
| ALK3NΔ6 | hALK3(30-152)-hFc | 869 | 1610 | 12800 | — |
| ALK3NΔ12 | hALK3(36-152)-hFc | 1040 | — | 5280 | — |
| ALK3NΔ27 | hALK3(51-152)-hFc | 1570 | — | 8040 | 4290 |
| ALK3NΔ31 | hALK3(55-152)-hFc | 663 | — | 17000 | 3670 |
| ALK3CΔ6 | hALK3(24-146)-hFc | 532 | 396 | — | — |
| ALK3CΔ12 | hALK3(24-140)-hFc | 769 | 446 | — | 5900 |
| ALK3NΔ6CΔ6 | hALK3(30-146)-hFc | 437 | 329 | — | — |

— no detectable binding

As shown above, the C-terminal truncations that were evaluated display similar or increased binding affinity for BMP2/BMP4 compared to full-length ALK3 ECD, with generally reduced binding to BMP6/BMP7, although ALK3CΔ12 retains binding to BMP7 at an affinity similar to the full-length ALK3 ECD. In contrast, N-terminal truncations tend to reduce binding to BMP2, abolish binding to BMP4, and display varying effects on binding to BMP6/BMP7. Interestingly, the double-truncated variant ALK3NΔ6CΔ6 displays increased affinity for BMP2/BMP4 compared to full-length ALK3 ECD, in combination with undetectable binding to BMP6/BMP7. Molecules with greater selectivity for the desired targets, BMP2 and BMP4 are useful because they will have fewer "off target" effects in patients. N-terminal sequencing demonstrated that the nucleic acid encoding a six amino acid truncation at the N-terminus, when expressed in cell culture, gave rise to a population of polypeptides having the six amino acid truncation and a population of polypeptides having a seven amino acid truncation. Taken together, these demonstrate that hALK3-hFc polypeptides containing up to a seven amino acid truncation at the N-terminus and up to a twelve amino acid truncation at the C-terminus retain useful activity and demonstrate the desirable and surprising reduction in binding to off-target ligands. Thus, an ALK3 polypeptide comprising at least amino acids 8 to 117 of SEQ ID NO:3 may be used for the purposes described herein.

Ligand binding properties were used to compare the quality of hALK3(24-152)-hFc protein derived from CHO cells with that derived from HEK 293 cells. As determined by Biacore™ methodology, the affinity (Kd) of BMP2 for hALK3(24-152)-hFc did not differ depending on the source of fusion protein; however, the percentage of active protein generated by CHO cells was higher than that of HEK 293 cells based on their respective Rmax values. Rmax is a measure of protein quality equal to $(MW_A/MW_L) \times R_L \times S_M$, where $MW_A$ is the molecular weight of analyte, $MW_L$ is the molecular weight of ligand, $R_L$ in the immobilization level in response units, and $S_M$ is the molar stoichiometry. Corresponding analysis of BMP4 binding revealed that protein derived from CHO cells exhibited higher affinity for BMP4 than did that from HEK 293 cells ($K_D$s of 314 pM vs. 1020 pM, respectively), and the Rmax value for protein generated by CHO cells was three times that for protein from HEK 293 cells, again indicating a higher percentage of active protein. Therefore, unexpected benefits of CHO cells as the source of hALK3(24-152)-hFc protein include higher binding affinity of protein to BMP4 and greater bioavailability predicted to result from higher protein quality (Rmax value).

EXAMPLE 3 hALK3-mFc Improves Bone Status in Mice

Figure 13:
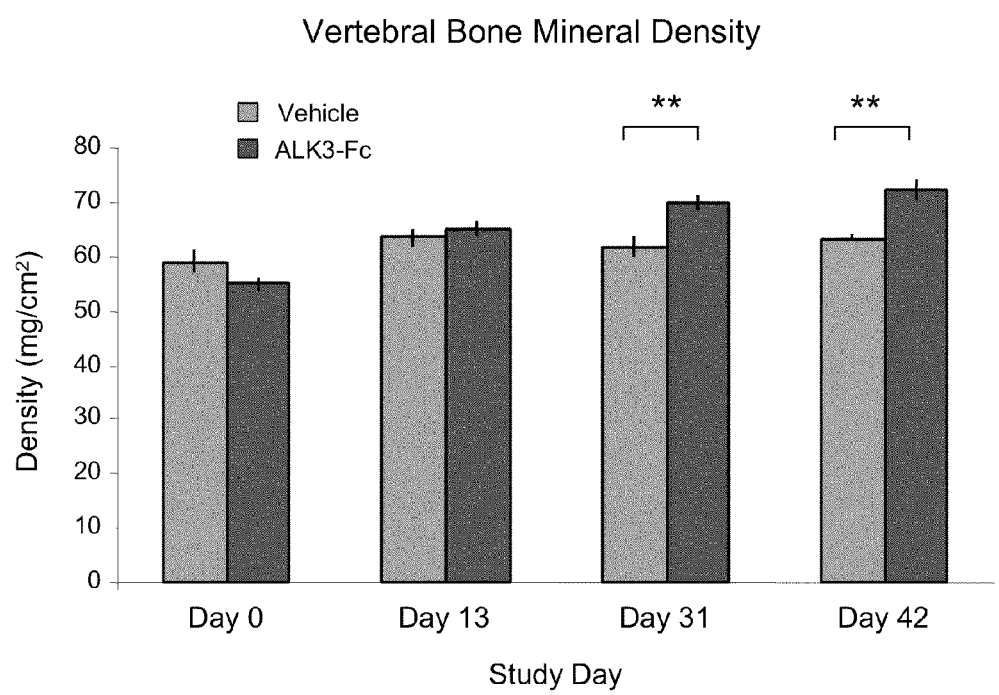
FIG. 13 shows the effect of hALK3(24-152)-mFc treatment on vertebral bone mineral density in female mice. Measurements of a region containing the fourth and fifth lumbar vertebrae (L4, L5) were made by DEXA. Data are means (n=8 per group)±SEM. **, $P<0.005$ vs. vehicle by unpaired t-test. hALK3(24-152)-mFc increased vertebral bone density significantly after 31 and 42 days of treatment.
Figure 14:
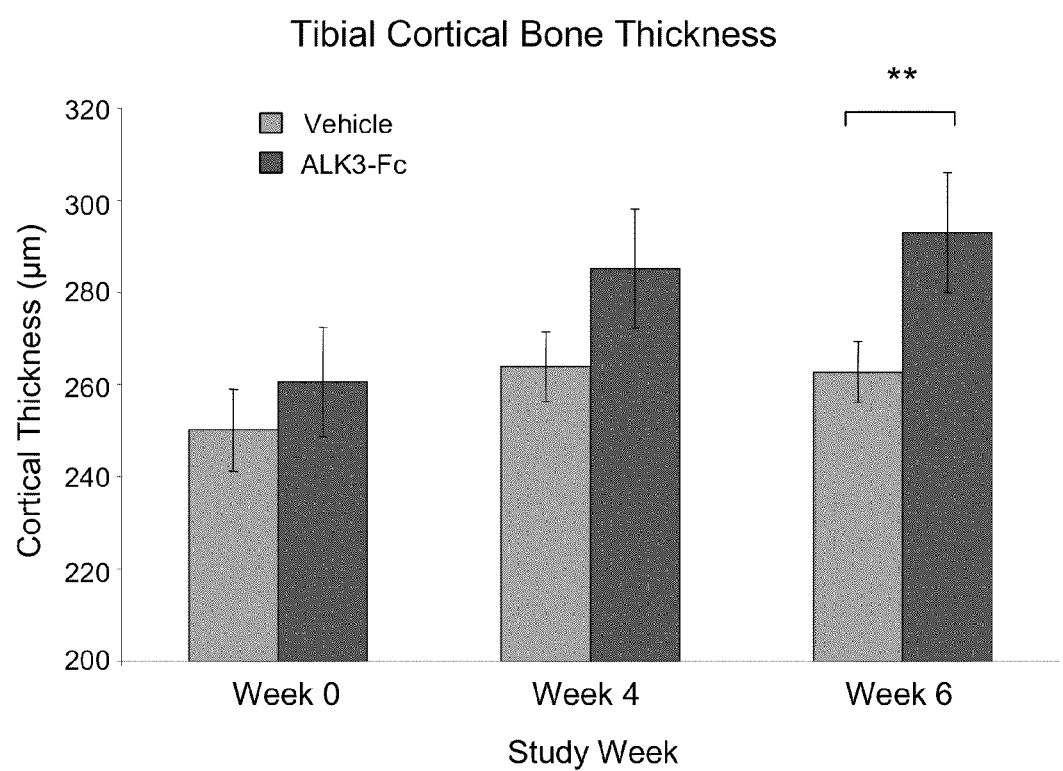
FIG. 14 shows the effect of hALK3(24-152)-mFc treatment on cortical bone thickness in female mice. Measurements of the right proximal tibia were made by micro-computed tomography (micro-CT). Data are means (n=8 per group), and error bars represent±two times SEM. **, $P<0.005$ vs. vehicle by unpaired t-test. hALK3(24-152)-mFc increased the thickness of cortical bone significantly after 6 weeks of treatment.
Figure 15:
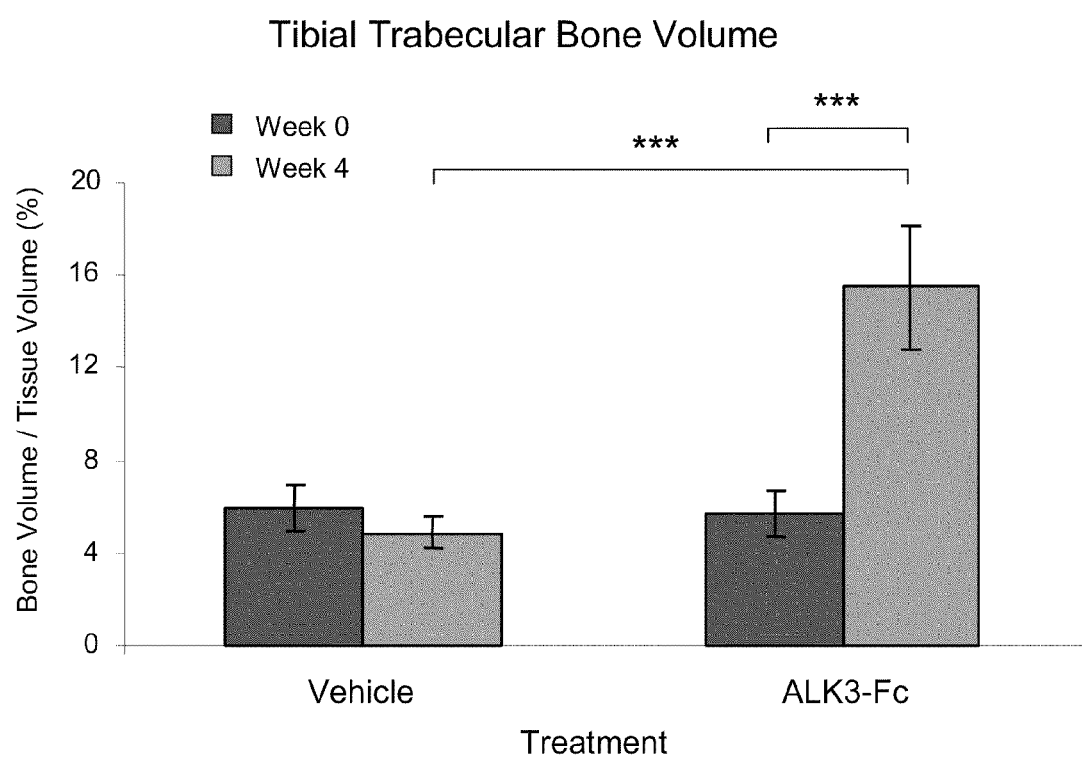
FIG. 15 shows the effect of hALK3(24-152)-mFc treatment on trabecular bone volume in female mouse. Measurements of the right proximal tibia were made by micro-CT. Data are means (n=8 per group), and error bars represent±two times SEM. ***, P<0.001 vs. pretreatment baseline or vehicle by unpaired t-test. hALK3(24-152)-mFc more than doubled the proportion of trabecular bone after 4 weeks of treatment.
Figure 16:
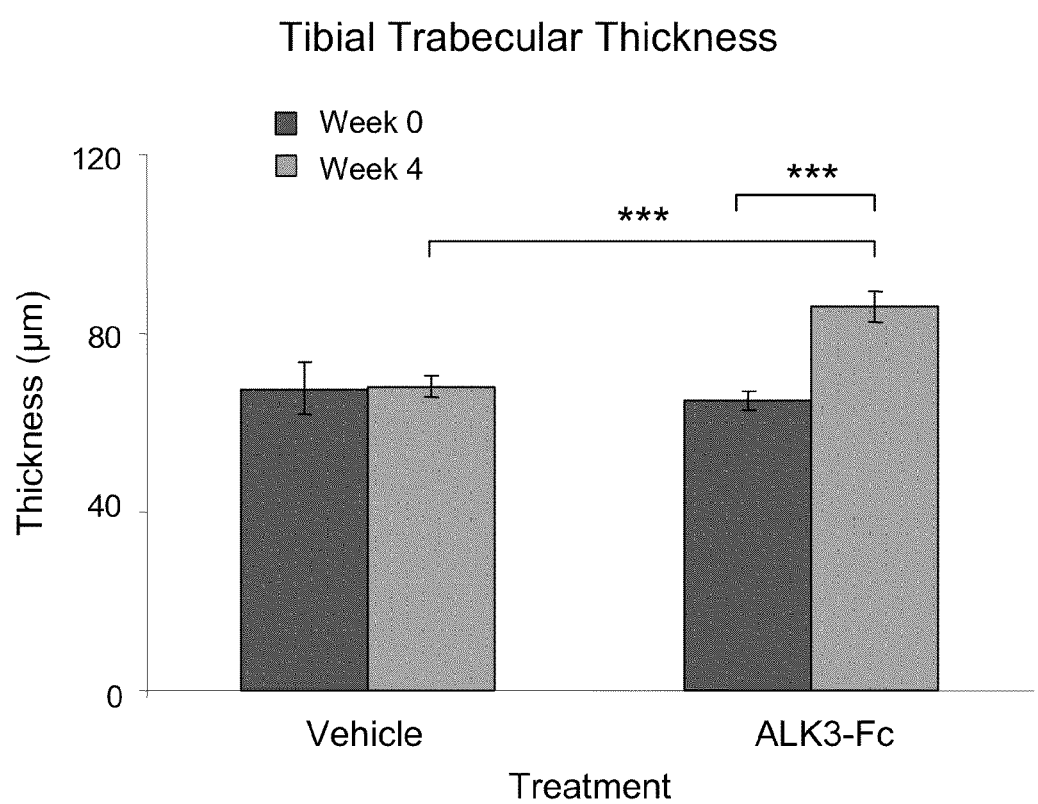
FIG. 16 shows the effect of hALK3(24-152)-mFc treatment on mean trabecular thickness in female mice. Measurements of the right proximal tibia were made by micro-CT. Data are group means (n=8 per group), and error bars represent±two times SEM. ***, P<0.001 vs. pretreatment baseline or vehicle by unpaired t-test. hALK3(24-152)-mFc significantly increased trabecular thickness after 4 weeks of treatment.

Applicants investigated the ability of a version of ALK3-mFc to improve bone status in mice. Twelve-week-old female C57BL/6 mice (n=8 per group) were treated with hALK3(24-152)-mFc, 10 mg/kg, or vehicle (Tris-buffered saline) by intraperitoneal injection twice per week for a total of six weeks. Compared to vehicle, hALK3(24-152)-mFc significantly increased whole-body bone density, as determined by dual energy x-ray absorptiometry (DEXA), by Day 31 and maintained this effect through study completion on Day 42 (FIG. 12). A similar effect of hALK3(24-152)-mFc treatment on bone density was observed for localized analysis of lumbar vertebrae by DEXA at these same time points (FIG. 13). In addition, high-resolution measurements of the tibial shaft and proximal tibia were conducted by micro-computed tomography (micro-CT) to determine the effect of hALK3(24-152)-mFc on cortical bone and trabecular bone, respectively. As compared to vehicle, hALK3(24-152)-mFc treatment significantly increased: i) thickness of cortical bone by Week 6 (FIG. 14), ii) volume of trabecular bone by Week 4 (FIG. 15), and iii) mean trabecular thickness by Week 4 (FIG. 16). Representative three-dimensional reconstructions of micro-CT-generated sections through the proximal tibia (FIG. 17) underscore the robust stimulatory effect of hALK(24-152)-mFc treatment (4 weeks) on trabecular bone microarchitecture Importantly, hALK3(24-152)-mFc treatment did not cause significant changes in lean tissue mass, fat mass, or red blood cell mass over the course of the study.

Taken together, the foregoing data demonstrate that hALK3(24-152)-mFc can be used in vivo to selectively improve bone status through increased bone mineral density and increased net formation of both cortical and trabecular bone.

EXAMPLE 4 hALK3-mFc Increases Bone Strength in Mice

In the experiment described in Example 3, Applicants also investigated the ability of hALK3(24-152)-mFc to increase bone strength. After 6 weeks of dosing, femurs were collected and stored frozen at −20° C. Bones were later thawed to ambient temperature, and destructive four-point bend tests were performed on the left femur midshaft with an Instron mechanical testing instrument (Instron 4465 retrofitted to 5500). Separation between the fixed supports was 7 mm, and separation between the two points of load application was 2.5 mm Load was applied at a constant displacement rate of 3 mm/min until bone breakage, and maximum load, stiffness, and energy absorption data were calculated with Bluehill v 2.5 software. Compared to vehicle, hALK3(24-152)-mFc significantly increased maximum bone load by 30% (FIG. 19), bone stiffness by 14% (FIG. 20), and energy to bone failure by 32% (FIG. 21). These findings demonstrate that increased bone strength accompanies the improvement in bone composition observed with hALK3(24-152)-mFc treatment (Example 3).

EXAMPLE 5

Effects of mALK3-mFc on Bone in an OVX Mouse Model of Osteopenia

Estrogen deficiency in postmenopausal women promotes bone loss, particularly loss of trabecular bone. Therefore, Applicants investigated the ability of mALK3(24-152)-mFc to improve bone status in an ovariectomized (OVX) mouse model of osteopenia with established bone loss. Eight-week-old female C57BL/6 mice underwent bilateral OVX or sham surgery, then remained untreated for an eight-week interval. At the end of eight weeks, baseline measurements by micro-CT and DEXA confirmed significant bone loss in the OVX mice compared to sham treatment. Most notable was a 43% reduction in trabecular bone volume (FIG. 22, Day 0 time point), as determined in the proximal tibia by micro-CT. Mice were then treated with mALK3(24-152)-mFc, 10 mg/kg, or vehicle (Tris-buffered saline), by ip injection twice per week for 8 weeks.

Treatment with mALK3(24-152)-mFc led to improvement in both trabecular and cortical bone despite continuing estrogen deficiency. By study completion on Day 56, trabecular bone volume in the proximal tibia of OVX mice treated with mALK3(24-152)-mFc was increased by nearly 250% compared to OVX controls and by more than 80% compared to sham controls (FIG. 22). mALK3(24-152)-mFc treatment also caused growth of cortical bone, as indicated by increased cortical thickness (FIG. 23) and reduced endosteal circumference (FIG. 24) in the tibial shaft compared to OVX controls. These improvements were accompanied by increased bone mineral density. Compared to OVX controls, mALK3(24-152)-mFc treatment significantly increased whole-body bone mineral density (as determined by DEXA) by Day 14 and maintained this improvement through study completion (FIG. 25). Similar effects of mALK3(24-152)-mFc treatment were observed on mineral density in the lumbar spine (FIG. 26) and femur-tibia (FIG. 27). Three-dimensional images of vertebral trabecular bone derived from micro-CT analysis (FIG. 28) underscore the robust improvement in bone status associated with mALK3(24-152)-mFc treatment despite ongoing estrogen deficiency. These findings demonstrate that mALK3(24-152)-mFc can reverse the deterioration of bone, including trabecular bone, associated with estrogen withdrawal in a mouse model of osteopenia. The ability of mALK3(24-152)-mFc to transform bone from an osteopenic condition to one which surpasses the quantity (FIGS. 22-24, 28) and matches the quality (FIGS. 25-27) of bone in gonad-intact controls is evidence that this agent exerts effects which are not only antiresorptive but anabolic.

EXAMPLE 6

Effects of mALK3-mFc on Bone Histomorphometry and Serum Biomarkers in Mice

In a separate study, Applicants investigated the ability of mALK3-mFc to improve bone status in mice as assessed by histomorphometry and serum biomarkers. Twelve-week-old female C57BL/6 mice were treated with mALK3(24-152)-mFc, 10 mg/kg, or vehicle (Tris-buffered saline) by intraperitoneal injection twice per week. Cohorts of mice were necropsied after 14, 28, and 42 days of treatment to permit collection of bone and serum. The fluorescent compounds calcein (20 mg/kg) and demeclocycline (20 mg/kg) were administered intraperitoneally to mice 9 days and 2 days before necropsy, respectively, for dynamic histomorphometric analysis.

Bone was prepared for histomorphometry as follows. At necropsy, the right femur was detached, and the distal quarter of the femur underwent histological preparation consisting of dehydration, infiltration by methylmethacrylate, and embedding in methylmethacrylate. A rotary microtome was used to obtain sets of frontal sections at thicknesses of 4 and 8 µm. The thinner sections were stained with Goldner's trichrome and used for analysis of static parameters, whereas the thicker sections were mounted unstained and used for analysis of dynamic parameters. Histomorphometry was performed in a treatment-blind manner with a Nikon Eclipse E4000 light/epifluorescent microscope connected to a video subsystem running OsteoMeasure image analysis software.

Histomorphometric analysis of the distal femur revealed both anabolic and antiresorptive effects of ALK3-Fc. Compared to vehicle, mALK3(24-152)-mFc significantly increased bone volume at all three time points by up to 90% (FIG. 29) Importantly, mALK3(24-152)-mFc increased bone formation rate by as much as 120% (FIG. 30) and bone mineralizing surface by as much as 115% (FIG. 31). These latter parameters are considered to be indicative of anabolic bone growth, although additional markers of anabolic effects—osteoblast surface and osteoid surface—showed more modest or negligible increases. Histomorphometric analysis also provided evidence of temporal antiresorptive effects, as mALK3(24-152)-mFc reduced osteoclast surface significantly at Day 28 only (FIG. 32), and a similar effect on eroded surface was observed.

Effects of mALK3(24-152)-mFc treatment on serum biomarkers of bone status were also investigated. RANKL (receptor activator of nuclear factor-κB ligand) is produced by osteoblasts and is a key activator of osteoclast differentiation, whereas osteoprotegerin (OPG) is an endogenous inhibitor of RANKL signaling. Thus, the RANKL/OPG ratio is an important determinant of osteoclastic activity, bone mass, and bone quality (Boyce et al., 2008, Arch Biochem Biophys 473:139-146). In the present experiment, serum levels of RANKL and OPG were measured with Millipore products (MBN2A-41K and MBN-41K-1OPG) incorporating Luminex xMAP® technology. mALK3(24-152)-mFc treatment significantly reduced serum RANKL levels at all three time points (FIG. 33) and significantly increased serum OPG levels at 28 and 42 days (FIG. 34) compared to vehicle. These results indicate that mALK3(24-152)-mFc treatment stimulates bone formation in part through an antiresorptive action.

Example 7

Effects of mALK3-mFc on Sclerostin Gene Expression in Mice

Sclerostin protein is a key negative regulator of bone formation, and interference with sclerostin signaling has been reported to exert anabolic effects on bone in vivo (Li et al., 2009, J Bone Miner Res 24:578-588). Applicants therefore investigated whether mALK3(24-152)-mFc treatment in vivo alters sclerostin gene expression in bone and thus whether a reduction in sclerostin levels could potentially mediate some of the bone-rebuilding effects of ALK3-Fc. Twelve-week-old female C57BL/6 mice were treated with mALK3(24-152)-mFc or vehicle (PBS) by intraperitoneal injection twice per week. Cohorts of mice were necropsied after 2, 7, 14, and 28 days of treatment to permit bilateral collection of femurs and tibias, which were separated and cleaned of any residual muscle or connective tissue.

Sclerostin gene expression was analyzed as follows. Bones were trimmed to expose the interior marrow shaft, and marrow cells were flushed out with sterile saline using a 21-gauge needle attached to a 3-mL syringe. The femurs and tibias from each mouse were pulverized together, and RNA was extracted from the resulting powder with a Ribopure kit (Ambion) according to the manufacturer's instructions. RNA integrity in bone samples was confirmed with RNA Nano Chips (Agilent Technologies) run on an Agilent Technologies 2100 Bioanalyzer according to the manufacturer's instructions. RNA was reverse-transcribed using TaqMan RT reagents (Applied Biosystems), and real-time polymerase chain reaction (PCR) was performed with sclerostin probe/primers and Eukaryotic 18S rRNA Endogenous Control (both from Applied Biosystems). Amplifications were performed with an Applied Biosystems 7300 System, and results were analyzed using the $2^{-\Delta\Delta Ct}$ method.

Compared to vehicle, treatment with mALK3(24-152)-mFc reduced bone levels of sclerostin mRNA significantly at three of the four time points investigated (FIG. 35). This finding indicates that reduced expression of sclerostin may contribute to the anabolic and/or antiresorptive effects of mALK3(24-152)-mFc on bone.

EXAMPLE 8

Effect of hALK3-hFc on Bone Status in Mice

Applicants investigated effects of the human construct hALK3(24-152)-hFc on bone status in mice. Twelve-weekold female C57BL/6 mice (n=6 per group) were treated with hALK3(24-152)-hFc, 10 mg/kg, or vehicle (Tris-buffered saline) by intraperitoneal injection twice per week for a total of 6 weeks. Over the course of the experiment, trabecular bone volume decreased nearly 20% in vehicle-treated controls but increased more than 80% with hALK3(24-152)-hFc treatment, as determined by micro-CT analysis of the proximal tibia (FIG. 36). Significant increases from baseline in trabecular number (34%) and trabecular thickness (20%) were also observed with hALK3(24-152)-hFc, but not vehicle, by study conclusion. Compared to vehicle, hALK3 (24-152)-hFc significantly increased whole-body bone mineral density, as determined by DEXA, at study conclusion. Localized analysis of lumbar vertebrae (L1-L6) by DEXA also revealed a significant stimulatory effect (21% increase) of hALK3(24-152)-hFc on bone mineral density at study conclusion compared to vehicle.

These results demonstrate that the human construct hALK3(24-152)-hFc can improve bone status in mice, although it is expected that the magnitude of its effects in rodents would be blunted by an immune response. Collectively, the foregoing findings demonstrate that ALK3-Fc constructs 1) promote bone formation in both the axial skeleton and appendicular skeleton through both antiresorptive and anabolic actions, 2) improve bone mechanical strength, and 3) reverse bone loss induced by estrogen deficiency in a mouse model of established osteopenia.

EXAMPLE 9

Exemplary hALK3-hFc Nucleic Acids and Proteins

This example summarizes nucleic acid constructs used to express ALK3 constructs in CHO cells, according to the methods provided herein, and provides the mature proteins isolated from cell culture.

A. The Nucleic Acid of SEQ ID NO:19 was Expressed in CHO Cells and the Following ALK3-Fc Species were Isolated:

(1) The hALK3(24-152)-hFc sequence shown in SEQ ID NO:7, beginning with a glutamine (which tends to be blocked for N-terminal sequencing by Edman degradation).

(2) The hALK3(GA,24-152)-hFc sequence shown below (SEQ ID NO: 20), which retains an initial glycine-alanine from the leader sequence.

```
                                            (SEQ ID NO: 20)
                            GAQNLDSM LHGTGMKSDS

DQKKSENGVT  LAPEDTLPFL  KCYCSGHCPD  DAINNTCITN

GHCFAIIEED  DQGETTLASG  CMKYEGSDFQ  CKDSPKAQLR

RTIECCRTNL  CNQYLQPTLP  PVVIGPFFDG  SIRTGGGTHT

CPPCPAPELL  GGPSVFLFPP  KPKDTLMISR  TPEVTCVVVD

VSHEDPEVKF  NWYVDGVEVH  NAKTKPREEQ  YNSTYRVVSV

LTVLHQDWLN  GKEYKCKVSN  KALPAPIEKT  ISKAKGQPRE

PQVYTLPPSR  EEMTKNQVSL  TCLVKGFYPS  DIAVEWESNG

QPENNYKTTP  PVLDSDGSFF  LYSKLTVDKS  RWQQGNVFSC

SVMHEALHNH  YTQKSLSLSP  GK*
```

B. A Nucleic Acid Encoding hALK3(24-146)-hFc, Shown Below (SEQ ID NO: 21) was Expressed in CHO Cells:

```
                                            (SEQ ID NO: 21)
                             AT GGATGCAATG AAGAGAGGGC

TCTGCTGTGT  GCTGCTGCTG  TGTGGAGCAG  TCTTCGTTTC

GCCCGGCGCC  CAGAATCTGG  ATAGTATGCT  TCATGGCACT

GGGATGAAAT  CAGACTCCGA  CCAGAAAAAG  TCAGAAAATG

GAGTAACCTT  AGCACCAGAG  GATACCTTGC  CTTTTTTAAA

GTGCTATTGC  TCAGGGCACT  GTCCAGATGA  TGCTATTAAT

AACACATGCA  TAACTAATGG  ACATTGCTTT  GCCATCATAG

AAGAAGATGA  CCAGGGAGAA  ACCACATTAG  CTTCAGGGTG

TATGAAATAT  GAAGGATCTG  ATTTTCAGTG  CAAAGATTCT

CCAAAAGCCC  AGCTACGCCG  GACAATAGAA  TGTTGTCGGA

CCAATTTATG  TAACCAGTAT  TTGCAACCCA  CACTGCCCCC

TGTTGTCATA  GGTCCGTTTA  CCGGTGGTGG  AACTCACACA

TGCCCACCGT  GCCCAGCACC  TGAACTCCTG  GGGGGACCGT

CAGTCTTCCT  CTTCCCCCCA  AAACCCAAGG  ACACCCTCAT

GATCTCCCGG  ACCCCTGAGG  TCACATGCGT  GGTGGTGGAC

GTGAGCCACG  AAGACCCTGA  GGTCAAGTTC  AACTGGTACG

TGGACGGCGT  GGAGGTGCAT  AATGCCAAGA  CAAAGCCGCG

GGAGGAGCAG  TACAACAGCA  CGTACCGTGT  GGTCAGCGTC

CTCACCGTCC  TGCACCAGGA  CTGGCTGAAT  GGCAAGGAGT

ACAAGTGCAA  GGTCTCCAAC  AAAGCCCTCC  CAGCCCCCAT

CGAGAAAACC  ATCTCCAAAG  CCAAAGGGCA  GCCCCGAGAA

CCACAGGTGT  ACACCCTGCC  CCCATCCCGG  GAGGAGATGA

CCAAGAACCA  GGTCAGCCTG  ACCTGCCTGG  TCAAAGGCTT

CTATCCCAGC  GACATCGCCG  TGGAGTGGGA  GAGCAATGGG

CAGCCGGAGA  ACAACTACAA  GACCACGCCT  CCCGTGCTGG

ACTCCGACGG  CTCCTTCTTC  CTCTATAGCA  AGCTCACCGT

GGACAAGAGC  AGGTGGCAGC  AGGGGAACGT  CTTCTCATGC

TCCGTGATGC  ATGAGGCTCT  GCACAACCAC  TACACGCAGA

AGAGCCTCTC  CCTGTCTCCG  GGTAAATGA
```

The following protein species were isolated:

(1) The hALK3(24-146)-hFc shown below (SEQ ID NO:22), beginning with a glutamine (which tends to be blocked for N-terminal sequencing by Edman degradation).

```
                                            (SEQ ID NO: 22)
                                      QNLDSMLHGT

GMKSDSDQKK  SENGVTLAPE  DTLPFLKCYC  SGHCPDDAIN

NTCITNGHCF  AIIEEDDQGE  TTLASGCMKY  EGSDFQCKDS

PKAQLRRTIE  CCRTNLCNQY  LQPTLPPVVI  GPFTGGGTHT

CPPCPAPELL  GGPSVFLFPP  KPKDTLMISR  TPEVTCVVVD

VSHEDPEVKF  NWYVDGVEVH  NAKTKPREEQ  YNSTYRVVSV

LTVLHQDWLN  GKEYKCKVSN  KALPAPIEKT  ISKAKGQPRE
```

```
PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*
```

(2) The hALK3(GA,24-146)-hFc sequence shown below (SEQ ID NO: 23), which retains an initial glycine-alanine from the leader sequence.

```
                                        (SEQ ID NO: 23)
                                     GA QNLDSMLHGT

GMKSDSDQKK SENGVTLAPE DTLPFLKCYC SGHCPDDAIN

NTCITNGHCF AIIEEDDQGE TTLASGCMKY EGSDFQCKDS

PKAQLRRTIE CCRTNLCNQY LQPTLPPVVI GPFTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*
```

C. A Nucleic Acid Encoding hALK3(24-140)-hFc, Shown Below (SEQ ID NO: 24) was Expressed in CHO Cells:

```
                                         (SEQ ID NO: 24)
                                                    ATGG

ATGCAATGAA GAGAGGGCTC TGCTGTGTGC TGCTGCTGTG

TGGAGCAGTC TTCGTTTCGC CCGGCGCCCA GAATCTGGAT

AGTATGCTTC ATGGCACTGG GATGAAATCA GACTCCGACC

AGAAAAAGTC AGAAAATGGA GTAACCTTAG CACCAGAGGA

TACCTTGCCT TTTTTAAAGT GCTATTGCTC AGGGCACTGT

CCAGATGATG CTATTAATAA CACATGCATA ACTAATGGAC

ATTGCTTTGC CATCATAGAA GAAGATGACC AGGGAGAAAC

CACATTAGCT TCAGGGTGTA TGAAATATGA AGGATCTGAT

TTTCAGTGCA AAGATTCTCC AAAAGCCCAG CTACGCCGGA

CAATAGAATG TTGTCGGACC AATTTATGTA ACCAGTATTT

GCAACCCACA CTGCCCCCTA CCGGTGGTGG AACTCACACA

TGCCCACCGT GCCCAGCACC TGAACTCCTG GGGGGACCGT

CAGTCTTCCT CTTCCCCCCA AAACCCAAGG ACACCCTCAT

GATCTCCCGG ACCCCTGAGG TCACATGCGT GGTGGTGGAC

GTGAGCCACG AAGACCCTGA GGTCAAGTTC AACTGGTACG

TGGACGGCGT GGAGGTGCAT AATGCCAAGA CAAAGCCGCG

GGAGGAGCAG TACAACAGCA CGTACCGTGT GGTCAGCGTC

CTCACCGTCC TGCACCAGGA CTGGCTGAAT GGCAAGGAGT

ACAAGTGCAA GGTCTCCAAC AAAGCCCTCC CAGCCCCCAT

CGAGAAAACC ATCTCCAAAG CCAAAGGGCA GCCCCGAGAA

CCACAGGTGT ACACCCTGCC CCCATCCCGG GAGGAGATGA

CCAAGAACCA GGTCAGCCTG ACCTGCCTGG TCAAAGGCTT

CTATCCCAGC GACATCGCCG TGGAGTGGGA GAGCAATGGG

CAGCCGGAGA ACAACTACAA GACCACGCCT CCCGTGCTGG

ACTCCGACGG CTCCTTCTTC CTCTATAGCA AGCTCACCGT

GGACAAGAGC AGGTGGCAGC AGGGGAACGT CTTCTCATGC

TCCGTGATGC ATGAGGCTCT GCACAACCAC TACACGCAGA

AGAGCCTCTC CCTGTCTCCG GGTAAATGA
```

The following protein species were isolated:

(1) The hALK3(24-140)-hFc shown below (SEQ ID NO:25), beginning with a glutamine (which tends to be blocked for N-terminal sequencing by Edman degradation.

```
                                         (SEQ ID NO: 25)
                                                    QNLD

SMLHGTGMKS DSDQKKSENG VTLAPEDTLP FLKCYCSGHC

PDDAINNTCI TNGHCFAIIE EDDQGETTLA SGCMKYEGSD

FQCKDSPKAQ LRRTIECCRT NLCNQYLQPT LPPTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*
```

(2) The hALK3(GA,24-140)-hFc sequence shown below (SEQ ID NO: 26), which retains an initial glycine-alanine from the leader sequence.

```
                                         (SEQ ID NO: 26)
                                                  GAQNLD

SMLHGTGMKS DSDQKKSENG VTLAPEDTLP FLKCYCSGHC

PDDAINNTCI TNGHCFAIIE EDDQGETTLA SGCMKYEGSD

FQCKDSPKAQ LRRTIECCRT NLCNQYLQPT LPPTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*
```

D. A Nucleic Acid Encoding hALK3(30-152)-hFc, Shown Below (SEQ ID NO: 27) was Expressed in CHO Cells:

```
                                         (SEQ ID NO: 27)
                                     AT GGATGCAATG AAGAGAGGGC

TCTGCTGTGT GCTGCTGCTG TGTGGAGCAG TCTTCGTTTC
```

```
GCCCGGCGCC CTTCATGGCA CTGGGATGAA ATCAGACTCC

GACCAGAAAA AGTCAGAAAA TGGAGTAACC TTAGCACCAG

AGGATACCTT GCCTTTTTTA AAGTGCTATT GCTCAGGGCA

CTGTCCAGAT GATGCTATTA ATAACACATG CATAACTAAT

GGACATTGCT TTGCCATCAT AGAAGAAGAT GACCAGGGAG

AAACCACATT AGCTTCAGGG TGTATGAAAT ATGAAGGATC

TGATTTTCAG TGCAAAGATT CTCCAAAAGC CCAGCTACGC

CGGACAATAG AATGTTGTCG GACCAATTTA TGTAACCAGT

ATTTGCAACC CACACTGCCC CCTGTTGTCA TAGGTCCGTT

TTTTGATGGC AGCATTCGAA CCGGTGGTGG AACTCACACA

TGCCCACCGT GCCCAGCACC TGAACTCCTG GGGGGACCGT

CAGTCTTCCT CTTCCCCCCA AAACCCAAGG ACACCCTCAT

GATCTCCCGG ACCCCTGAGG TCACATGCGT GGTGGTGGAC

GTGAGCCACG AAGACCCTGA GGTCAAGTTC AACTGGTACG

TGGACGGCGT GGAGGTGCAT AATGCCAAGA CAAAGCCGCG

GGAGGAGCAG TACAACAGCA CGTACCGTGT GGTCAGCGTC

CTCACCGTCC TGCACCAGGA CTGGCTGAAT GGCAAGGAGT

ACAAGTGCAA GGTCTCCAAC AAAGCCCTCC CAGCCCCCAT

CGAGAAAACC ATCTCCAAAG CCAAAGGGCA GCCCCGAGAA

CCACAGGTGT ACACCCTGCC CCCATCCCGG GAGGAGATGA

CCAAGAACCA GGTCAGCCTG ACCTGCCTGG TCAAAGGCTT

CTATCCCAGC GACATCGCCG TGGAGTGGGA GAGCAATGGG

CAGCCGGAGA ACAACTACAA GACCACGCCT CCCGTGCTGG

ACTCCGACGG CTCCTTCTTC CTCTATAGCA AGCTCACCGT

GGACAAGAGC AGGTGGCAGC AGGGGAACGT CTTCTCATGC

TCCGTGATGC ATGAGGCTCT GCACAACCAC TACACGCAGA

AGAGCCTCTC CCTGTCTCCG GGTAAATGA
```

The following protein species were isolated:

(1) The hALK3(GA,30-152)-hFc shown below (SEQ ID NO:28), which retains an initial glycine-alanine from the leader sequence.

```
                                    (SEQ ID NO: 28)
                                 GA LHGTGMKSDS
DQKKSENGVT LAPEDTLPFL KCYCSGHCPD DAINNTCITN
GHCFAIIEED DQGETTLASG CMKYEGSDFQ CKDSPKAQLR
RTIECCRTNL CNQYLQPTLP PVVIGPFFDG SIRTGGGTHT
CPPCPAPELL GGPSVFLFPP KPKDTLMISR TPEVTCVVVD
VSHEDPEVKF NWYVDGVEVH NAKTKPREEQ YNSTYRVVSV
LTVLHQDWLN GKEYKCKVSN KALPAPIEKT ISKAKGQPRE
PQVYTLPPSR EEMTKNQVSL TCLVKGFYPS DIAVEWESNG
QPENNYKTTP PVLDSDGSFF LYSKLTVDKS RWQQGNVFSC
SVMHEALHNH YTQKSLSLSP GK*
```

(2) The hALK3(A,30-152)-hFc shown below (SEQ ID NO:29), which retains an initial alanine from the leader sequence.

```
                                    (SEQ ID NO: 29)
                                  A LHGTGMKSDS
DQKKSENGVT LAPEDTLPFL KCYCSGHCPD DAINNTCITN
GHCFAIIEED DQGETTLASG CMKYEGSDFQ CKDSPKAQLR
RTIECCRTNL CNQYLQPTLP PVVIGPFFDG SIRTGGGTHT
CPPCPAPELL GGPSVFLFPP KPKDTLMISR TPEVTCVVVD
VSHEDPEVKF NWYVDGVEVH NAKTKPREEQ YNSTYRVVSV
LTVLHQDWLN GKEYKCKVSN KALPAPIEKT ISKAKGQPRE
PQVYTLPPSR EEMTKNQVSL TCLVKGFYPS DIAVEWESNG
QPENNYKTTP PVLDSDGSFF LYSKLTVDKS RWQQGNVFSC
SVMHEALHNH YTQKSLSLSP GK*
```

(3) The hALK3(31-152)-hFc sequence shown below (SEQ ID NO: 30), in which the leader and the initial leucine are removed, leaving an initial histidine (effectively NΔ7).

```
                                    (SEQ ID NO: 30)
                                    HGTGMKSDS
DQKKSENGVT LAPEDTLPFL KCYCSGHCPD DAINNTCITN
GHCFAIIEED DQGETTLASG CMKYEGSDFQ CKDSPKAQLR
RTIECCRTNL CNQYLQPTLP PVVIGPFFDG SIRTGGGTHT
CPPCPAPELL GGPSVFLFPP KPKDTLMISR TPEVTCVVVD
VSHEDPEVKF NWYVDGVEVH NAKTKPREEQ YNSTYRVVSV
LTVLHQDWLN GKEYKCKVSN KALPAPIEKT ISKAKGQPRE
PQVYTLPPSR EEMTKNQVSL TCLVKGFYPS DIAVEWESNG
QPENNYKTTP PVLDSDGSFF LYSKLTVDKS RWQQGNVFSC
SVMHEALHNH YTQKSLSLSP GK*
```

(4) An additional species, hALK3(30-152)-hFc, shown below (SEQ ID NO:31) was expected but not identified by N-terminal sequencing.

```
                                    (SEQ ID NO: 31)
                                    LHGTGMKSDS
DQKKSENGVT LAPEDTLPFL KCYCSGHCPD DAINNTCITN
GHCFAIIEED DQGETTLASG CMKYEGSDFQ CKDSPKAQLR
RTIECCRTNL CNQYLQPTLP PVVIGPFFDG SIRTGGGTHT
CPPCPAPELL GGPSVFLFPP KPKDTLMISR TPEVTCVVVD
VSHEDPEVKF NWYVDGVEVH NAKTKPREEQ YNSTYRVVSV
LTVLHQDWLN GKEYKCKVSN KALPAPIEKT ISKAKGQPRE
PQVYTLPPSR EEMTKNQVSL TCLVKGFYPS DIAVEWESNG
```

QPENNYKTTP PVLDSDGSFF LYSKLTVDKS RWQQGNVFSC

SVMHEALHNH YTQKSLSLSP GK*

E. A Nucleic Acid Encoding hALK3(30-146)-hFc, Shown Below (SEQ ID NO: 32) was Expressed in CHO Cells:

(SEQ ID NO: 32)

ATGG

ATGCAATGAA GAGAGGGCTC TGCTGTGTGC TGCTGCTGTG

TGGAGCAGTC TTCGTTTCGC CCGGCGCCCT TCATGGCACT

GGGATGAAAT CAGACTCCGA CCAGAAAAAG TCAGAAAATG

GAGTAACCTT AGCACCAGAG GATACCTTGC CTTTTTTAAA

GTGCTATTGC TCAGGGCACT GTCCAGATGA TGCTATTAAT

AACACATGCA TAACTAATGG ACATTGCTTT GCCATCATAG

AAGAAGATGA CCAGGGAGAA ACCACATTAG CTTCAGGGTG

TATGAAATAT GAAGGATCTG ATTTTCAGTG CAAAGATTCT

CCAAAAGCCC AGCTACGCCG GACAATAGAA TGTTGTCGGA

CCAATTTATG TAACCAGTAT TTGCAACCCA CACTGCCCCC

TGTTGTCATA GGTCCGTTTA CCGGTGGTGG AACTCACACA

TGCCCACCGT GCCCAGCACC TGAACTCCTG GGGGGACCGT

CAGTCTTCCT CTTCCCCCCA AAACCCAAGG ACACCCTCAT

GATCTCCCGG ACCCCTGAGG TCACATGCGT GGTGGTGGAC

GTGAGCCACG AAGACCCTGA GGTCAAGTTC AACTGGTACG

TGGACGGCGT GGAGGTGCAT AATGCCAAGA CAAAGCCGCG

GGAGGAGCAG TACAACAGCA CGTACCGTGT GGTCAGCGTC

CTCACCGTCC TGCACCAGGA CTGGCTGAAT GGCAAGGAGT

ACAAGTGCAA GGTCTCCAAC AAAGCCCTCC CAGCCCCCAT

CGAGAAAACC ATCTCCAAAG CCAAAGGGCA GCCCCGAGAA

CCACAGGTGT ACACCCTGCC CCCATCCCGG GAGGAGATGA

CCAAGAACCA GGTCAGCCTG ACCTGCCTGG TCAAAGGCTT

CTATCCCAGC GACATCGCCG TGGAGTGGGA GAGCAATGGG

CAGCCGGAGA ACAACTACAA GACCACGCCT CCCGTGCTGG

ACTCCGACGG CTCCTTCTTC CTCTATAGCA AGCTCACCGT

GGACAAGAGC AGGTGGCAGC AGGGGAACGT CTTCTCATGC

TCCGTGATGC ATGAGGCTCT GCACAACCAC TACACGCAGA

AGAGCCTCTC CCTGTCTCCG GGTAAATGA

The following protein species were isolated:
(1) The hALK3(GA,30-146)-hFc shown below (SEQ ID NO:33), which retains an initial glycine-alanine from the leader sequence.

(SEQ ID NO: 33)

GALHGT

GMKSDSDQKK SENGVTLAPE DTLPFLKCYC SGHCPDDAIN

NTCITNGHCF AIIEEDDQGE TTLASGCMKY EGSDFQCKDS

PKAQLRRTIE CCRTNLCNQY LQPTLPPVVI GPFTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*

(2) The hALK3(A,30-146)-hFc shown below (SEQ ID NO:34), which retains an initial alanine from the leader sequence.

(SEQ ID NO: 34)

ALHGT

GMKSDSDQKK SENGVTLAPE DTLPFLKCYC SGHCPDDAIN

NTCITNGHCF AIIEEDDQGE TTLASGCMKY EGSDFQCKDS

PKAQLRRTIE CCRTNLCNQY LQPTLPPVVI GPFTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*

(3) The hALK3(31-146)-hFc sequence shown below (SEQ ID NO: 35), in which the leader and the initial leucine are removed, leaving an initial histidine (effectively NΔ7CΔ6).

(SEQ ID NO: 35)

HGT

GMKSDSDQKK SENGVTLAPE DTLPFLKCYC SGHCPDDAIN

NTCITNGHCF AIIEEDDQGE TTLASGCMKY EGSDFQCKDS

PKAQLRRTIE CCRTNLCNQY LQPTLPPVVI GPFTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*

(4) An additional species, hALK3(30-146)-hFc, shown below (SEQ ID NO:36) was expected but not identified by N-terminal sequencing.

(SEQ ID NO: 36)

LHGT

GMKSDSDQKK SENGVTLAPE DTLPFLKCYC SGHCPDDAIN

NTCITNGHCF AIIEEDDQGE TTLASGCMKY EGSDFQCKDS

```
PKAQLRRTIE CCRTNLCNQY LQPTLPPVVI GPFTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSLTCLVKGFYPSD IAVEWESNG

QPENNYKTTP PVLDSDGSFF LYSKLTVDKS RWQQGNVFSC

SVMHEALHNH YTQKSLSLSP GK*
```

F. A Nucleic Acid Encoding hALK3(30-140)-hFc, Shown Below (SEQ ID NO: 37) may be Expressed in CHO Cells:

```
                                        (SEQ ID NO: 37)
            ATGGAT GCAATGAAGA GAGGGCTCTG

CTGTGTGCTG CTGCTGTGTG GAGCAGTCTT CGTTTCGCCC

GGCGCCCTTC ATGGCACTGG GATGAAATCA GACTCCGACC

AGAAAAAGTC AGAAAATGGA GTAACCTTAG CACCAGAGGA

TACCTTGCCT TTTTTAAAGT GCTATTGCTC AGGGCACTGT

CCAGATGATG CTATTAATAA CACATGCATA ACTAATGGAC

ATTGCTTTGC CATCATAGAA GAAGATGACC AGGGAGAAAC

CACATTAGCT TCAGGGTGTA TGAAATATGA AGGATCTGAT

TTTCAGTGCA AAGATTCTCC AAAAGCCCAG CTACGCCGGA

CAATAGAATG TTGTCGGACC AATTTATGTA ACCAGTATTT

GCAACCCACA CTGCCCCCTA CCGGTGGTGG AACTCACACA

TGCCCACCGT GCCCAGCACC TGAACTCCTG GGGGGACCGT

CAGTCTTCCT CTTCCCCCCA AAACCCAAGG ACACCCTCAT

GATCTCCCGG ACCCCTGAGG TCACATGCGT GGTGGTGGAC

GTGAGCCACG AAGACCCTGA GGTCAAGTTC AACTGGTACG

TGGACGGCGT GGAGGTGCAT AATGCCAAGA CAAAGCCGCG

GGAGGAGCAG TACAACAGCA CGTACCGTGT GGTCAGCGTC

CTCACCGTCC TGCACCAGGA CTGGCTGAAT GGCAAGGAGT

ACAAGTGCAA GGTCTCCAAC AAAGCCCTCC CAGCCCCCAT

CGAGAAAACC ATCTCCAAAG CCAAAGGGCA GCCCCGAGAA

CCACAGGTGT ACACCCTGCC CCCATCCCGG GAGGAGATGA

CCAAGAACCA GGTCAGCCTG ACCTGCCTGG TCAAAGGCTT

CTATCCCAGC GACATCGCCG TGGAGTGGGA GAGCAATGGG

CAGCCGGAGA ACAACTACAA GACCACGCCT CCCGTGCTGG

ACTCCGACGG CTCCTTCTTC CTCTATAGCA AGCTCACCGT

GGACAAGAGC AGGTGGCAGC AGGGGAACGT CTTCTCATGC

TCCGTGATGC ATGAGGCTCT GCACAACCAC TACACGCAGA

AGAGCCTCTC CCTGTCTCCG GGTAAATGA
```

The following protein species may be isolated:

(1) The hALK3(GA,30-140)-hFc shown below (SEQ ID NO:38), which retains an initial glycine-alanine from the leader sequence.

```
                                        (SEQ ID NO: 38)
GALHGTGMKS DSDQKKSENG VTLAPEDTLP FLKCYCSGHC

PDDAINNTCI TNGHCFAIIE EDDQGETTLA SGCMKYEGSD

FQCKDSPKAQ LRRTIECCRT NLCNQYLQPT LPPTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*
```

(2) The hALK3(A,30-140)-hFc shown below (SEQ ID NO:39), which retains an initial alanine from the leader sequence.

```
                                        (SEQ ID NO: 39)
 ALHGTGMKS DSDQKKSENG VTLAPEDTLP FLKCYCSGHC

PDDAINNTCI TNGHCFAIIE EDDQGETTLA SGCMKYEGSD

FQCKDSPKAQ LRRTIECCRT NLCNQYLQPT LPPTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*
```

(3) The hALK3(31-140)-hFc sequence shown below (SEQ ID NO: 40), in which the leader and the initial leucine are removed, leaving an initial histidine (effectively NΔ7CΔ12).

```
                                        (SEQ ID NO: 40)
  HGTGMKS DSDQKKSENG VTLAPEDTLP FLKCYCSGHC

PDDAINNTCI TNGHCFAIIE EDDQGETTLA SGCMKYEGSD

FQCKDSPKAQ LRRTIECCRT NLCNQYLQPT LPPTGGGTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*
```

(4) An additional species, hALK3(30-140)-hFc, shown below (SEQ ID NO:41).

```
                                        (SEQ ID NO: 41)
 LHGTGMKS DSDQKKSENG VTLAPEDTLP FLKCYCSGHC

PDDAINNTCI TNGHCFAIIE EDDQGETTLA SGCMKYEGSD

FQCKDSPKAQ LRRTIECCRT NLCNQYLQPT LPPTGGGTHT

CPPCPAPELL GGPSVFLFPP KPKDTLMISR TPEVTCVVVD

VSHEDPEVKF NWYVDGVEVH NAKTKPREEQ YNSTYRVVSV
```

-continued

```
LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP GK*
```

Incorporation by Reference

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

---

I claim:

1. A polypeptide comprising the amino acid sequence of SEQ ID NO:7.

2. The polypeptide of claim 1, wherein the polypeptide is at least 95% pure, with respect to protein contaminants, as determined by size exclusion chromatography.

3. The polypeptide of claim 1, wherein the polypeptide exhibits a dissociation constant for BMP2 or BMP4 of no greater than $10^{-8}$ M.

4. A polypeptide comprising an amino acid sequence that is at least 95% identical to the amino acid sequence of SEQ ID NO:7, wherein the polypeptide stimulates bone formation or increased bone mineral density in an animal.

5. The polypeptide of claim 1, wherein the polypeptide is glycosylated.

6. The polypeptide of claim 1, wherein the polypeptide stimulates bone formation or increased bone mineral density in an animal.

7. The polypeptide of claim 1, wherein the polypeptide is produced by expression in CHO cells.

8. A homodimer comprising two polypeptides of claim 1.

9. A pharmaceutical preparation comprising the polypeptide of claim 1.

10. The pharmaceutical preparation of claim 9, wherein said preparation is substantially pyrogen free.

11. The polypeptide of claim 4, wherein the polypeptide comprises an amino acid sequence that is at least 96% identical to the amino acid sequence of SEQ ID NO:7.

12. The polypeptide of claim 4, wherein the polypeptide comprises an amino acid sequence that is at least 97% identical to the amino acid sequence of SEQ ID NO:7.

13. The polypeptide of claim 4, wherein the polypeptide comprises an amino acid sequence that is at least 98% identical to the amino acid sequence of SEQ ID NO:7.

14. The polypeptide of claim 4, wherein the polypeptide comprises an amino acid sequence that is at least 99% identical to the amino acid sequence of SEQ ID NO:7.

15. The polypeptide of claim 4, wherein the polypeptide is at least 95% pure, with respect to protein contaminants, as determined by size exclusion chromatography.

16. The polypeptide of claim 4, wherein the polypeptide exhibits a dissociation constant for BMP2 or BMP4 of no greater than $10^{-8}$ M.

17. The polypeptide of claim 4, wherein the polypeptide is glycosylated.

18. The polypeptide of claim 4, wherein the polypeptide is produced by expression in CHO cells.

19. A homodimer comprising the polypeptide of claim 4.

20. A pharmaceutical preparation comprising the polypeptide of claim 4.

21. The pharmaceutical preparation of claim 20, wherein said preparation is substantially pyrogen free.

* * * * *